(12) United States Patent
Shachar et al.

(10) Patent No.: US 11,834,678 B2
(45) Date of Patent: Dec. 5, 2023

(54) HEMATOPOIETIC STEM CELLS WITH IMPROVED PROPERTIES

(71) Applicant: Yeda Research and Development Co. Ltd., Rehovot (IL)

(72) Inventors: Idit Shachar, Ramat-Gan (IL); Shirly Herman, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 294 days.

(21) Appl. No.: 16/762,164

(22) PCT Filed: Nov. 14, 2018

(86) PCT No.: PCT/IL2018/051231
§ 371 (c)(1),
(2) Date: May 7, 2020

(87) PCT Pub. No.: WO2019/097514
PCT Pub. Date: May 23, 2019

(65) Prior Publication Data
US 2020/0263135 A1 Aug. 20, 2020

(30) Foreign Application Priority Data
Nov. 14, 2017 (IL) .......................................... 255664

(51) Int. Cl.
| | |
|---|---|
| C12N 5/0789 | (2010.01) |
| C07K 16/28 | (2006.01) |
| A61K 39/395 | (2006.01) |
| A61K 45/06 | (2006.01) |
| A61K 35/28 | (2015.01) |

(52) U.S. Cl.
CPC ............ *C12N 5/0647* (2013.01); *A61K 35/28* (2013.01); *A61K 39/3955* (2013.01); *A61K 45/06* (2013.01); *C07K 16/2833* (2013.01); *C12N 2501/998* (2013.01)

(58) Field of Classification Search
None
See application file for complete search history.

(56) References Cited

U.S. PATENT DOCUMENTS

| | | |
|---|---|---|
| 2002/0156034 A1 | 10/2002 | Tudan et al. |
| 2011/0117061 A1* | 5/2011 | Zhang ........................ A61P 7/00 435/405 |
| 2011/0243841 A1 | 10/2011 | Chang et al. |

FOREIGN PATENT DOCUMENTS

| | | |
|---|---|---|
| WO | WO 98/17314 | 4/1998 |
| WO | WO 2006/127585 | 11/2006 |
| WO | WO 2012/174522 | 12/2012 |
| WO | WO 2017/147610 | 8/2017 |
| WO | WO 2019/097514 | 5/2019 |

OTHER PUBLICATIONS

Chen, Xiaochuan; et al; "Prevention of Acute Graft-Versus-Host Disease in Human/Mouse Xenogeneic SCID Mouse Model by Humanized Anti-CD74 Monoclonal Antibody, Milatuzumab" Blood, 120, Abstract 4105, 2012 (Year: 2012).*
Takemitsu, Hiroshi; et al; "Comparison of bone marrow and adipose tissue-derived canine mesenchymal stem cells" BMC Veterinary Research, 8, 2012 (Year: 2012).*
International Preliminary Report on Patentability dated May 28, 2020 From the International Bureau of WIPO Re. Application No. PCT/IL2018/051231. (10 Pages).
International Search Report and the Written Opinion dated Feb. 19, 2019 From the International Searching Authority Re. Application No. PCT/IL2018/051231. (18 Pages).
Office Action and Search Report dated Aug. 20, 2018 From the Israel Patent Office Re. Application No. 255664. (9 Pages).
Bonig et al. "Insights Into the Biology of Mobilized Hematopoietic Stem/Progenitor Cells Through Innovative Treatment Schedules of the CXCR4 Antagonist AMD3100", Experimental Hematology, XP025942506, 37(3): 402-415, Mar. 1, 2009.
Bucala et al. "The Integral Role of CD74 in Antigen Presentation, MIF Signal Transduction, and B Cell Survival and Homeostasis", Mini-Reviews in Medical Chemistry, 14(14): 1132-1138, Dec. 2014.
Butrym et al. "Dual Role of the CXCL12 Polymorphism in Patients With Chronic Lymphocytic Leukemia", HLA, XP055545632, 87(6): 432-438, Published Online May 13, 2016.
Chen et al. "Prevention of Acute Graft-Versus-Host Disease in A Xenogeneic SCID Mouse Model by the Humanized Anti-CD74 Antagonistic Antibody Milatuzumab", Biology of Blood and Marrow Transplantation, XO055545543, 19(1): 28-39, Jan. 1, 2013.
Cohen et al. "Cytokines as Regulators of Proliferation and Survival of Healthy and Malignant Peripheral B Cells", Cytokine, 60: 13-22, Available Online Jul. 10, 2012.
Gore et al. "Macrophage Migration Inhibitory Factor Induces B Cell Survival by Activation of A CD74-CD44 Receptor Complex", The Journal of Biological Chemistry, 283(5): 2784-2792, Published Online Dec. 4, 2007.
Haverkos et al. "A Phase I Study of Milatuzumab for Prevention of Acute Graft Versus Host Disease Following Reduced-Intensity Conditioning Allogeneic Stem Cell Transplant in Patients With Hematologic Malignancies", Biology of Blood and Marrow Transplantation, 21(2): S331-S332, # 482, Feb. 2015.
Klasen et al. "MIF Promotes B Cell Chemotaxis Through the Receptors CXCR4 and CD74 and ZAP-70 Signaling", the Journal of Immunology, XP055545823, 192(11): 5273-5284, Published Online Apr. 23, 2014.

(Continued)

*Primary Examiner* — David W Berke-Schlessel

(57) ABSTRACT

A method of generating hematopoietic stem cells for transplantation is disclosed. The method comprising: (a) collecting hematopoietic stem cells; and (b) contacting the hematopoietic stem cells with an agent capable of decreasing an activity or expression of CD74 and/or of macrophage migration inhibitory factor (MIF), to thereby generate hematopoietic stem cells for transplantation, and wherein the hematopoietic stem cells are not transduced with a lentivirus. Methods of increasing mobilization of hematopoietic stem cells and methods of treatment are also provided.

7 Claims, 15 Drawing Sheets

(56) References Cited

OTHER PUBLICATIONS

Klimmeck et al. "Transcriptome-Wide Profiling and Post-transcriptional Analysis of Hematopoietic Stem/Progenitor Cell Differentiation Toward Myeloid Commitment", Stem Cell Reports, 3(5): 858-875, Nov. 11, 2014.
Mahalingam et al. "First-in-Human, Phase I Study Assessing Imalumab (Bax69), A First-in-Class Anti-Oxidized Macrophage Migration Inhibitory Factor (OxMIF) Antibody in Advanced Solid Tumors", Journal of Clinical Oncology, Abstract Disclosures # 2518, 5 P., May 20, 2015.
Starlets et al. "Cell-Surface CD74 Initiates a Signaling Cascade Leading to Cell Proliferation and Survival", Blood, 107(12): 4807-4816, Published Online Feb. 16, 2006.
Sugiyama et al. "Maintenance of the Hematopoietic Stem Cell Pool by CXCL12-CXCR4 Chemokine Signaling in Bone Marrow Stromal Cell Niches", Immunity, 25(6): 977-988, Dec. 2006.
Toubai et al. "Effect of Macrophage Migration Inhibitory Factor (Mif) on Acute Graft-Versus-Host Disease in a Murine Model of Allogeneic Stem Cell Transplantation", Transplant Immunology, XP025013539, 16(2): 117-124, Aug. 1, 2006.
Communication Pursuant to Article 94(3) EPC dated May 7, 2021 From the European Patent Office Re. Application No. 18815359.7. (6 Pages).
Communication Pursuant to Article 94(3) EPC dated Mar. 15, 2022 From the European Patent Office Re. Application No. 18815359.7. (5 Pages).
Becker-Herman et al. "CD74 Is A Regulator of Hematopoietic Stem Cell Maintenance", PLoS Biology, XP055899622, 19(3): e3001121-1-e3001121-24, Mar. 4, 2021.

\* cited by examiner

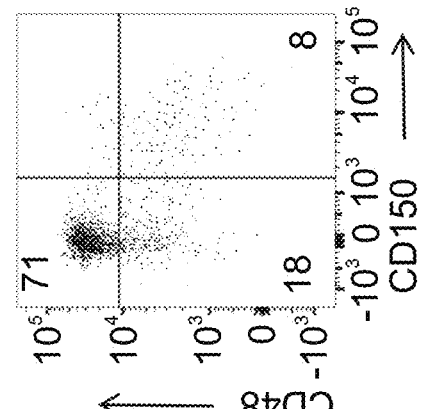
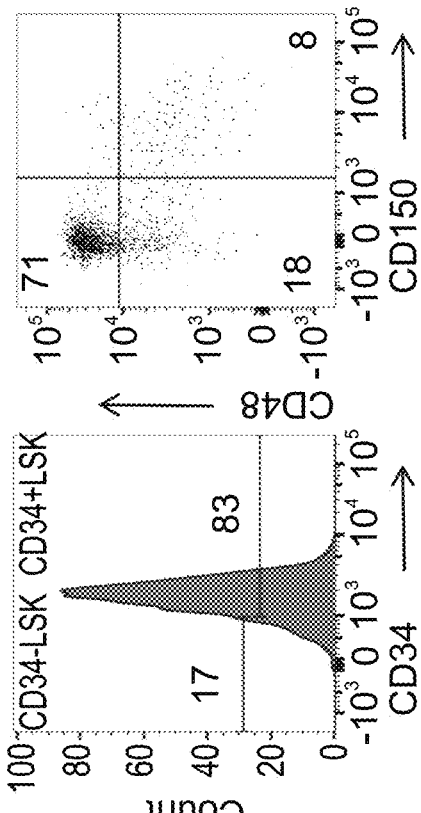
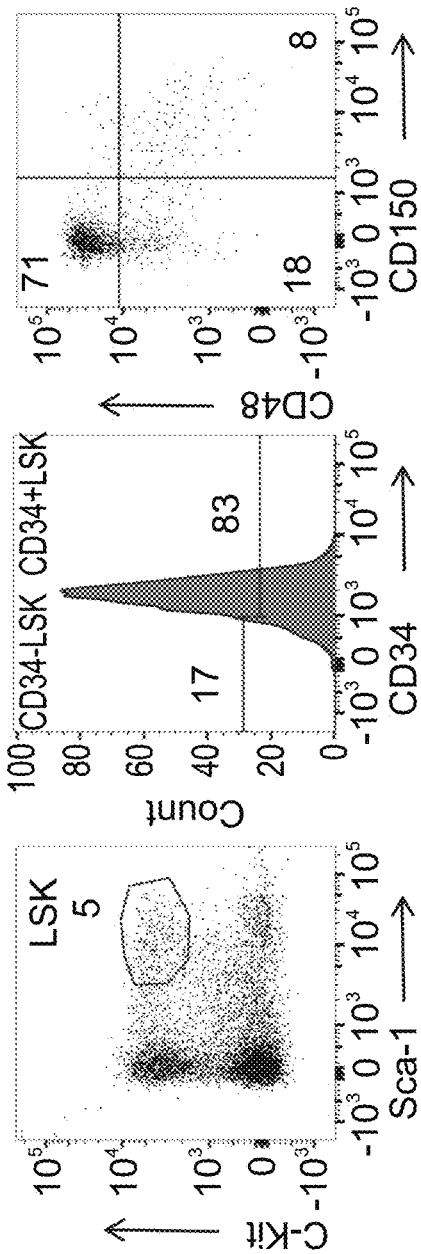
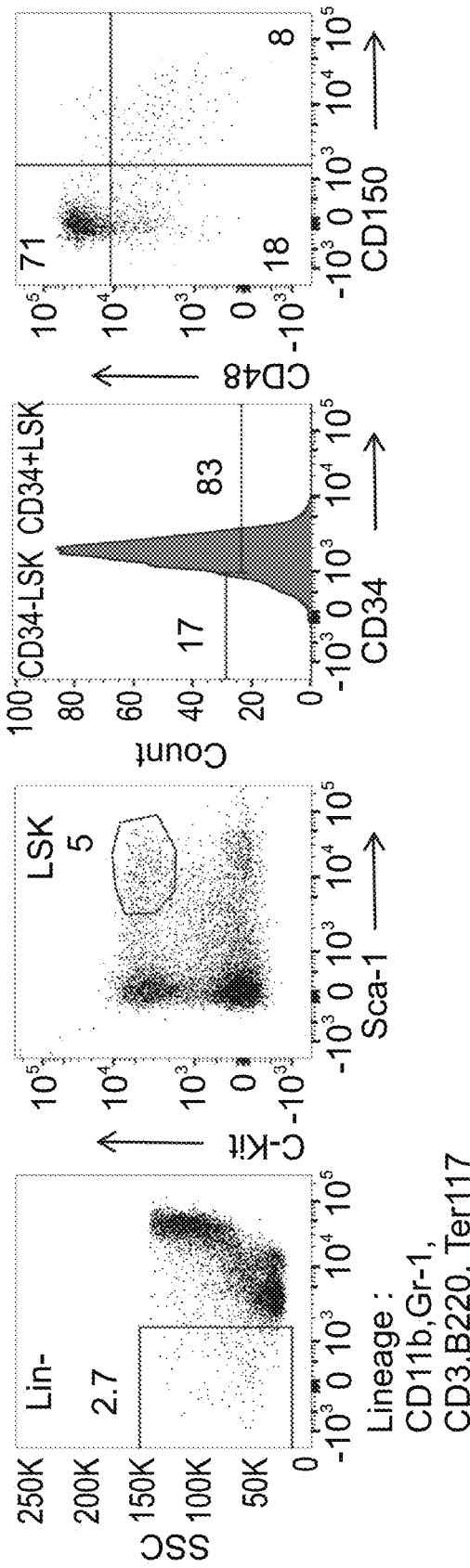
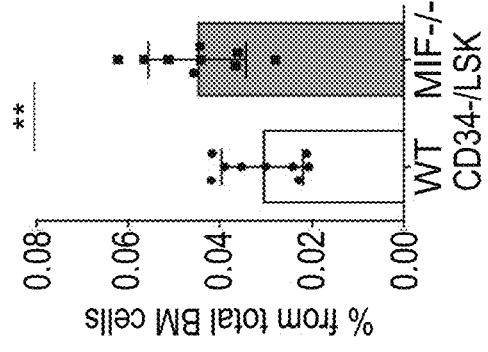
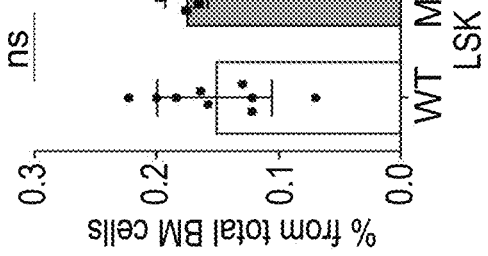
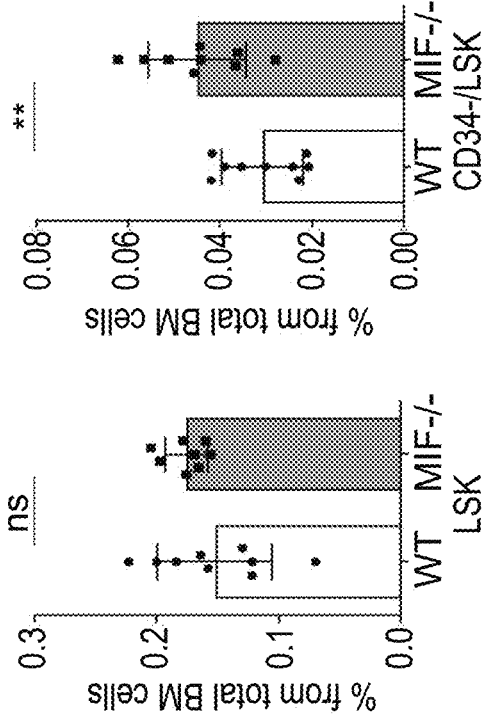
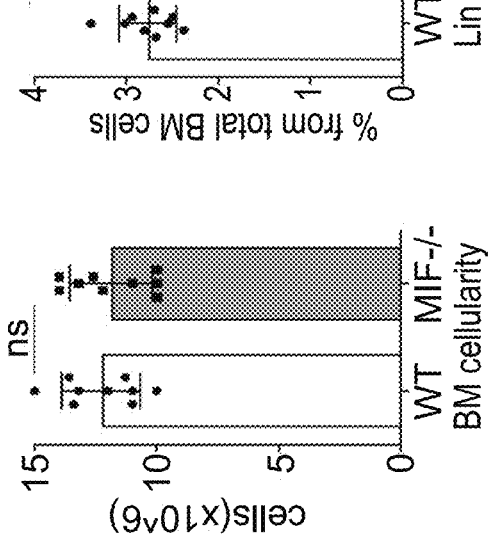

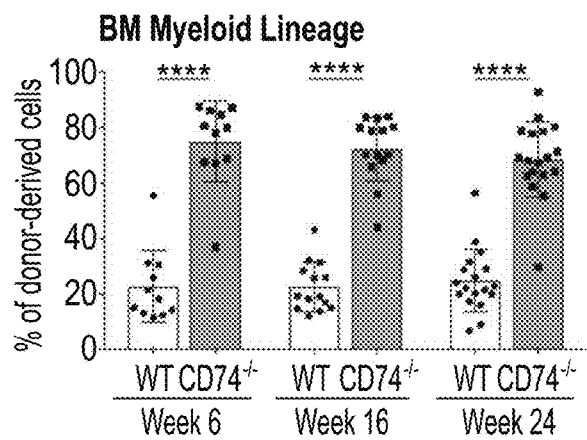
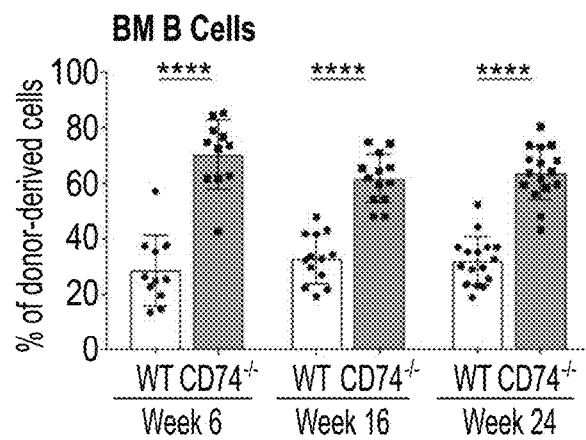
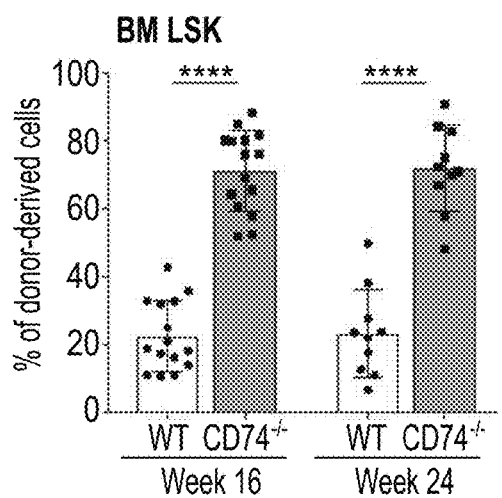
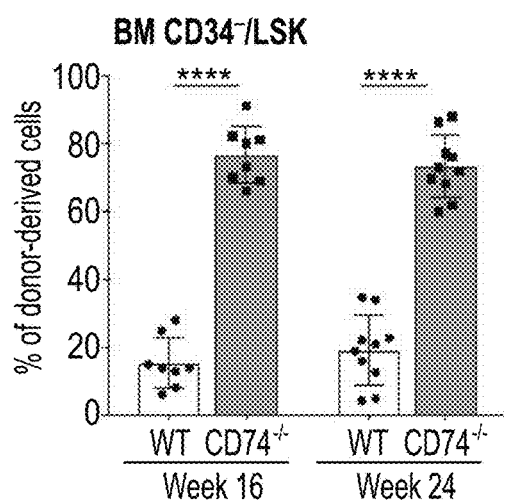
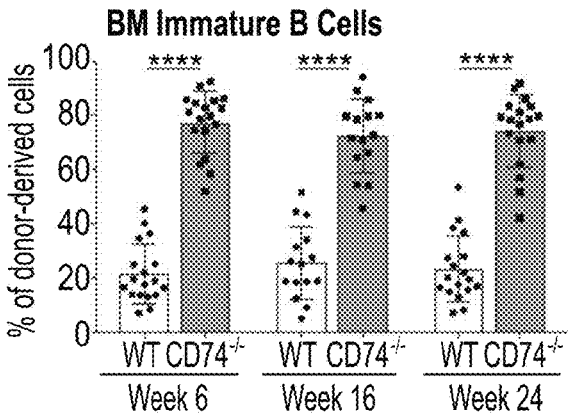
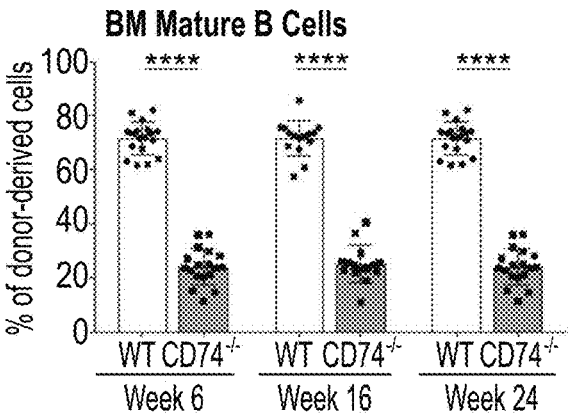

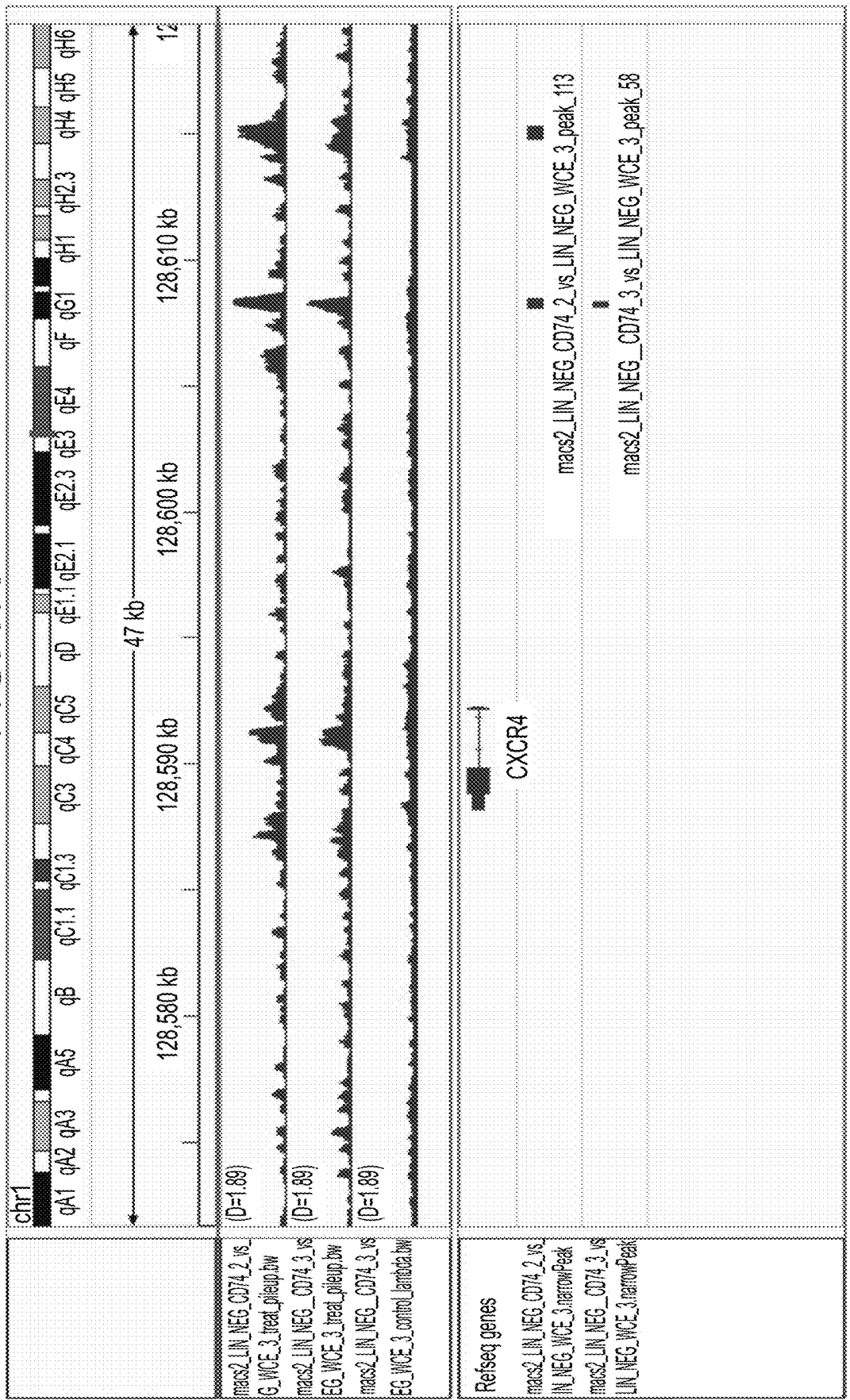

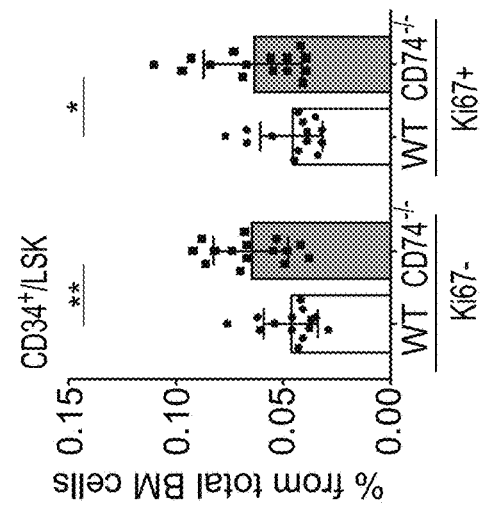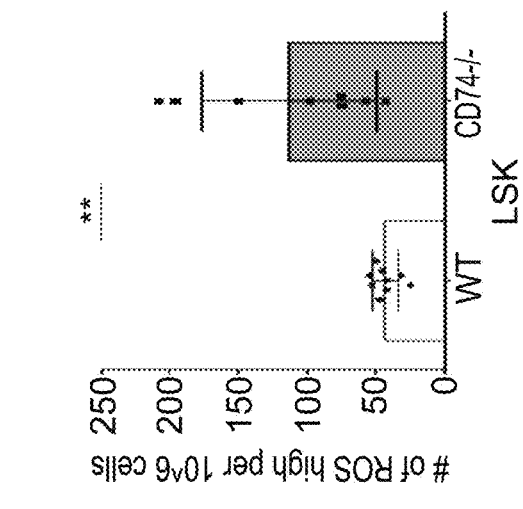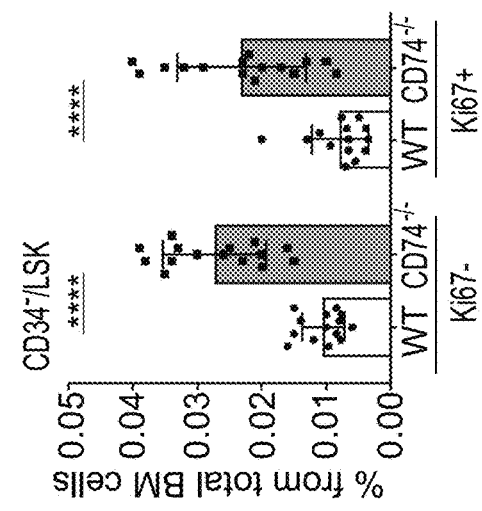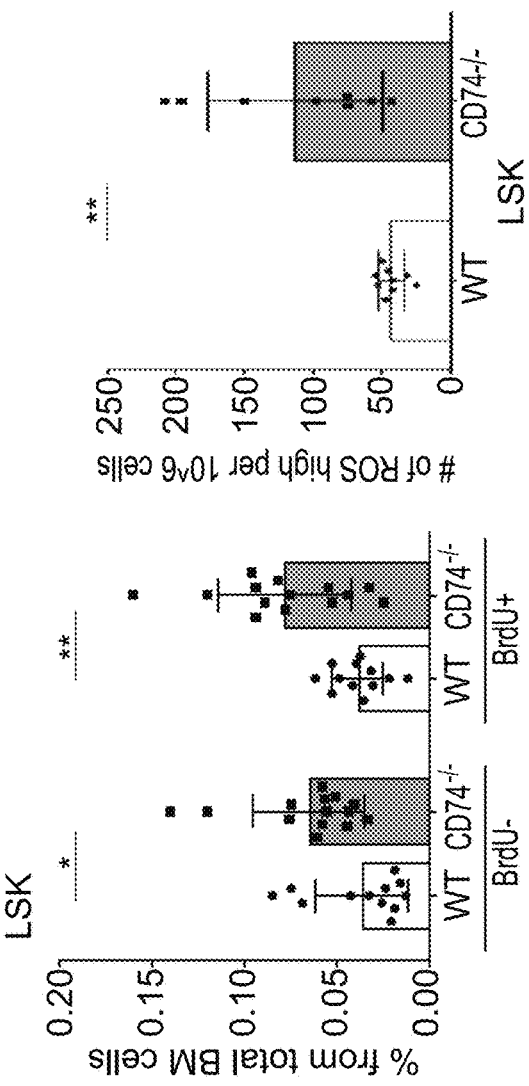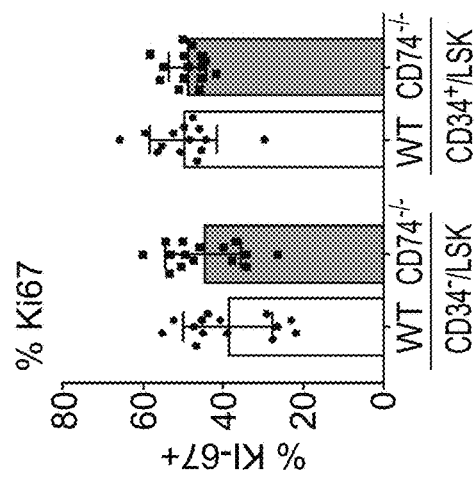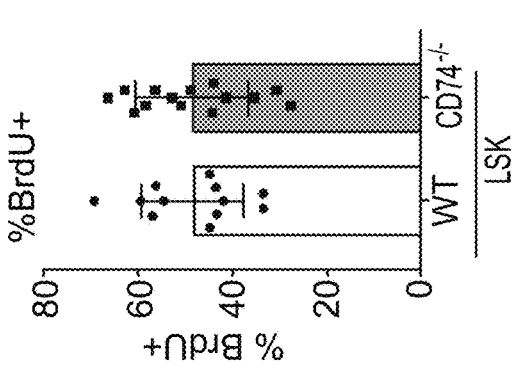

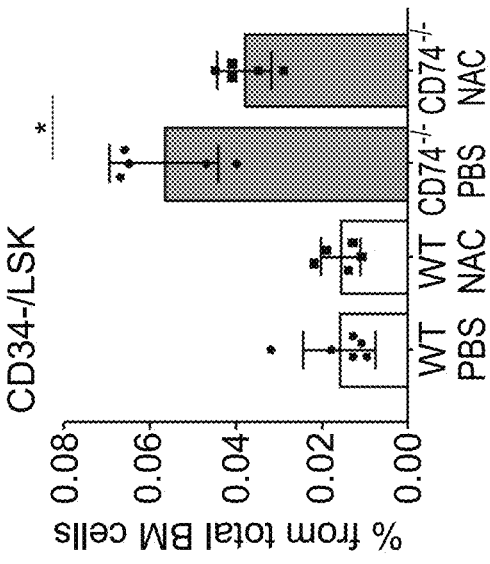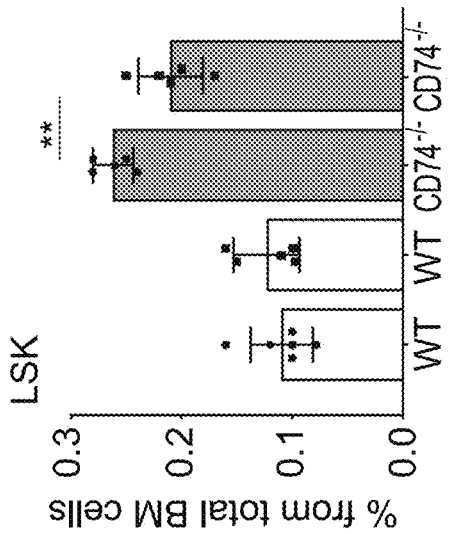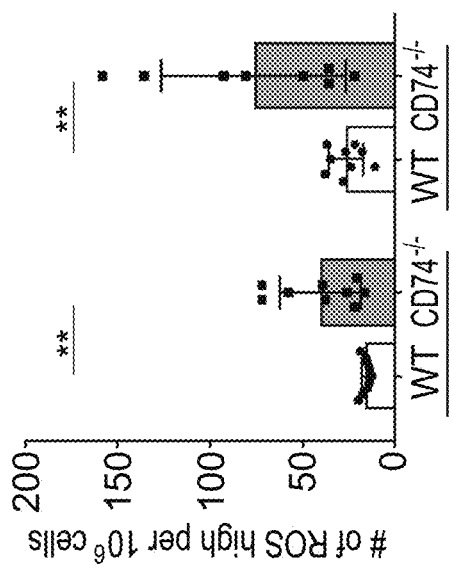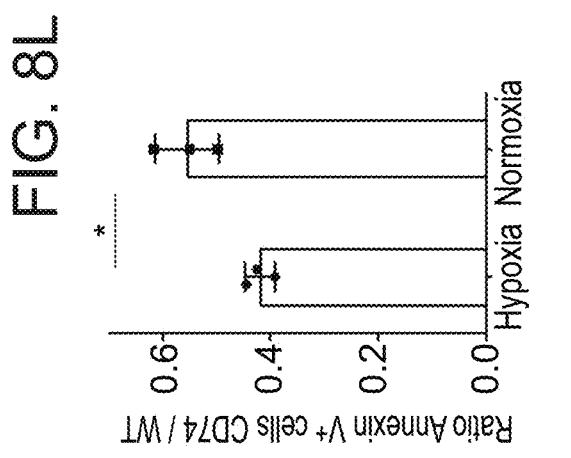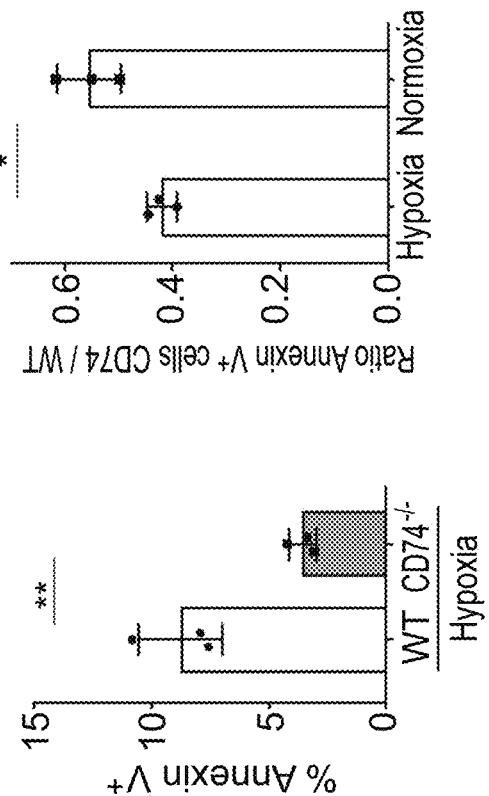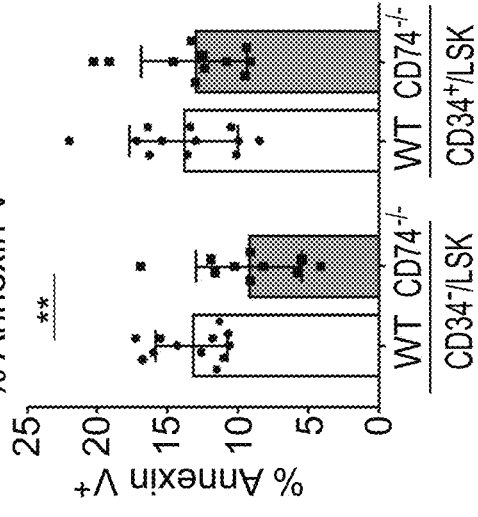

HEMATOPOIETIC STEM CELLS WITH IMPROVED PROPERTIES

RELATED APPLICATIONS

This application is a National Phase of PCT Patent Application No. PCT/IL2018/051231 having International filing date of Nov. 14, 2018, which claims the benefit of priority of Israel Patent Application No. 255664 filed on Nov. 14, 2017. The contents of the above applications are all incorporated by reference as if fully set forth herein in their entirety.

FIELD AND BACKGROUND OF THE INVENTION

The present invention, in some embodiments thereof, relates to hematopoietic stem cells devoid of CD74 or macrophage migration inhibitory factor (MIF) activity or expression and, more particularly, but not exclusively, to methods of generating same and use of same in disease treatment.

Long-term repopulating hematopoietic stem cells (HSCs) maintain continued blood cell production and host immunity throughout life. During inflammation, injury and blood loss these HSCs respond to cell demand. HSCs are defined by their ability to self-renewal and differentiate into all blood cell lineages. They are able to undergo both symmetric division to produce two daughter cell that are both HSCs or both hematopoietic progenitors cells (HPCs) and asymmetric division to generate one HSC and one HPC.

The bone marrow (BM) is the main site of adult hematopoiesis and the majority of HSCs remain confined to the BM microenvironment in a quiescent non-motile mode via adhesive interactions. The chemokine CXCL12 and its major receptor CXCR4 are essential for adhesion and retention of HSCs in mouse bone marrow. CXCR4$^+$ HSCs tightly adhere to bone marrow stromal cells, which express functional, membrane-bound CXCL12 (Sugiyama et al., 2006).

CD74 is a type II transmembrane protein expressed on antigen presenting cells, and was initially demonstrated to function as an MHC class II chaperone. Cell surface CD74 serves as a receptor for the cytokine macrophage migration inhibitory factor (MIF) on many cell types. In terminally differentiated immune cells, MIF binding to CD74 induces a signaling cascade that results in regulation of cell proliferation and survival (Bucala and Shachar, 2014).

In B cells, CD74 expression is directly involved in shaping the B cell repertoire by regulating mature B cell survival (Cohen and Shachar, 2012). MIF binding to CD74 induces a signaling pathway that involves the Syk tyrosine kinase and the PI3K/Akt pathway, induction of CD74 intramembrane cleavage and the release of the CD74 intracellular domain (CD74-ICD). CD74-ICD translocates to the nucleus, where it induces activation of transcription mediated by the NF-κB RelA protein and its co-activator, TAFII105, resulting in regulation of transcription of genes that control B cell proliferation and survival (Gore et al., 2008; Starlets et al., 2006). Thus, MIF binding to CD74 initiates a cascade that results in B cell proliferation and the rescue of these cells from apoptotic death.

CD74 mRNA was also found to be expressed in hematopoietic stem and hematopoietic progenitors cells (HSPCs) (Klimmeck et al., 2014).

Additional Background Art Includes:

U.S. Patent Application No. 2002/0156034 relates to the use of CXCR4 antagonists for the treatment of hematopoietic cells, such as progenitor or stem cells, to promote the rate of cellular multiplication, self-renewal, proliferation or expansion.

PCT Publication No. WO 1998017314 relates to the use of macrophage migration inhibitory factor (MIF) antagonists for anti-cancer therapy.

PCT publication no. WO 9817314 provides methods of treating or preventing a disease which involves cell overproliferation (e.g. cancer) in a subject comprising administering to the subject a therapeutically effective amount of a MIF antagonist agent.

Mahalingam et al., *J of Clinical Oncology* (2015) 33(15) Suppl, provides a clinical study assessing imalumab (Bax69), a first-in-class anti-oxidized macrophage migration inhibitory factor (oxMIF) antibody, in advanced solid tumors.

Haverkos et al. *Biology of Blood and Marrow Transplantation*, (2015) 21(2), S331-S332, provides a clinical study of Milatuzumab for prevention of acute graft versus host disease following reduced-intensity conditioning allogeneic stem cell transplant in patients with hematologic malignancies.

PCT publication no. WO 2006127585 provides methods, compositions, and systems relating to the stable transduction of primary cells of the hematopoietic system and/or hematopoietic stem cells. According to WO 2006127585, the method comprises contacting the primary cells with both a lentiviral vector and at least one molecule which binds the cell surface (e.g. anti-CD74 molecule).

SUMMARY OF THE INVENTION

According to an aspect of some embodiments of the present invention there is provided a method of generating hematopoietic stem cells for transplantation, the method comprising: (a) collecting hematopoietic stem cells; and (b) contacting the hematopoietic stem cells with an agent capable of decreasing an activity or expression of CD74 and/or of macrophage migration inhibitory factor (MIF), to thereby generate hematopoietic stem cells for transplantation, and wherein the hematopoietic stem cells are not transduced with a lentivirus.

According to an aspect of some embodiments of the present invention there is provided a method of obtaining hematopoietic stem cells for transplantation, the method comprising: (a) administering to a subject an effective amount of an agent capable of decreasing an activity or expression of CD74 and/or of macrophage migration inhibitory factor (MIF); and (b) collecting hematopoietic stem cells, thereby obtaining hematopoietic stem cells for transplantation, and wherein the hematopoietic stem cells are not transduced with a lentivirus.

According to an aspect of some embodiments of the present invention there is provided a method of increasing mobilization of hematopoietic stem cells from the bone marrow to the peripheral blood in a healthy subject, the method comprising administering to the subject an agent capable of decreasing an activity or expression of CD74 and/or of macrophage migration inhibitory factor (MIF), thereby increasing mobilization of hematopoietic stem cells.

According to an aspect of some embodiments of the present invention there is provided a therapeutically effective amount of an agent capable of decreasing an activity or expression of CD74 and/or of macrophage migration inhibitory factor (MIF) for use in increasing mobilization of hematopoietic stem cells from the bone marrow to the peripheral blood in a healthy subject.

According to an aspect of some embodiments of the present invention there is provided a method of treating a disease or condition in a subject in need of enhanced hematopoietic stem cell survival and/or expansion and/or mobilization, the method comprising administering to the subject a therapeutically effective amount of an agent capable of decreasing an activity or expression of CD74 and/or of macrophage migration inhibitory factor (MIF), with the proviso that when the agent is capable of decreasing the activity or expression of the CD74 the disease or condition is not a cancer and when the agent is capable of decreasing the activity or expression of the MIF the disease or condition is not a cancer, autoimmune disease or infection, thereby treating the disease or condition in the subject.

According to an aspect of some embodiments of the present invention there is provided a therapeutically effective amount of an agent capable of decreasing an activity or expression of CD74 and/or of macrophage migration inhibitory factor (MIF) for use in treating a disease or condition in a subject in need of enhanced hematopoietic stem cell survival and/or expansion and/or mobilization, with the proviso that when the agent is capable of decreasing the activity or expression of the CD74 the disease or condition is not a cancer and when the agent is capable of decreasing the activity or expression of the MIF the disease or condition is not a cancer, autoimmune disease or infection.

According to an aspect of some embodiments of the present invention there is provided an isolated population of hematopoietic stem cells obtainable by the method of some embodiments of the invention.

According to an aspect of some embodiments of the present invention there is provided an isolated population of hematopoietic stem cells comprising an agent capable of decreasing an activity or expression of CD74, and wherein the hematopoietic stem cells are not transduced with a lentivirus.

According to an aspect of some embodiments of the present invention there is provided a pharmaceutical composition comprising the isolated population of cells of some embodiments of the invention and a pharmaceutically acceptable carrier or diluent.

According to an aspect of some embodiments of the present invention there is provided a method of treating a disease or condition requiring hematopoietic stem cell transplantation in a subject in need thereof, the method comprising administering to the subject a therapeutically effective amount of the isolated population of cells of some embodiments of the invention.

According to an aspect of some embodiments of the present invention there is provided a therapeutically effective amount of the isolated population of cells of some embodiments of the invention for use in treating a disease or condition requiring hematopoietic stem cell transplantation in a subject in need thereof.

According to some embodiments of the invention, the method further comprises isolating hematopoietic stem cells having CD74 levels below a predetermined threshold.

According to some embodiments of the invention, the contacting is effected ex vivo or in vitro.

According to some embodiments of the invention, the hematopoietic stem cells have an increased survival as compared to hematopoietic stem cells not contacted with the agent capable of decreasing an activity or expression of the CD74 and/or of the MIF.

According to some embodiments of the invention, the hematopoietic stem cells have an increased expansion potential while maintaining their differentiation potential as compared to hematopoietic stem cells not contacted with the agent capable of decreasing an activity or expression of the CD74 and/or of the MIF.

According to some embodiments of the invention, the subject is a healthy subject.

According to some embodiments of the invention, the method further comprises a step of mobilizing the hematopoietic stem cells from the bone marrow to the peripheral blood prior to collecting.

According to some embodiments of the invention, collecting the hematopoietic stem cells is from the peripheral blood.

According to some embodiments of the invention, the method or agent for use further comprises collecting hematopoietic stem cells from the peripheral blood.

According to some embodiments of the invention, collecting the hematopoietic stem cells is effected by a procedure selected from the group consisting of: (i) a surgical procedure; and (ii) an apheresis procedure.

According to some embodiments of the invention, the method further comprises administering to the subject a chemotherapeutic agent.

According to some embodiments of the invention, the agent for use further comprises the use of a chemotherapeutic agent.

According to some embodiments of the invention, the subject is in need of a hematopoietic stem cell transplantation.

According to some embodiments of the invention, the subject is immunocompromised.

According to some embodiments of the invention, the hematopoietic stem cells are derived from a source selected from the group consisting of bone marrow, peripheral blood and neonatal umbilical cord blood.

According to some embodiments of the invention, the hematopoietic stem cells are characterized by the phenotype CD34$^+$, CD59$^+$, CD90/Thy1$^+$, CD38$^{+/-}$, c-Kit$^{-/+}$, and Lin$^-$.

According to some embodiments of the invention, the hematopoietic stem cells are characterized by the phenotype CD34$^+$, CD59$^+$, CD90/Thy1$^-$, CD38$^{+/-}$, c-Kit$^{-/+}$, and Lin$^-$.

According to some embodiments of the invention, the hematopoietic stem cells are capable of differentiating into myeloid cells and/or lymphoid cells.

According to some embodiments of the invention, the agent capable of decreasing an activity or expression of CD74 and/or of MIF is a polynucleotide agent.

According to some embodiments of the invention, the agent capable of decreasing an activity or expression of CD74 and/or of MIF is a small molecule.

According to some embodiments of the invention, the agent capable of decreasing an activity or expression of CD74 and/or of MIF is an antibody.

According to some embodiments of the invention, the antibody binds at least one epitope of an extracellular portion of the CD74.

According to some embodiments of the invention, the antibody does not comprise a tag.

According to some embodiments of the invention, the agent capable of decreasing an activity or expression of CD74 and/or of MIF prevents the binding of the MIF to the CD74.

According to some embodiments of the invention, the agent capable of decreasing an activity or expression of CD74 and/or of MIF downregulates an activity or expression of CXCR4 in the hematopoietic stem cells.

According to some embodiments of the invention, the agent capable of decreasing an activity or expression of CD74 upregulates content of reactive oxygen species (ROS) in the hematopoietic stem cells.

According to some embodiments of the invention, the agent capable of decreasing an activity or expression of CD74 is Milatuzumab.

According to some embodiments of the invention, the agent capable of decreasing an activity or expression of MIF is Imalumab.

According to some embodiments of the invention, the chemotherapeutic agent is a myelotoxic agent.

According to some embodiments of the invention, the chemotherapeutic agent is a Fluorouracil (5-FU).

According to some embodiments of the invention, the cells are cultured ex vivo or in vitro.

According to some embodiments of the invention, the isolated population of hematopoietic stem cells is syngeneic with respect to the subject.

According to some embodiments of the invention, the isolated population of hematopoietic stem cells is non-syngeneic with respect to the subject.

According to some embodiments of the invention, the disease or condition is a malignant disease.

According to some embodiments of the invention, the malignant disease is a hematopoietic cancer.

According to some embodiments of the invention, the hematopoietic cancer comprises a leukemia or lymphoma.

According to some embodiments of the invention, the disease or condition is a non-malignant disease.

According to some embodiments of the invention, the non-malignant disease is a disease that can be alleviated by hematopoietic stem cell transplantation and is selected from the group consisting of a genetic disease or disorder, an autoimmune disease, an immune deficiency, a transplantation related disease, and a metabolic disorder.

According to some embodiments of the invention, the disease or condition is a disease that can be alleviated by hematopoietic stem cell transplantation and is selected from the group consisting of genetic disease or disorder, an immune deficiency, a transplantation related disease, or a metabolic disorder that can be alleviated by hematopoietic stem cell transplantation.

According to some embodiments of the invention, the subject is a human subject.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

(FIG. 1A) Representative FACS staining of CD74 for HSPCs from WT and $CD74^{-/-}$ mice, n=3. (FIG. 1B) Total number of BM cellularity per femur and tibia in WT and $CD74^{-/-}$ mice. (FIGS. 1C-I) Representative FACS staining—WT and $CD74^{-/-}$ mice were analyzed and percentage from total BM were calculated for (FIG. 1C) $Lin^-$; (FIG. 1D+E) LSK; (FIG. 1E+F) $CD34^-$ LSK and $CD34^+$ LSK; (FIG. 1G) CD150+CD48-LSK; (FIG. 1H) CD150-CD48-LSK; and (FIG. 1I) $CD150-CD48^+$ LSK, n=14-18. Results are presented as mean±s.d. (unpaired t-test two tailed *<0.05; <0.005; *<0.0005). (FIG. 1J) Survival curve: 5FU (150 mg/kg) was injected into WT and $CD74^{-/-}$ mice once a week for two weeks, Log-rank test *<0.05, n=10 in each group.

FIGS. 2A-H illustrate (FIGS. 2A-D) gating strategies for HSPCs. (FIG. 2A) Lin negative; (FIG. 2B) LSK; (FIG. 2C) $CD34^-$ and $CD34^+$; (FIG. 2D) CD48 and CD150 populations. (FIGS. 2E-H) MIF deficient mice have a milder HSPC accumulation. BM cells derived from WT or $MIF^{-/-}$ mice were analyzed for (FIG. 2E) total number of BM cellularity per femur and tibia; (FIG. 2F) percent of total BM calculated from $Lin^-$; (FIG. 2G) percent of total BM of LSK; (FIG. 2H) percent of total BM of $CD34^-$ LSK, n=9. Results are presented as mean±s.d. (unpaired t-test two tailed *<0.05, <0.005, *<0.0005).

(FIG. 3B) LSK; (FIG. 3C) $CD34^-LSK$. n=5-12. Results are presented as mean±s.d. (unpaired t-test two tailed *<0.05; <0.005; *<0.0005).

FIGS. 4A-I illustrate that CD74 deficient HSPCs show an advantage in cell repopulation. (FIG. 4A) Colony-forming unit cells (CFU-C) assay: total BM cells from WT and $CD74^{-/-}$ mice seeded 15,000 cells/mL in semisolid cultures supplemented with cytokines and nutrients. CFU-C were counted 7 days later, n=7. (FIGS. 4B-I) Lethally irradiated WT (CD45.1) mice were transplanted with WT (CD45.2) or $CD74^{-/-}$ (CD45.2) mice in 1:1 ratio. (FIG. 4B) Representative bone marrow FACS staining. Percentage from donor-derived cells were analyzed in the BM after 6, 16 and 24 weeks for (FIG. 4C) Total BM cells; (FIG. 4D) Myeloid cells; (FIG. 4E) B cells; (FIG. 4F) LSK cells; (FIG. 4G) $CD34^-LSK$ cells; (FIG. 4H) BM immature B cells; and (FIG. 4I) BM mature B cells. n=8-18.

(FIG. 5A) percent total BM cells; (FIG. 5B) percent myeloid cells; (FIG. 5C) percent BM immature B cells; (FIG. 5D) Percent BM mature B cells; and (FIG. 5E) percent LSK; at the various time points. n=8-11. Results are presented as mean±s.d. (unpaired t-test two tailed *<0.05; <0.005; *<0.0005).

(FIG. 6B) Myeloid cells; (FIG. 6C) BM immature B cells; and (FIG. 6D) BM mature B cells. (FIG. 6E) Percentage from donor-derived cells were analyzed for LSK and $CD34^-LSK$ cells 18 weeks post-transplant. n=6-8.

Results are presented as mean±s.d. (unpaired t-test two tailed *<0.05; <0.005; *<0.0005). (FIGS. 6F-I) Kaplan-Meier survival curves for serial transplantation assay. Six donors from each genotype were transplanted to lethal irradiated 4-5 hosts. After 10-12 weeks, one mouse from each donor served as a donor for the following transplant. n=20-30 mice in each transplant for a genotype.

FIGS. 7A-F illustrate that CD74 regulates stem cell retention. (FIG. 7A) Binding of CD74-ICD to CXCR4 promoter region in CLL cell samples. ChIP-seq analysis using anti-CD74 or isotype control antibodies. (FIG. 7B-C) FACS analysis for CXCR4 on BM LSK and BM CD34$^-$/LSK of WT and CD74$^{-/-}$ mice, n=7. (FIGS. 7D-F) FACS analysis for HSPCs in the peripheral blood (PB) of WT and CD74$^{-/-}$ mice: (FIG. 7D) Dot blot analysis of LSK in WT and CD74$^{-/-}$ mice; and (FIGS. 7E-F) Cell number counts of (FIG. 7E) LSK and (FIG. 7F) CD34$^-$LSK in 600 µl blood. WT n=6 CD74$^{-/-}$ n=7. Results are presented as mean±s.d. (unpaired t-test two tailed *<0.05; <0.005; *<0.0005).

FIGS. 8A-L illustrate that CD74 regulates stem cell retention. (FIGS. 8A-C) FACS staining of HSPCs from WT and CD74$^{-/-}$ mice for Ki-67. Results are represented as: (FIG. 8A) Percentage of Ki-67$^+$ from CD34$^-$LSK and percentage of Ki-67$^+$ from CD34$^+$ LSK, (FIG. 8B) percentage of CD34–LSK Ki-67– and CD34–LSK Ki-67+ from total BM cells and (FIG. 8C) percentage of CD34$^+$ LSK Ki-67$^-$ and CD34$^+$ LSK Ki-67$^+$ from total BM cells, n=15. (FIGS. 8D-E) Mice were fed with 0.8 mg/ml BrdU in the drinking water for 3 days and BrdU incorporation was analyzed by FACS. Results are represented as: (FIG. 8D) % BrdU$^+$ in LSK; (FIG. 8E) percentage of LSK BrdU$^-$ and percentage of LSK BrdU$^+$ from total BM cells, n=12-14. (FIG. 8F-G) FACS staining of HSPCs from WT and CD74$^{-/-}$ mice for ROS. Results are represented as number of ROS high in million cells, n=9. (FIGS. 8H-I) percentage of HSPCs after 6 days of NAC injections mg/ml, n=5. (FIG. 8J) FACS staining of HSPCs from WT and CD74$^{-/-}$ mice for Annexin V, n=10-12, and after 24 hours in hypoxia (FIG. 8K), n=4-5. (FIG. 8L) Ratio of Annexin V+CD74$^{-/-}$ to WT of HSPCs in hypoxia and normoxic conditions. Bars show SEM. Unpaired t-test two tailed *<0.05 **<0.01.

(FIG. 9B) myeloid cells; (FIG. 9C) immature B cells; (FIG. 9D) mature B cells; (FIG. 9E) LSK; (FIG. 9F) CD34$^-$LSK; n=8. Results are presented as mean±s.d. (unpaired t-test two tailed *<0.05; <0.005; *<0.0005).

DESCRIPTION OF SPECIFIC EMBODIMENTS OF THE INVENTION

Figure 1A:
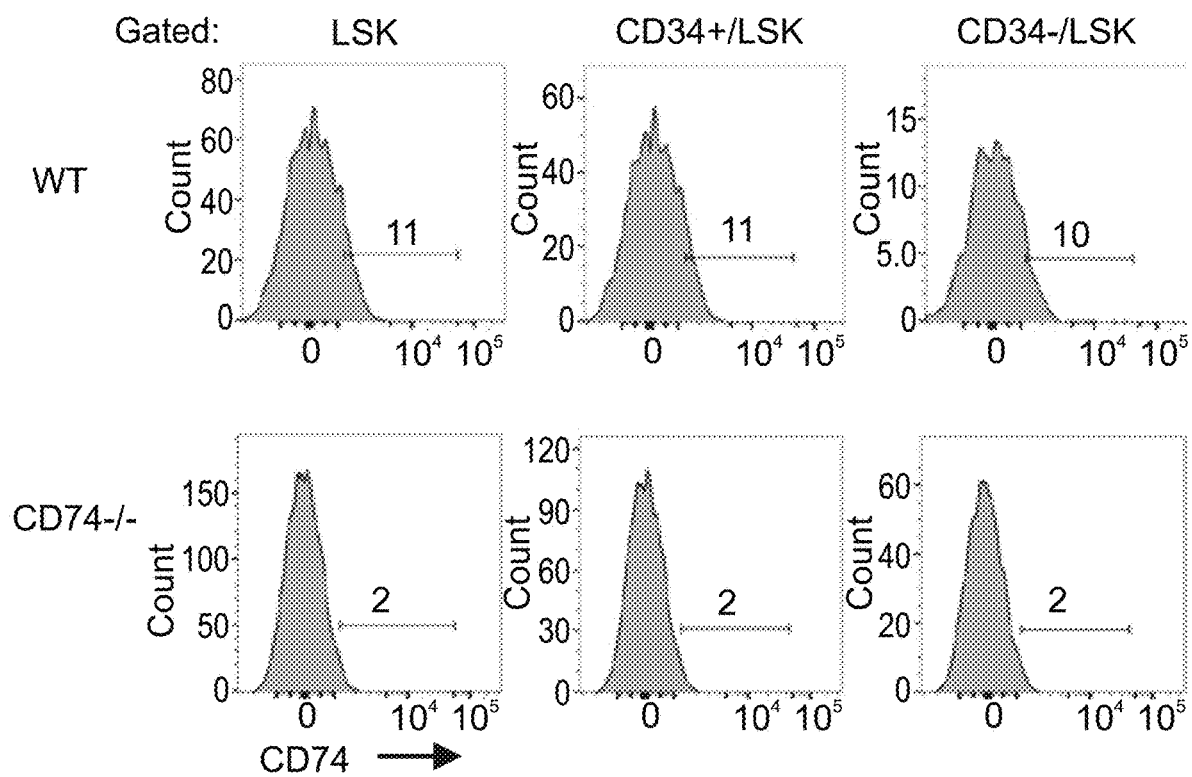
FIGS. 1A-J illustrate expansion of HSPCs in the BM of $CD74^{-/-}$ mice.

The present invention, in some embodiments thereof, relates to hematopoietic stem cells devoid of CD74 or MIF activity or expression and, more particularly, but not exclusively, to methods of generating same and use of same in disease treatment.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

CD74, a type II transmembrane protein, is expressed on antigen presenting cells and B cells, and was initially demonstrated to function as an MHC class II chaperone. CD74 mRNA was also previously described to be expressed in hematopoietic stem and hematopoietic progenitors cells (HSPCs) (Klimmeck et al., 2014). Cell surface CD74 serves as a receptor for the cytokine macrophage migration inhibitory factor (MIF) on many cell types. In terminally differentiated immune cells, MIF binding to CD74 induces a signaling cascade that results in regulation of cell proliferation and survival (Bucala and Shachar, 2014).

While reducing the present invention to practice, the present inventors have uncovered the role of CD74 in HSPCs survival and expansion. Specifically, the present inventors discovered that the MIF/CD74 axis plays a crucial role in HSPCs survival and self-renewal. Deficiency of CD74 and MIF leads to expansion of hematopoietic stem cells and progenitors in the bone marrow (BM) (see Example 1 of the Examples section which follows). These CD74 deficient cells display a better long-term self-renewal capacity by reduced apoptosis (see Examples 2 and 3 of the Examples section which follows), are capable of differentiating into myeloid cells and lymphoid cells (see Example 2 of the Examples section which follows) and comprise enhanced mobilization properties from the bone marrow to the peripheral blood (see FIGS. 7D-F). Furthermore, the present inventors demonstrated that CD74 regulates HSPCs by regulating CXCR4 expression. Specifically, in the absence of CD74, lower CXCR4 levels result in reduced retention of HSPCs in the BM (see Example 3 of the Examples section which follows) substantiating a role for MIF/CD74 in HSC mobilization to the peripheral blood. Moreover, according to the present teachings, reactive oxygen species (ROS) levels are upregulated in HSPCs lacking CD74 (see Example 3 of the Examples section which follows). Taken together, these results substantiate the importance of modulation of the MIF/CD74 axis for therapeutic indications such as for bone marrow transplantation protocols, as well as in diseases associated with hematopoietic failure.

Thus, according to one aspect of the present invention there is provided a method of generating hematopoietic stem cells for transplantation, the method comprising: (a) collecting hematopoietic stem cells; and (b) contacting the hematopoietic stem cells with an agent capable of decreasing an activity or expression of CD74 and/or of macrophage migration inhibitory factor (MIF), to thereby generate hematopoietic stem cells for transplantation.

According to one embodiment, the hematopoietic stem cells are not transduced with a lentivirus.

According to a specific embodiment, the hematopoietic stem cells are not transduced with a lentivirus vector.

The term "Lentivirus" as used herein refers to the RNA virus (retrovirus). Lentivirus, can be, for example, a HIV virus (e.g. HIV-I or HIV-2), a Visna/maedi virus, a feline immunodeficiency virus (FIV), a bovine lentivirus, a simian immunodeficiency virus (SIV), an equine infectious anemia virus (EIAV), or a caprine arthritis-encephalitis virus (CAEV).

The term "hematopoietic stem cells" or "HSCs" as used herein refers to immature blood cells having the capacity to self-renew (i.e. expand) and to differentiate into a blood cell e.g. lymphoid cells and myeloid cells.

HSCs can be committed to a particular line of differentiation, e.g. common myeloid progenitors (CMP), common lymphoid progenitor (CLP), Colony-Forming Unit-Granulocyte/Erythrocyte/Macrophage/Megakaryocyte (CFU-GEMM). These then give rise to hematopoietic lineage committed progenitor cells including, but are not limited to, CFU-GM (colony forming unit-granulocyte-monocyte), CFU-E (colony forming unit-erythrocyte), BFU-E (burst forming unit-erythrocyte), CFU-G (colony forming unit-granulocyte), CFU-eo (colony forming unit-eosinophil), and CFU-Meg (colony forming unit-megakaryocyte).

Accordingly, HSCs are capable of differentiating into any of granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages, dendritic cells) and lymphocytes (common lymphoid progenitors, pre-B, pro-B, mature B, pre-T, pro-B, mature T and NKT lymphocytes and NK cells). The HSCs committed to specific hematopoietic lineages may be of T cell lineage, B cell lineage, dendritic cell lineage, Langerhans cell lineage, erythroid, megakaryocytic, myeloid and/or macrophage cell lineage.

According to one embodiment, the hematopoietic stem cells are human hematopoietic stem cells.

Human hematopoietic stem cells are typically characterized by the marker expression: $CD34^+$, $CD59$, $Thy1/CD90^+$, $CD38^-$, $C\text{-kit}/CD117^+$, $Lin^-$. However, hematopoietic stem cells may lack expression of CD34 ($CD34^-$) and thus may comprise the phenotype $CD34^-$, $CD59$, $Thy1/CD90^+$, $CD38^-$, $C\text{-kit}/CD117^+$, $Lin^-$. Hematopoietic stem cells may also lack expression of C-kit ($C\text{-kit}/CD117^-$) and thus may comprise the phenotype $CD34^{+/-}$, $CD59^+$, $Thy1/CD90^+$, $CD38^-$, $C\text{-kit}/CD117^-$, $Lin^-$. Additionally or alternatively, human hematopoietic stem cells may be positive for expression of CD133 ($CD133^+$) and thus may comprise the phenotype $CD34^+$, $CD133^+$.

According to one embodiment, the hematopoietic stem cells are long term stem cells.

According to one embodiment, long term stem cells may comprise the phenotype $CD34^+$, $CD59^+$, $CD90/Thy1^+$, $CD38^{low/-}$, $c\text{-Kit}^{-/low}$, and $Lin^-$. According to another embodiment, long term stem cells may lack expression of CD34 ($CD34^-$) and thus may comprise the phenotype $CD34^-$, $CD59^+$, $CD90/Thy1^+$, $CD38^{low/-}$, $c\text{-Kit}^{-/low}$, and $Lin^-$.

According to one embodiment, the hematopoietic stem cells are short term stem cells.

According to one embodiment, short term stem cells may comprise the phenotype $CD34^+$, $CD59^+$, $CD90/Thy1^-$, $CD38^{low/-}$, $c\text{-Kit}^{-/low}$, and $Lin^-$.

According to one embodiment, the hematopoietic stem cells are umbilical cord stem cells.

According to one embodiment, umbilical cord stem cells may comprise the phenotype $CD34^+$, $CD133^+$.

Hematopoietic stem cells as used herein may be derived from any source known in the art, such as from a biological sample, for example, bone marrow, mobilized peripheral blood (e.g. mobilization of $CD34^+$ cells to enhance their concentration), cord blood (e.g. umbilical cord), fetal liver, yolk sac, placenta, and/or cell line.

According to one embodiment, the hematopoietic stem cells generated by the methods of some embodiments of the invention have an increased survival as compared to hematopoietic stem cells not contacted with an agent capable of decreasing an activity or expression of CD74 and/or of MIF.

According to one embodiment, survival of hematopoietic stem cells is increased by at least about 10%, 20%, 30%, 40%, 50%, 60%, 70%, 80%, 90%, 100%, 120%, 150% or 200% as compared to hematopoietic stem cells not treated by the present methods. According to one embodiment, survival of hematopoietic stem cells is increased by at least about 2 fold, 3 fold, 4 fold, 5 fold, 6 fold, 7 fold, 8 fold, 9 fold or 10 fold as compared to hematopoietic stem cells not treated by the present methods. Measuring enhancement of hematopoietic stem cell survival is known to one of ordinary skill in the art and includes, for example, flow cytometric assay (FACS) staining e.g. for Annexin V.

According to one embodiment, the hematopoietic stem cells generated by the methods of some embodiments of the invention have an increased expansion potential while maintaining their differentiation potential as compared to hematopoietic stem cells not contacted with an agent capable of decreasing an activity or expression of CD74 and/or of MIF.

According to one embodiment, expansion of hematopoietic stem cells is increased by at least about 10%, 20%, 30%, 40%, 50%, 60%, 70%, 80%, 90%, 100%, 120%, 150% or 200% as compared to hematopoietic stem cells not treated by the present methods. According to one embodiment, expansion of hematopoietic stem cells is increased by at least about 2 fold, 3 fold, 4 fold, 5 fold, 6 fold, 7 fold, 8 fold, 9 fold or 10 fold as compared to hematopoietic stem cells not treated by the present methods. Measuring enhancement of hematopoietic stem cell expansion (e.g. self-renewal) is known to one of ordinary skill in the art and includes, for example, flow cytometric assay (FACS), Colony-forming unit (CFU) assay, competitive bone marrow chimera assay and serial transplantation assay.

As mentioned, expansion of hematopoietic stem cells occurs while maintaining their differentiation potential (i.e. the same level of differentiation as that of a naïve population of HSCs not treated by the presently taught methods) Accordingly, the hematopoietic stem cells treated by the methods of some embodiments of the invention are capable of differentiating into any myeloid or lymphoid lineages of blood cells, such as but not limited to the myeloid cells: monocytes, macrophages, neutrophils, basophils, eosinophils, erythrocytes, dendritic cells, megakaryocytes and platelets; and the lymphoid cells: T cells, B cells, and natural killer cells (as discussed in detail hereinabove).

The methods of some embodiments of the invention are affected by contacting the hematopoietic stem cells with an agent capable of decreasing an activity or expression of CD74 and/or of MIF.

As used herein, the term "CD74" refers to an expressed isoform of the CD74 gene. According to an embodiment, the CD74 is human CD74. According to one embodiment, CD74 is set forth in Accession Numbers NP_001020329.1, NP_001020330.1, NP_004346.1, XP_016865578.1 and XP_016865579.1.

According to one embodiment, decreasing an activity or expression of CD74 relates to all CD74 isoforms.

According to one embodiment, CD74 serves as cell surface receptor for the cytokine macrophage migration inhibitory factor (MIF).

According to one embodiment, decreasing an activity or expression of CD74 relates to the extracellular portion of CD74, for instance, to the MIF binding domain in CD74 (e.g. residues 109-149 of the CD74 extracellular domain as previously taught in Leng L, et al. MIF signal transduction initiated by binding to CD74 (2003) J Exp Med. 197(11): 1467-76).

The term "MIF" as used herein refers to the macrophage migration inhibitory factor or active fragments thereof. An active fragment of MIF may comprise a fragment or a portion of the MIF protein capable of binding and activating CD74.

Binding of MIF to CD74 can be determined by any binding assay such as "pull down" or "immunoprecipitation" assays. Additionally, binding of MIF to CD74 can be analyzed by Real-time Binding Analysis of MIF to CD74 (BIAcore Analysis) as discussed in Leng L, et al. MIF signal transduction initiated by binding to CD74 (2003) *J Exp Med.* 197(11):1467-76, incorporated herein by reference. Additional binding assays are described in Pollard, A Guide to Simple and Informative Binding Assays, Mol Biol Cell. (2010) 21(23): 4061-4067, incorporated herein by reference.

Activation of CD74 can be determined, for example, by upregulation of CXCR4 or bcl2, by phosphorylation of a factor down-stream of CD74 (e.g. ERK1/2, JNK, PI3K, SAPK MAP kinase, Syk tyrosine kinase and Akt) or by production of pro-inflammatory cytokines (e.g. TNF-α, IL-1, and $PGE_2$). Any method known in the art may be employed, e.g. Western Blot and ELISA, respectively.

According to an embodiment, MIF is human MIF, a product of the human MIF gene. According to one embodiment, MIF is set forth in Accession Number NP_002406.1.

According to another aspect of the present invention, there is provided a method of increasing mobilization of hematopoietic stem cells from the bone marrow to the peripheral blood in a healthy subject, the method comprising administering to the subject an agent capable of decreasing an activity or expression of CD74 and/or of macrophage migration inhibitory factor (MIF), thereby increasing mobilization of hematopoietic stem cells.

According to another aspect of the present invention, there is provided a therapeutically effective amount of an agent capable of decreasing an activity or expression of CD74 and/or of macrophage migration inhibitory factor (MIF) for use in increasing mobilization of hematopoietic stem cells from the bone marrow to the peripheral blood in a healthy subject.

As used herein the term "mobilization" refers to the release of hematopoietic precursors (e.g., hematopoietic stem cells) from bone marrow into peripheral blood circulation.

As used herein "increasing mobilization" refers to inducing mobilization of peripheral blood precursor cells, to elevate circulating levels of HSCs, or to enhance or facilitate hematopoietic reconstitution or engraftment, in a subject in need thereof.

According to one embodiment, mobilization of hematopoietic stem cells is increased by at least about 10%, 20%, 30%, 40%, 50%, 60%, 70%, 80%, 90%, 100%, 120%, 150% or 200% as compared to mobilization in the absence of the present agents. According to one embodiment, mobilization of hematopoietic stem cells is increased by at least about 2 fold, 3 fold, 4 fold, 5 fold, 6 fold, 7 fold, 8 fold, 9 fold or 10 fold as compared to mobilization in the absence of the present agents. Measuring enhancement of hematopoietic stem cell mobilization is known to one of ordinary skill in the art and is discussed in detail below.

As used herein the term "subject" refers to a mammalian subject e.g., a human subject, of any gender or age. The subject may be a healthy subject who serves as a donor for hematopoietic stem cell transplantation (e.g. also referred to as a 'donor subject'). Alternatively, the subject may suffer from a disease or condition (e.g. malignant disease or non-malignant disease such as an immune deficiency) and hence is in need of stem cell mobilization or stem cell transplantation (i.e., autologous; or from a donor i.e., non-autologous i.e., syngeneic, allogeneic or xenogeneic). In the latter case the subject is a recipient in need of a stem cell transplant.

The term "healthy subject" as used herein refers to a subject who has not been diagnosed with a disease or disorder amenable to treatment by hematopoietic stem cell transplantation. According to a specific embodiment, the healthy subject does not suffer from a hematopoietic disorder or malignancy.

As used herein the phrase "decreasing an activity or expression" refers to downregulating the expression of a protein (e.g. CD74 and/or MIF) at the genomic (e.g. homologous recombination and site specific endonucleases) and/or the transcript level using a variety of molecules which interfere with transcription and/or translation (e.g., RNA silencing agents) or downregulating the activity or expression on the protein level (e.g., using aptamers, small molecules and inhibitory peptides, antagonists, enzymes that cleave the polypeptide, antibodies and the like).

For the same culture conditions the activity or expression is generally expressed in comparison to the activity or expression in a cell of the same species but not contacted with the agent or contacted with a vehicle control, also referred to as control.

According to one embodiment, downregulation of the activity or expression of CD74 and/or MIF is by at least about 10%, 20%, 30%, 40%, 50%, 60%, 70%, 80%, 90% or 100% as compared to an activity or expression of CD74 and/or MIF not contacted with the agent of some embodiments of the invention.

Downregulation of an activity or expression may be either transient or permanent.

According to a specific embodiment, down regulating expression refers to the absence of mRNA and/or protein, as detected by RT-PCR or Western blot, respectively.

According to other specific embodiments, down regulating expression refers to a decrease in the level of mRNA and/or protein, as detected by RT-PCR or Western blot, respectively. The reduction may be by at least a 10%, at least 20%, at least 30%, at least 40%, at least 50%, at least 60%, at least 70%, at least 80%, at least 90%, at least 95% or at least 99% reduction.

According to a specific embodiment, down regulating activity refers to the absence of CD74 activity (e.g. lack of activation of factors in the CD74 cell signaling pathway, such as downregulation of CXCR4) and/or MIF activity (e.g. inhibition of binding of MIF to CD74), as detected e.g. by ELISA or Western Blot.

According to other specific embodiments, down regulating activity refers to a decrease in the level of CD74 activity (e.g. reduction in the activation of factors in the CD74 cell signaling pathway, such as downregulation of CXCR4) and/or MIF activity (e.g. reduction of binding of MIF to CD74), as detected e.g. by ELISA or Western Blot. The reduction may be by at least a 10%, at least 20%, at least 30%, at least 40%, at least 50%, at least 60%, at least 70%, at least 80%, at least 90%, at least 95% or at least 99% reduction.

Non-limiting examples of agents capable of down regulating CD74 and/or MIF expression are described in details hereinbelow.

Down-Regulation at the Nucleic Acid Level

Down-regulation at the nucleic acid level is typically effected using a nucleic acid agent, having a nucleic acid backbone, DNA, RNA, mimetics thereof or a combination of same (also referred to herein as a polynucleotide agent). The nucleic acid agent may be encoded from a DNA molecule or provided to the cell per se.

According to one embodiment, for downregulation of CD74, the agent is typically administered to hematopoietic stem cells expressing the CD74. For downregulation of MIF, the agent may be administered to any cell capable of producing and secreting MIF, e.g. immune cells, such as lymphocytes, macrophages, dendritic cells, neutrophils and pituitary cells.

Thus, downregulation of CD74 and/or MIF can be achieved by RNA silencing. As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene. RNA silencing has been observed in many types of organisms, including plants, animals, and fungi.

As used herein, the term "RNA silencing agent" refers to an RNA which is capable of specifically inhibiting or "silencing" the expression of a target gene. In certain embodiments, the RNA silencing agent is capable of preventing complete processing (e.g., the full translation and/or expression) of an mRNA molecule through a post-transcriptional silencing mechanism. RNA silencing agents include non-coding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs.

In one embodiment, the RNA silencing agent is capable of inducing RNA interference.

In another embodiment, the RNA silencing agent is capable of mediating translational repression.

According to an embodiment of the invention, the RNA silencing agent is specific to the target RNA (e.g., CD74 and/or MIF) and does not cross inhibit or silence other targets or a splice variant which exhibits 99% or less global homology to the target gene, e.g., less than 98%, 97%, 96%, 95%, 94%, 93%, 92%, 91%, 90%, 89%, 88%, 87%, 86%, 85%, 84%, 83%, 82%, 81% global homology to the target gene; as determined by PCR, Western blot, Immunohistochemistry and/or flow cytometry.

RNA interference refers to the process of sequence-specific post-transcriptional gene silencing in animals mediated by short interfering RNAs (siRNAs).

Following is a detailed description on RNA silencing agents that can be used according to specific embodiments of the present invention.

DsRNA, siRNA and shRNA—The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

Accordingly, some embodiments of the invention contemplate use of dsRNA to downregulate protein expression from mRNA.

According to one embodiment dsRNA longer than 30 bp are used. Various studies demonstrate that long dsRNAs can be used to silence gene expression without inducing the stress response or causing significant off-target effects—see for example [Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl Acad. Sci. USA. 2002; 99:1443-1448; Tran N., et al., FEBS Lett. 2004; 573:127-134].

According to some embodiments of the invention, dsRNA is provided in cells where the interferon pathway is not activated, see for example Billy et al., PNAS 2001, Vol 98, pages 14428-14433. and Diallo et al, Oligonucleotides, Oct. 1, 2003, 13(5): 381-392. doi: 10.1089/154545703322617069.

According to an embodiment of the invention, the long dsRNA are specifically designed not to induce the interferon and PKR pathways for down-regulating gene expression. For example, Shinagwa and Ishii [Genes & Dev. 17 (11): 1340-1345, 2003] have developed a vector, named pDECAP, to express long double-strand RNA from an RNA polymerase II (Pol II) promoter. Because the transcripts from pDECAP lack both the 5'-cap structure and the 3'-poly (A) tail that facilitate ds-RNA export to the cytoplasm, long ds-RNA from pDECAP does not induce the interferon response.

Another method of evading the interferon and PKR pathways in mammalian systems is by introduction of small inhibitory RNAs (siRNAs) either via transfection or endogenous expression.

The term "siRNA" refers to small inhibitory RNA duplexes (generally between 18-30 base pairs) that induce the RNA interference (RNAi) pathway. Typically, siRNAs are chemically synthesized as 21 mers with a central 19 bp duplex region and symmetric 2-base 3'-overhangs on the termini, although it has been recently described that chemically synthesized RNA duplexes of 25-30 base length can have as much as a 100-fold increase in potency compared with 21 mers at the same location. The observed increased potency obtained using longer RNAs in triggering RNAi is suggested to result from providing Dicer with a substrate (27 mer) instead of a product (21 mer) and that this improves the rate or efficiency of entry of the siRNA duplex into RISC.

It has been found that position of the 3'-overhang influences potency of an siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., a siRNA) may be connected to form a hairpin or stem-loop structure (e.g., a shRNA). Thus, as mentioned, the RNA silencing agent of some embodiments of the invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-CAAGAGA-3' and 5'-UUACAA-3' (International Patent Application Nos. WO2013126963 and WO2014107763). It will be recognized by one of skill in the art that the resulting single chain oligonucleotide forms a stem-loop or hairpin structure comprising a double-stranded region capable of interacting with the RNAi machinery.

Synthesis of RNA silencing agents suitable for use with some embodiments of the invention can be effected as follows. First, the CD74 and/or MIF mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl Chem Biochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (www(dot)ambion(dot)com/techlib/tn/91/912(dot)html).

Second, potential target sites are compared to an appropriate genomic database (e.g., human, mouse, rat etc.) using any sequence alignment software, such as the BLAST software available from the NCBI server (www(dot)ncbi(dot)nlm(dot)nih(dot)gov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably includes the same nucleotide composition as the siRNAs but lack significant homology to the genome. Thus, a scrambled nucleotide sequence of the siRNA is preferably used, provided it does not display any significant homology to any other gene.

For example, suitable siRNAs directed against CD74 can be the siRNA commercially available from Origene or from Santa Cruz Biotechnology (SCBT).

For example, suitable siRNAs directed against MIF can be the siRNA commercially available from Origene or from Santa Cruz Biotechnology (SCBT).

It will be appreciated that, and as mentioned hereinabove, the RNA silencing agent of some embodiments of the invention need not be limited to those molecules containing only RNA, but further encompasses chemically-modified nucleotides and non-nucleotides.

miRNA and miRNA mimics—According to another embodiment the RNA silencing agent may be a miRNA.

The term "microRNA", "miRNA", and "miR" are synonymous and refer to a collection of non-coding single-stranded RNA molecules of about 19-28 nucleotides in length, which regulate gene expression. miRNAs are found in a wide range of organisms (viruses.fwdarw.humans) and have been shown to play a role in development, homeostasis, and disease etiology.

Below is a brief description of the mechanism of miRNA activity.

Genes coding for miRNAs are transcribed leading to production of an miRNA precursor known as the pri-miRNA. The pri-miRNA is typically part of a polycistronic RNA comprising multiple pri-miRNAs. The pri-miRNA may form a hairpin with a stem and loop. The stem may comprise mismatched bases.

The hairpin structure of the pri-miRNA is recognized by Drosha, which is an RNase III endonuclease. Drosha typically recognizes terminal loops in the pri-miRNA and cleaves approximately two helical turns into the stem to produce a 60-70 nucleotide precursor known as the pre-miRNA. Drosha cleaves the pri-miRNA with a staggered cut typical of RNase III endonucleases yielding a pre-miRNA stem loop with a 5' phosphate and ~2 nucleotide 3' overhang. It is estimated that approximately one helical turn of stem (~10 nucleotides) extending beyond the Drosha cleavage site is essential for efficient processing. The pre-miRNA is then actively transported from the nucleus to the cytoplasm by Ran-GTP and the export receptor Ex-portin-5.

The double-stranded stem of the pre-miRNA is then recognized by Dicer, which is also an RNase III endonuclease. Dicer may also recognize the 5' phosphate and 3' overhang at the base of the stem loop. Dicer then cleaves off the terminal loop two helical turns away from the base of the stem loop leaving an additional 5' phosphate and ~2 nucleotide 3' overhang. The resulting siRNA-like duplex, which may comprise mismatches, comprises the mature miRNA and a similar-sized fragment known as the miRNA*. The miRNA and miRNA* may be derived from opposing arms of the pri-miRNA and pre-miRNA. miRNA* sequences may be found in libraries of cloned miRNAs but typically at lower frequency than the miRNAs.

Although initially present as a double-stranded species with miRNA*, the miRNA eventually becomes incorporated as a single-stranded RNA into a ribonucleoprotein complex known as the RNA-induced silencing complex (RISC). Various proteins can form the RISC, which can lead to variability in specificity for miRNA/miRNA* duplexes, binding site of the target gene, activity of miRNA (repress or activate), and which strand of the miRNA/miRNA* duplex is loaded in to the RISC.

When the miRNA strand of the miRNA:miRNA* duplex is loaded into the RISC, the miRNA* is removed and degraded. The strand of the miRNA:miRNA* duplex that is loaded into the RISC is the strand whose 5' end is less tightly paired. In cases where both ends of the miRNA:miRNA* have roughly equivalent 5' pairing, both miRNA and miRNA* may have gene silencing activity.

The RISC identifies target nucleic acids based on high levels of complementarity between the miRNA and the mRNA, especially by nucleotides 2-7 of the miRNA.

A number of studies have looked at the base-pairing requirement between miRNA and its mRNA target for achieving efficient inhibition of translation (reviewed by Bartel 2004, Cell 116-281). In mammalian cells, the first 8 nucleotides of the miRNA may be important (Doench & Sharp 2004 GenesDev 2004-504). However, other parts of the microRNA may also participate in mRNA binding. Moreover, sufficient base pairing at the 3' can compensate for insufficient pairing at the 5' (Brennecke et al, 2005 PLoS 3-e85). Computation studies, analyzing miRNA binding on whole genomes have suggested a specific role for bases 2-7 at the 5' of the miRNA in target binding but the role of the first nucleotide, found usually to be "A" was also recognized (Lewis et at 2005 Cell 120-15). Similarly, nucleotides 1-7 or 2-8 were used to identify and validate targets by Krek et al. (2005, Nat Genet 37-495).

The target sites in the mRNA may be in the 5' UTR, the 3' UTR or in the coding region. Interestingly, multiple miRNAs may regulate the same mRNA target by recognizing the same or multiple sites. The presence of multiple miRNA binding sites in most genetically identified targets may indicate that the cooperative action of multiple RISCs provides the most efficient translational inhibition.

miRNAs may direct the RISC to downregulate gene expression by either of two mechanisms: mRNA cleavage or translational repression. The miRNA may specify cleavage of the mRNA if the mRNA has a certain degree of complementarity to the miRNA. When a miRNA guides cleavage, the cut is typically between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity between the miRNA and binding site.

It should be noted that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA*may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

The term "microRNA mimic" or "miRNA mimic" refers to synthetic non-coding RNAs that are capable of entering the RNAi pathway and regulating gene expression. miRNA mimics imitate the function of endogenous miRNAs and can be designed as mature, double stranded molecules or mimic precursors (e.g., or pre-miRNAs). miRNA mimics can be comprised of modified or unmodified RNA, DNA, RNA-DNA hybrids, or alternative nucleic acid chemistries (e.g., LNAs or 2'-O,4'-C-ethylene-bridged nucleic acids (ENA)). For mature, double stranded miRNA mimics, the length of the duplex region can vary between 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the pre-miRNA. The sequence of the miRNA may also be the last 13-33 nucleotides of the pre-miRNA.

Preparation of miRNAs mimics can be effected by any method known in the art such as chemical synthesis or recombinant methods.

It will be appreciated from the description provided herein above that contacting cells with a miRNA may be effected by transfecting the cells with e.g. the mature double stranded miRNA, the pre-miRNA or the pri-miRNA.

The pre-miRNA sequence may comprise from 45-90, 60-80 or 60-70 nucleotides.

The pri-miRNA sequence may comprise from 45-30,000, 50-25,000, 100-20,000, 1,000-1,500 or 80-100 nucleotides.

For example, suitable miRNAs directed against CD74 can be the miRNA available from Origene.

For example, suitable miRNAs directed against MIF can be the miRNA available from Origene or miRNAs that target MIF: hsa-mir-451a (Accession No. MIRT000046), hsa-mir-744-5p (Accession No. MIRT037678), hsa-mir-769-5p (Accession No. MIRT039145) or hsa-mir-320a (Accession No. MIRT044670).

Antisense—Antisense is a single stranded RNA designed to prevent or inhibit expression of a gene by specifically hybridizing to its mRNA. Downregulation of a CD74 and/or MIF can be effected using an antisense polynucleotide capable of specifically hybridizing with an mRNA transcript encoding CD74 and/or MIF.

Design of antisense molecules which can be used to efficiently downregulate a CD74 and/or MIF must be effected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

The prior art teaches of a number of delivery strategies which can be used to efficiently deliver oligonucleotides into a wide variety of cell types [see, for example, Jääskeläinen et al. Cell Mol Biol Lett. (2002) 7(2):236-7; Gait, Cell Mol Life Sci. (2003) 60(5):844-53; Martino et al. J Biomed Biotechnol. (2009) 2009: 410260; Grijalvo et al. Expert Opin Ther Pat. (2014) 24(7):801-19; Falzarano et al, Nucleic Acid Ther. (2014) 24(1):87-100; Shilakari et al. Biomed Res Int. (2014) 2014: 526391; Prakash et al. Nucleic Acids Res. (2014) 42(13):8796-807 and Asseline et al. J Gene Med. (2014) 16(7-8):157-65].

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. Biotechnol Bioeng 65: 1-9 (1999)]. Such algorithms have been successfully used to implement an antisense approach in cells.

In addition, several approaches for designing and predicting efficiency of specific oligonucleotides using an in vitro system were also published (Matveeva et al., Nature Biotechnology 16: 1374-1375 (1998)].

Thus, the generation of highly accurate antisense design algorithms and a wide variety of oligonucleotide delivery systems, enable an ordinarily skilled artisan to design and implement antisense approaches suitable for downregulating expression of known sequences without having to resort to undue trial and error experimentation.

Nucleic acid agents can also operate at the DNA level as summarized infra.

Downregulation of CD74 and/or MIF can also be achieved by inactivating the gene (e.g., CD74 and/or MIF) via introducing targeted mutations involving loss-of-function alterations (e.g. point mutations, deletions and insertions) in the gene structure.

As used herein, the phrase "loss-of-function alterations" refers to any mutation in the DNA sequence of a gene (e.g., CD74 and/or MIF) which results in downregulation of the expression level and/or activity of the expressed product, i.e., the mRNA transcript and/or the translated protein. Non-limiting examples of such loss-of-function alterations include a missense mutation, i.e., a mutation which changes an amino acid residue in the protein with another amino acid residue and thereby abolishes the enzymatic activity of the protein; a nonsense mutation, i.e., a mutation which introduces a stop codon in a protein, e.g., an early stop codon which results in a shorter protein devoid of the enzymatic activity; a frame-shift mutation, i.e., a mutation, usually, deletion or insertion of nucleic acid(s) which changes the reading frame of the protein, and may result in an early termination by introducing a stop codon into a reading frame (e.g., a truncated protein, devoid of the enzymatic activity), or in a longer amino acid sequence (e.g., a readthrough protein) which affects the secondary or tertiary structure of the protein and results in a non-functional protein, devoid of the enzymatic activity of the non-mutated polypeptide; a readthrough mutation due to a frame-shift mutation or a modified stop codon mutation (i.e., when the stop codon is mutated into an amino acid codon), with an abolished enzymatic activity; a promoter mutation, i.e., a mutation in a promoter sequence, usually 5' to the transcription start site of a gene, which results in down-regulation of a specific gene product; a regulatory mutation, i.e., a mutation in a region upstream or downstream, or within a gene, which affects the expression of the gene product; a deletion mutation, i.e., a mutation which deletes coding nucleic acids in a gene sequence and which may result in a frame-shift mutation or an in-frame mutation (within the coding sequence, deletion of one or more amino acid codons); an insertion mutation, i.e., a mutation which inserts coding or non-coding nucleic acids into a gene sequence, and which may result in a frame-shift mutation or an in-frame insertion of one or more amino acid codons; an inversion, i.e., a mutation which results in an inverted coding or non-coding sequence; a splice mutation i.e., a mutation which results in abnormal splicing or poor splicing; and a duplication mutation, i.e., a mutation which results in a duplicated coding or non-coding sequence, which can be in-frame or can cause a frame-shift.

According to specific embodiments loss-of-function alteration of a gene may comprise at least one allele of the gene.

The term "allele" as used herein, refers to any of one or more alternative forms of a gene locus, all of which alleles relate to a trait or characteristic. In a diploid cell or organism, the two alleles of a given gene occupy corresponding loci on a pair of homologous chromosomes.

According to other specific embodiments loss-of-function alteration of a gene comprises both alleles of the gene. In such instances the e.g. CD74 and/or MIF may be in a homozygous form or in a heterozygous form. According to this embodiment, homozygosity is a condition where both alleles at the e.g. CD74 and/or MIF locus are characterized by the same nucleotide sequence. Heterozygosity refers to different conditions of the gene at the e.g. CD74 and/or MIF locus.

Methods of introducing nucleic acid alterations to a gene of interest are well known in the art [see for example Menke D. Genesis (2013) 51: -618; Capecchi, Science (1989) 244:1288-1292; Santiago et al. Proc Natl Acad Sci USA (2008) 105:5809-5814; International Patent Application Nos. WO 2014085593, WO 2009071334 and WO 2011146121; U.S. Pat. Nos. 8,771,945, 8,586,526, 6,774,279 and UP Patent Application Publication Nos. 20030232410, 20050026157, US20060014264; the contents of which are incorporated by reference in their entireties] and include targeted homologous recombination, site specific recombinases, PB transposases and genome editing by engineered nucleases. Agents for introducing nucleic acid alterations to a gene of interest can be designed publically available sources or obtained commercially from Transposagen, Addgene and Sangamo Biosciences.

Following is a description of various exemplary methods used to introduce nucleic acid alterations to a gene of interest and agents for implementing same that can be used according to specific embodiments of the present invention.

Genome Editing using engineered endonucleases—this approach refers to a reverse genetics method using artificially engineered nucleases to cut and create specific double-stranded breaks at a desired location(s) in the genome, which are then repaired by cellular endogenous processes such as, homology directed repair (HDR) and non-homologous end-joining (NFfEJ). NFfEJ directly joins the DNA ends in a double-stranded break, while HDR utilizes a homologous sequence as a template for regenerating the missing DNA sequence at the break point. In order to introduce specific nucleotide modifications to the genomic DNA, a DNA repair template containing the desired sequence must be present during HDR. Genome editing cannot be performed using traditional restriction endonucleases since most restriction enzymes recognize a few base pairs on the DNA as their target and the probability is very high that the recognized base pair combination will be found in many locations across the genome resulting in multiple cuts not limited to a desired location. To overcome this challenge and create site-specific single- or double-stranded breaks, several distinct classes of nucleases have been discovered and bioengineered to date. These include the meganucleases, Zinc finger nucleases (ZFNs), transcription-activator like effector nucleases (TALENs) and CRISPR/Cas system.

Meganucleases—Meganucleases are commonly grouped into four families: the LAGLIDADG family, the GIY-YIG family, the His-Cys box family and the HNH family. These families are characterized by structural motifs, which affect catalytic activity and recognition sequence. For instance, members of the LAGLIDADG family are characterized by having either one or two copies of the conserved LAGLIDADG motif. The four families of meganucleases are widely separated from one another with respect to conserved structural elements and, consequently, DNA recognition sequence specificity and catalytic activity. Meganucleases are found commonly in microbial species and have the unique property of having very long recognition sequences (>14 bp) thus making them naturally very specific for cutting at a desired location. This can be exploited to make site-specific double-stranded breaks in genome editing. One of skill in the art can use these naturally occurring meganucleases, however the number of such naturally occurring meganucleases is limited. To overcome this challenge, mutagenesis and high throughput screening methods have been used to create meganuclease variants that recognize unique sequences. For example, various meganucleases have been fused to create hybrid enzymes that recognize a new sequence. Alternatively, DNA interacting amino acids of the meganuclease can be altered to design sequence specific meganucleases (see e.g., U.S. Pat. No. 8,021,867). Meganucleases can be designed using the methods described in e.g., Certo, M T et al. Nature Methods (2012) 9:073-975; U.S. Pat. Nos. 8,304,222; 8,021,867; 8,119,381; 8,124,369; 8,129,134; 8,133,697; 8,143,015; 8,143,016; 8, 148,098; or 8, 163,514, the contents of each are incorporated herein by reference in their entirety.

Alternatively, meganucleases with site specific cutting characteristics can be obtained using commercially available technologies e.g., Precision Biosciences' Directed Nuclease Editor™ genome editing technology.

ZFNs and TALENs—Two distinct classes of engineered nucleases, zinc-finger nucleases (ZFNs) and transcription activator-like effector nucleases (TALENs), have both proven to be effective at producing targeted double-stranded breaks (Christian et al., 2010; Kim et al., 1996; Li et al., 2011; Mahfouz et al., 2011; Miller et al., 2010).

Basically, ZFNs and TALENs restriction endonuclease technology utilizes a non-specific DNA cutting enzyme which is linked to a specific DNA binding domain (either a series of zinc finger domains or TALE repeats, respectively). Typically a restriction enzyme whose DNA recognition site and cleaving site are separate from each other is selected. The cleaving portion is separated and then linked to a DNA binding domain, thereby yielding an endonuclease with very high specificity for a desired sequence. An exemplary restriction enzyme with such properties is Fok1. Additionally Fok1 has the advantage of requiring dimerization to have nuclease activity and this means the specificity increases dramatically as each nuclease partner recognizes a unique DNA sequence. To enhance this effect, Fok1 nucleases have been engineered that can only function as heterodimers and have increased catalytic activity. The heterodimer functioning nucleases avoid the possibility of unwanted homodimer activity and thus increase specificity of the double-stranded break.

Thus, for example to target a specific site, ZFNs and TALENs are constructed as nuclease pairs, with each member of the pair designed to bind adjacent sequences at the targeted site. Upon transient expression in cells, the nucleases bind to their target sites and the FokI domains heterodimerize to create a double-stranded break. Repair of these double-stranded breaks through the non-homologous end-joining (NHEJ) pathway most often results in small deletions or small sequence insertions. Since each repair made by NHEJ is unique, the use of a single nuclease pair can produce an allelic series with a range of different deletions at the target site. The deletions typically range anywhere from a few base pairs to a few hundred base pairs in length, but larger deletions have successfully been generated in cell culture by using two pairs of nucleases simultaneously (Carlson et al., 2012; Lee et al., 2010). In addition, when a fragment of DNA with homology to the targeted region is introduced in conjunction with the nuclease pair, the double-stranded break can be repaired via homology directed repair to generate specific modifications (Li et al., 2011; Miller et al., 2010; Urnov et al., 2005).

Although the nuclease portions of both ZFNs and TALENs have similar properties, the difference between these engineered nucleases is in their DNA recognition peptide. ZFNs rely on Cys2-His2 zinc fingers and TALENs on TALEs. Both of these DNA recognizing peptide domains have the characteristic that they are naturally found in combinations in their proteins. Cys2-His2 Zinc fingers typically found in repeats that are 3 bp apart and are found in diverse combinations in a variety of nucleic acid interacting proteins. TALEs on the other hand are found in repeats with a one-to-one recognition ratio between the amino acids and the recognized nucleotide pairs. Because both zinc fingers and TALEs happen in repeated patterns, different combinations can be tried to create a wide variety of sequence specificities. Approaches for making site-specific zinc finger endonucleases include, e.g., modular assembly (where Zinc fingers correlated with a triplet sequence are attached in a row to cover the required sequence), OPEN (low-stringency selection of peptide domains vs. triplet nucleotides followed by high-stringency selections of peptide combination vs. the final target in bacterial systems), and bacterial one-hybrid screening of zinc finger libraries, among others. ZFNs can also be designed and obtained commercially from e.g., Sangamo Biosciences™ (Richmond, CA).

Method for designing and obtaining TALENs are described in e.g. Reyon et al. Nature Biotechnology 2012 May; 30(5):460-5; Miller et al. Nat Biotechnol. (2011) 29: 143-148; Cermak et al. Nucleic Acids Research (2011) 39 (12): e82 and Zhang et al. Nature Biotechnology (2011) 29 (2): 149-53. A recently developed web-based program named Mojo Hand was introduced by Mayo Clinic for designing TAL and TALEN constructs for genome editing applications (can be accessed through www(dot)talendesign (dot)org). TALEN can also be designed and obtained commercially from e.g., Sangamo Biosciences™ (Richmond, CA).

CRISPR-Cas system—Many bacteria and archea contain endogenous RNA-based adaptive immune systems that can degrade nucleic acids of invading phages and plasmids. These systems consist of clustered regularly interspaced short palindromic repeat (CRISPR) genes that produce RNA components and CRISPR associated (Cas) genes that encode protein components. The CRISPR RNAs (crRNAs) contain short stretches of homology to specific viruses and plasmids and act as guides to direct Cas nucleases to degrade the complementary nucleic acids of the corresponding pathogen. Studies of the type II CRISPR/Cas system of *Streptococcus pyogenes* have shown that three components form an RNA/protein complex and together are sufficient for sequence-specific nuclease activity: the Cas9 nuclease, a crRNA containing 20 base pairs of homology to the target sequence, and a trans-activating crRNA (tracrRNA) (Jinek et al. *Science* (2012) 337: 816-821). It was further demonstrated that a synthetic chimeric guide RNA (gRNA) composed of a fusion between crRNA and tracrRNA could direct Cas9 to cleave DNA targets that are complementary to the crRNA in vitro. It was also demonstrated that transient expression of Cas9 in conjunction with synthetic gRNAs can be used to produce targeted double-stranded brakes in a variety of different species (Cho et al., 2013; Cong et al., 2013; DiCarlo et al., 2013; Hwang et al., 2013a,b; Jinek et al., 2013; Mali et al., 2013).

The CRIPSR/Cas system for genome editing contains two distinct components: a gRNA and an endonuclease e.g. Cas9.

The gRNA is typically a 20 nucleotide sequence encoding a combination of the target homologous sequence (crRNA) and the endogenous bacterial RNA that links the crRNA to the Cas9 nuclease (tracrRNA) in a single chimeric transcript. The gRNA/Cas9 complex is recruited to the target sequence by the base-pairing between the gRNA sequence and the complement genomic DNA. For successful binding of Cas9, the genomic target sequence must also contain the correct Protospacer Adjacent Motif (PAM) sequence immediately following the target sequence. The binding of the gRNA/Cas9 complex localizes the Cas9 to the genomic target sequence so that the Cas9 can cut both strands of the DNA causing a double-strand break. Just as with ZFNs and TALENs, the double-stranded brakes produced by CRISPR/Cas can undergo homologous recombination or NHEJ.

The Cas9 nuclease has two functional domains: RuvC and HNH, each cutting a different DNA strand. When both of these domains are active, the Cas9 causes double strand breaks in the genomic DNA.

A significant advantage of CRISPR/Cas is that the high efficiency of this system coupled with the ability to easily create synthetic gRNAs enables multiple genes to be targeted simultaneously. In addition, the majority of cells carrying the mutation present biallelic mutations in the targeted genes.

However, apparent flexibility in the base-pairing interactions between the gRNA sequence and the genomic DNA target sequence allows imperfect matches to the target sequence to be cut by Cas9.

Modified versions of the Cas9 enzyme containing a single inactive catalytic domain, either RuvC− or HNH−, are called 'nickases'. With only one active nuclease domain, the Cas9 nickase cuts only one strand of the target DNA, creating a single-strand break or 'nick'. A single-strand break, or nick, is normally quickly repaired through the HDR pathway, using the intact complementary DNA strand as the template. However, two proximal, opposite strand nicks introduced by a Cas9 nickase are treated as a double-strand break, in what is often referred to as a 'double nick' CRISPR system. A double-nick can be repaired by either NHEJ or HDR depending on the desired effect on the gene target. Thus, if specificity and reduced off-target effects are crucial, using the Cas9 nickase to create a double-nick by designing two gRNAs with target sequences in close proximity and on opposite strands of the genomic DNA would decrease off-target effect as either gRNA alone will result in nicks that will not change the genomic DNA.

Modified versions of the Cas9 enzyme containing two inactive catalytic domains (dead Cas9, or dCas9) have no nuclease activity while still able to bind to DNA based on gRNA specificity. The dCas9 can be utilized as a platform for DNA transcriptional regulators to activate or repress gene expression by fusing the inactive enzyme to known regulatory domains. For example, the binding of dCas9 alone to a target sequence in genomic DNA can interfere with gene transcription.

There are a number of publically available tools available to help choose and/or design target sequences as well as lists of bioinformatically determined unique gRNAs for different genes in different species such as the Feng Zhang lab's Target Finder, the Michael Boutros lab's Target Finder (E-CRISP), the RGEN Tools: Cas-OFFinder, the CasFinder: Flexible algorithm for identifying specific Cas9 targets in genomes and the CRISPR Optimal Target Finder.

Non-limiting examples of a gRNA that can be used in the present invention for CD74 are commercially available from GenScript, Santa Cruz Biotechnology (SCBT), Applied Biological Materials or OriGene.

Non-limiting examples of a gRNA that can be used in the present invention for MIF are commercially available from GenScript, Santa Cruz Biotechnology (SCBT), Applied Biological Materials or OriGene.

In order to use the CRISPR system, both gRNA and Cas9 should be expressed in a target cell. The insertion vector can contain both cassettes on a single plasmid or the cassettes are expressed from two separate plasmids. CRISPR plasmids are commercially available such as the px330 plasmid from Addgene.

"Hit and run" or "in-out"—involves a two-step recombination procedure. In the first step, an insertion-type vector containing a dual positive/negative selectable marker cassette is used to introduce the desired sequence alteration. The insertion vector contains a single continuous region of homology to the targeted locus and is modified to carry the mutation of interest. This targeting construct is linearized with a restriction enzyme at a one site within the region of homology, electroporated into the cells, and positive selection is performed to isolate homologous recombinants. These homologous recombinants contain a local duplication that is separated by intervening vector sequence, including the selection cassette. In the second step, targeted clones are subjected to negative selection to identify cells that have lost the selection cassette via intrachromosomal recombination between the duplicated sequences. The local recombination event removes the duplication and, depending on the site of recombination, the allele either retains the introduced mutation or reverts to wild type. The end result is the introduction of the desired modification without the retention of any exogenous sequences.

The "double-replacement" or "tag and exchange" strategy—involves a two-step selection procedure similar to the hit and run approach, but requires the use of two different targeting constructs. In the first step, a standard targeting vector with 3' and 5' homology arms is used to insert a dual positive/negative selectable cassette near the location where the mutation is to be introduced. After electroporation and positive selection, homologously targeted clones are identified. Next, a second targeting vector that contains a region of homology with the desired mutation is electroporated into targeted clones, and negative selection is applied to remove the selection cassette and introduce the mutation. The final allele contains the desired mutation while eliminating unwanted exogenous sequences.

Site-Specific Recombinases—The Cre recombinase derived from the P1 bacteriophage and Flp recombinase derived from the yeast *Saccharomyces cerevisiae* are site-specific DNA recombinases each recognizing a unique 34 base pair DNA sequence (termed "Lox" and "FRT", respectively) and sequences that are flanked with either Lox sites or FRT sites can be readily removed via site-specific recombination upon expression of Cre or Flp recombinase, respectively. For example, the Lox sequence is composed of an asymmetric eight base pair spacer region flanked by 13 base pair inverted repeats. Cre recombines the 34 base pair lox DNA sequence by binding to the 13 base pair inverted repeats and catalyzing strand cleavage and religation within the spacer region. The staggered DNA cuts made by Cre in the spacer region are separated by 6 base pairs to give an overlap region that acts as a homology sensor to ensure that only recombination sites having the same overlap region recombine.

Basically, the site specific recombinase system offers means for the removal of selection cassettes after homologous recombination. This system also allows for the generation of conditional altered alleles that can be inactivated or activated in a temporal or tissue-specific manner. Of note, the Cre and Flp recombinases leave behind a Lox or FRT "scar" of 34 base pairs. The Lox or FRT sites that remain are typically left behind in an intron or 3' UTR of the modified locus, and current evidence suggests that these sites usually do not interfere significantly with gene function.

Thus, Cre/Lox and Flp/FRT recombination involves introduction of a targeting vector with 3' and 5' homology arms containing the mutation of interest, two Lox or FRT sequences and typically a selectable cassette placed between the two Lox or FRT sequences. Positive selection is applied and homologous recombinants that contain targeted mutation are identified. Transient expression of Cre or Flp in conjunction with negative selection results in the excision of the selection cassette and selects for cells where the cassette has been lost. The final targeted allele contains the Lox or FRT scar of exogenous sequences.

Transposases—As used herein, the term "transposase" refers to an enzyme that binds to the ends of a transposon and catalyzes the movement of the transposon to another part of the genome.

As used herein the term "transposon" refers to a mobile genetic element comprising a nucleotide sequence which can move around to different positions within the genome of a single cell. In the process the transposon can cause mutations and/or change the amount of a DNA in the genome of the cell.

A number of transposon systems that are able to also transpose in cells e.g. vertebrates have been isolated or designed, such as Sleeping Beauty [Izsvik and Ivics Molecular Therapy (2004) 9, 147-156], piggyBac [Wilson et al. Molecular Therapy (2007) 15, 139-145], Tol2 [Kawakami et al. PNAS (2000) 97 (21): 11403-11408] or Frog Prince [Miskey et al. Nucleic Acids Res. Dec. 1, (2003) 31(23): 6873-6881]. Generally, DNA transposons translocate from one DNA site to another in a simple, cut-and-paste manner. Each of these elements has their own advantages, for example, Sleeping Beauty is particularly useful in region-specific mutagenesis, whereas Tol2 has the highest tendency to integrate into expressed genes. Hyperactive systems are available for Sleeping Beauty and piggyBac. Most importantly, these transposons have distinct target site preferences, and can therefore introduce sequence alterations in overlapping, but distinct sets of genes. Therefore, to achieve the best possible coverage of genes, the use of more than one element is particularly preferred. The basic mechanism is shared between the different transposases therefore we will describe piggyBac (PB) as an example.

PB is a 2.5 kb insect transposon originally isolated from the cabbage looper moth, *Trichoplusia ni*. The PB transposon consists of asymmetric terminal repeat sequences that flank a transposase, PBase. PBase recognizes the terminal repeats and induces transposition via a "cut-and-paste" based mechanism, and preferentially transposes into the host genome at the tetranucleotide sequence TTAA. Upon insertion, the TTAA target site is duplicated such that the PB transposon is flanked by this tetranucleotide sequence. When mobilized, PB typically excises itself precisely to reestablish a single TTAA site, thereby restoring the host sequence to its pretransposon state. After excision, PB can transpose into a new location or be permanently lost from the genome.

Typically, the transposase system offers an alternative means for the removal of selection cassettes after homologous recombination quit similar to the use Cre/Lox or Flp/FRT. Thus, for example, the PB transposase system involves introduction of a targeting vector with 3' and 5' homology arms containing the mutation of interest, two PB terminal repeat sequences at the site of an endogenous TTAA sequence and a selection cassette placed between PB terminal repeat sequences. Positive selection is applied and homologous recombinants that contain targeted mutation are identified. Transient expression of PBase removes in conjunction with negative selection results in the excision of the selection cassette and selects for cells where the cassette has been lost. The final targeted allele contains the introduced mutation with no exogenous sequences.

For PB to be useful for the introduction of sequence alterations, there must be a native TTAA site in relatively close proximity to the location where a particular mutation is to be inserted.

Genome editing using recombinant adeno-associated virus (rAAV) platform—this genome-editing platform is based on rAAV vectors which enable insertion, deletion or substitution of DNA sequences in the genomes of live mammalian cells. The rAAV genome is a single-stranded deoxyribonucleic acid (ssDNA) molecule, either positive- or negative-sensed, which is about 4.7 kb long. These single-stranded DNA viral vectors have high transduction rates and have a unique property of stimulating endogenous homologous recombination in the absence of double-strand DNA breaks in the genome. One of skill in the art can design a rAAV vector to target a desired genomic locus and perform both gross and/or subtle endogenous gene alterations in a cell. rAAV genome editing has the advantage in that it targets a single allele and does not result in any off-target genomic alterations. rAAV genome editing technology is commercially available, for example, the rAAV GENESIS™ system from Horizon™ (Cambridge, UK).

It will be appreciated that the agent can be a mutagen that causes random mutations and the cells exhibiting downregulation of the expression level and/or activity of CD74 and/or MIF may be selected.

The mutagens may be, but are not limited to, genetic, chemical or radiation agents. For example, the mutagen may be ionizing radiation, such as, but not limited to, ultraviolet light, gamma rays or alpha particles. Other mutagens may include, but not be limited to, base analogs, which can cause copying errors; deaminating agents, such as nitrous acid; intercalating agents, such as ethidium bromide; alkylating agents, such as bromouracil; transposons; natural and synthetic alkaloids; bromine and derivatives thereof; sodium azide; psoralen (for example, combined with ultraviolet radiation). The mutagen may be a chemical mutagen such as, but not limited to, ICR191, 1,2,7,8-diepoxy-octane (DEO), 5-azaC, N-methyl-N-nitrosoguanidine (MNNG) or ethyl methane sulfonate (EMS).

Methods for qualifying efficacy and detecting sequence alteration are well known in the art and include, but not limited to, DNA sequencing, electrophoresis, an enzyme-based mismatch detection assay and a hybridization assay such as PCR, RT-PCR, RNase protection, in-situ hybridization, primer extension, Southern blot, Northern Blot and dot blot analysis.

Sequence alterations in a specific gene can also be determined at the protein level using e.g. chromatography, electrophoretic methods, immunodetection assays such as ELISA and western blot analysis and immunohistochemistry.

In addition, one ordinarily skilled in the art can readily design a knock-in/knock-out construct including positive and/or negative selection markers for efficiently selecting transformed cells that underwent a homologous recombination event with the construct. Positive selection provides a means to enrich the population of clones that have taken up foreign DNA. Non-limiting examples of such positive markers include glutamine synthetase, dihydrofolate reductase (DHFR), markers that confer antibiotic resistance, such as neomycin, hygromycin, puromycin, and blasticidin S resistance cassettes. Negative selection markers are necessary to select against random integrations and/or elimination of a marker sequence (e.g. positive marker). Non-limiting examples of such negative markers include the herpes simplex-thymidine kinase (HSV-TK) which converts ganciclovir (GCV) into a cytotoxic nucleoside analog, hypoxanthine phosphoribosyltransferase (HPRT) and adenine phosphoribosytransferase (ARPT).

Ribozymes

Another agent capable of downregulating a CD74 and/or MIF is a ribozyme molecule capable of specifically cleaving an mRNA transcript encoding a CD74 and/or MIF. Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., Clin Diagn Virol. 10:163-71 (1998)]. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—WEB home page).

DNAzymes

Another agent capable of downregulating a CD74 and/or MIF is a DNAzyme molecule capable of specifically cleaving an mRNA transcript or DNA sequence of the CD74 and/or MIF. DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl, Acad. Sci. USA 1997; 943:4262) A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine: pyrimidine junctions (Santoro, S. W. & Joyce, G. F. Proc. Natl, Acad. Sci. USA 199; for rev of DNAzymes see Khachigian, L M [Curr Opin Mol Ther 4:119-21 (2002)].

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al., 2002, Abstract 409, Ann Meeting Am. Soc. Gen. Ther. www(dot)asgt(dot)org). In another application, DNAzymes complementary to bcr-abl oncogenes were successful in inhibiting the oncogenes expression in leukemia cells, and lessening relapse rates in autologous bone marrow transplant in cases of CML and ALL.

TFO

An additional method of regulating the expression of an CD74 and/or MIF gene in cells is via triplex forming oligonuclotides (TFOs). Recent studies have shown that TFOs can be designed which can recognize and bind to polypurine/polypirimidine regions in double-stranded helical DNA in a sequence-specific manner. These recognition rules are outlined by Maher III, L. J., et al., Science, 1989; 245:725-730; Moser, H. E., et al., Science, 1987; 238:645-630; Beal, P. A., et al, Science, 1992; 251:1360-1363; Cooney, M., et al., Science, 1988; 241:456-459; and Hogan, M. E., et al., EP Publication 375408. Modification of the oligonucleotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer, J Clin Invest 2003; 112:487-94).

In general, the triplex-forming oligonucleotide has the sequence correspondence:

```
oligo     3'--A    G    G    T
duplex    5'--A    G    C    T
duplex    3'--T    C    G    A
```

However, it has been shown that the A-AT and G-GC triplets have the greatest triple helical stability (Reither and Jeltsch, B M C Biochem, 2002, Sep. 12, Epub). The same authors have demonstrated that TFOs designed according to the A-AT and G-GC rule do not form non-specific triplexes, indicating that the triplex formation is indeed sequence specific.

Thus for any given sequence in the CD74 and/or MIF regulatory region a triplex forming sequence may be devised. Triplex-forming oligonucleotides preferably are at least 15, more preferably 25, still more preferably 30 or more nucleotides in length, up to 50 or 100 bp.

Transfection of cells (for example, via cationic liposomes) with TFOs, and formation of the triple helical structure with the target DNA induces steric and functional changes, blocking transcription initiation and elongation, allowing the introduction of desired sequence changes in the endogenous DNA and resulting in the specific downregulation of gene expression. Examples of such suppression of gene expression in cells treated with TFOs include knockout of episomal supFG1 and endogenous HPRT genes in mammalian cells (Vasquez et al., Nucl Acids Res. 1999; 27:1176-81, and Puri, et al, J Biol Chem, 2001; 276:28991-98), and the sequence- and target specific downregulation of expression of the Ets2 transcription factor, important in prostate cancer etiology (Carbone, et al, Nucl Acid Res. 2003; 31:833-43), and the pro-inflammatory ICAM-1 gene (Besch et al, J Biol Chem, 2002; 277:32473-79). In addition, Vuyisich and Beal have recently shown that sequence specific TFOs can bind to dsRNA, inhibiting activity of dsRNA-dependent enzymes such as RNA-dependent kinases (Vuyisich and Beal, Nuc. Acids Res 2000; 28:2369-74).

Additionally, TFOs designed according to the abovementioned principles can induce directed mutagenesis capable of effecting DNA repair, thus providing both downregulation and upregulation of expression of endogenous genes (Seidman and Glazer, J Clin Invest 2003; 112:487-94). Detailed description of the design, synthesis and administration of effective TFOs can be found in U.S. Patent Application Nos. 2003 017068 and 2003 0096980 to Froehler et al, and 2002 0128218 and 2002 0123476 to Emanuele et al, and U.S. Pat. No. 5,721,138 to Lawn.

Down-Regulation at the Polypeptide Level

According to specific embodiments the agent capable of downregulating a CD74 and/or MIF is an antibody or antibody fragment capable of specifically binding CD74 and/or MIF. Preferably, the antibody specifically binds at least one epitope of a CD74 and/or MIF.

As used herein, the term "epitope" refers to any antigenic determinant on an antigen to which the paratope of an antibody binds. Epitopic determinants usually consist of chemically active surface groupings of molecules such as amino acids or carbohydrate side chains and usually have specific three dimensional structural characteristics, as well as specific charge characteristics. Epitopic determinants usually consist of chemically active surface groupings of molecules such as amino acids or carbohydrate side chains and usually have specific three dimensional structural characteristics, as well as specific charge characteristics.

The term "antibody" as used in this invention includes intact molecules as well as functional fragments thereof (such as Fab, F(ab')2, Fv, scFv, dsFv, or single domain molecules such as VH and VL) that are capable of binding to an epitope of an antigen.

Suitable antibody fragments for practicing some embodiments of the invention include a complementarity-determining region (CDR) of an immunoglobulin light chain (referred to herein as "light chain"), a complementarity-determining region of an immunoglobulin heavy chain (referred to herein as "heavy chain"), a variable region of a light chain, a variable region of a heavy chain, a light chain, a heavy chain, an Fd fragment, and antibody fragments comprising essentially whole variable regions of both light and heavy chains such as an Fv, a single chain Fv Fv (scFv), a disulfide-stabilized Fv (dsFv), an Fab, an Fab', and an F(ab')2.

As used herein, the terms "complementarity-determining region" or "CDR" are used interchangeably to refer to the antigen binding regions found within the variable region of the heavy and light chain polypeptides. Generally, antibodies comprise three CDRs in each of the VH (CDR HI or HI; CDR H2 or H2; and CDR H3 or H3) and three in each of the VL (CDR LI or LI; CDR L2 or L2; and CDR L3 or L3).

The identity of the amino acid residues in a particular antibody that make up a variable region or a CDR can be determined using methods well known in the art and include methods such as sequence variability as defined by Kabat et al. (See, e.g., Kabat et al., 1992, Sequences of Proteins of Immunological Interest, 5th ed., Public Health Service, NIH, Washington D.C.), location of the structural loop regions as defined by Chothia et al. (see, e.g., Chothia et al., Nature 342:877-883, 1989), a compromise between Kabat and Chothia using Oxford Molecular's AbM antibody modeling software (now Accelrys®, see, Martin et al., 1989, Proc. Natl Acad Sci USA. 86:9268; and world wide web site www(dot)bioinf-org(dot)uk/abs), available complex crystal structures as defined by the contact definition (see MacCallum et al., J. Mol. Biol. 262:732-745, 1996) and the "conformational definition" (see, e.g., Makabe et al., Journal of Biological Chemistry, 283:1156-1166, 2008).

As used herein, the "variable regions" and "CDRs" may refer to variable regions and CDRs defined by any approach known in the art, including combinations of approaches.

Functional antibody fragments comprising whole or essentially whole variable regions of both light and heavy chains are defined as follows:
 (i) Fv, defined as a genetically engineered fragment consisting of the variable region of the light chain (VL) and the variable region of the heavy chain (VH) expressed as two chains;
 (ii) single chain Fv ("scFv"), a genetically engineered single chain molecule including the variable region of the light chain and the variable region of the heavy chain, linked by a suitable polypeptide linker as a genetically fused single chain molecule.
 (iii) disulfide-stabilized Fv ("dsFv"), a genetically engineered antibody including the variable region of the light chain and the variable region of the heavy chain, linked by a genetically engineered disulfide bond.
 (iv) Fab, a fragment of an antibody molecule containing a monovalent antigen-binding portion of an antibody molecule which can be obtained by treating whole antibody with the enzyme papain to yield the intact light chain and the Fd fragment of the heavy chain which consists of the variable and CH1 domains thereof;
 (v) Fab', a fragment of an antibody molecule containing a monovalent antigen-binding portion of an antibody molecule which can be obtained by treating whole antibody with the enzyme pepsin, followed by reduction (two Fab' fragments are obtained per antibody molecule);
 (vi) F(ab')2, a fragment of an antibody molecule containing a monovalent antigen-binding portion of an antibody molecule which can be obtained by treating whole antibody with the enzyme pepsin (i.e., a dimer of Fab' fragments held together by two disulfide bonds); and
 (vii) Single domain antibodies or nanobodies are composed of a single VH or VL domains which exhibit sufficient affinity to the antigen.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to some embodiments of the invention can be prepared by proteolytic hydrolysis of the antibody or by expression in E. coli or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

According to one embodiment, the antibody does not comprise a tag (e.g. for detection, such as for detection of CD74 expression on cells).

According to one embodiment, the antibody is a humanized antibody.

According to one embodiment, the antibody is a monoclonal antibody.

According to one embodiment, the antibody is a humanized monoclonal antibody.

According to one embodiment, the antibody binds at least one epitope of CD74 which results in reduced activation of the cell signaling pathway initiated by binding of a factor (e.g. MIF) to CD74, such as downregulation of CXCR4.

According to a specific embodiment, the CD74 targeting antibody is Milatuzumab (e.g. available from Immunomedics).

Additional CD74 targeting antibodies are commercially available from e.g. OriGene, Santa Cruz Biotechnology (SCBT), Antibodies-online. According to one embodiment, the antibody binds and neutralizes MIF.

According to one embodiment, the antibody binds MIF and prevents its binding to CD74.

According to a specific embodiment, the MIF targeting antibody is Imalumab.

Additional MIF targeting antibodies are commercially available from e.g. OriGene, Santa Cruz Biotechnology (SCBT), Antibodies-online.

Another agent which can be used along with some embodiments of the invention to downregulate CD74 and/or MIF is an aptamer. As used herein, the term "aptamer" refers to double stranded or single stranded RNA molecule that binds to specific molecular target, such as a protein. Various methods are known in the art which can be used to design protein specific aptamers. The skilled artisan can employ SELEX (Systematic Evolution of Ligands by Exponential Enrichment) for efficient selection as described in Stoltenburg R, Reinemann C, and Strehlitz B (Biomolecular engineering (2007) 24(4):381-403).

Another agent capable of downregulating CD74 and/or MIF would be any molecule which binds to and/or cleaves CD74 and/or MIF. Such molecules can be a small molecule, CD74 and/or MIF antagonists, or CD74 and/or MIF inhibitory peptide.

It will be appreciated that a non-functional analogue of at least a catalytic or binding portion of CD74 and/or MIF can be also used as an agent which downregulates CD74 and/or MIF.

Alternatively or additionally, small molecule or peptides can be used which interfere with CD74 and/or MIF protein function (e.g., catalytic or interaction).

Another agent which can be used along with some embodiments of the invention to downregulate CD74 and/or MIF is a molecule which prevents CD74 and/or MIF activation or substrate binding.

According to one embodiment, the agent capable of decreasing an activity or expression of CD74 and/or of MIF prevents the binding of MIF to CD74.

According to one embodiment, the agent capable of decreasing an activity or expression of CD74 and/or of MIF downregulates an activity or expression of CXCR4 in hematopoietic stem cells.

According to one embodiment, the agent capable of decreasing an activity or expression of CD74 upregulates content of reactive oxygen species (ROS) in the hematopoietic stem cells.

According to one embodiment, the agent capable of decreasing an activity or expression of MIF is a MIF antagonist/inhibitor selected from: Thalidomide, 3-(4-HYDROXYPHENYL)-4,5-DIHYDRO-5-ISOXAZOLE-ACETIC ACID METHYL ESTER, 3-(4-HYDROXY-PHENYL) PYRUVIC ACID, 3-FLUORO-4-HYDROXYBENZALDEHYDE O-(CYCLOHEXYLCARBONYL)OXIME, 4-HYDROXYBENZALDEHYDE O-(3,3-DIMETHYLBUTANOYL)OXIME, I-dopachrome, 2-Hydroxy-3-(4-hydroxyphenyl)propenoic acid, 4-Hydroxyphenylpyruvic acid, 5,6-Dihydroxyindole-2-carboxylic acid, Enol-phenylpyruvate, 4-IPP, AS 2444697, ISO 1, Pirfenidone, (±)-CPSI 1306 or BTZO 1.

Additional non-limiting examples of MIF antagonists have been disclosed previously, see, e.g., U.S. Pat. No. 6,774,227, U.S. Pat. Appl. No. 20120040974, Bernhagen et al., Nature 365, 756-759 (1993), Senter et al., Proc Natl Acad Sci USA 99:144-149 (2002); Dios et al., J. Med. Chem. 45:2410-2416 (2002); Lubetsky et al., J Biol Chem 277:24976-24982 (2002), which are hereby incorporated by reference.

It will be appreciated that the methods of some embodiments of the invention (e.g. increasing survival and/or expansion and/or mobilization of hematopoietic stem cells) can be performed within a subject (i.e., in vivo), within cells derived from a subject (i.e., ex vivo or in vitro) or within a hematopoietic stem cell line (i.e., in vitro).

According to some embodiments of the invention, the method of increasing survival and/or expansion of hematopoietic stem cells is effected in vitro.

According to some embodiments of the invention, the method of increasing survival and/or expansion and/or mobilization of hematopoietic stem cells is effected in vivo (e.g., for treating a disease or condition in a subject and/or for increasing mobilization of hematopoietic stem cells in a subject in need thereof).

The above mentioned agents may be administered to a subject in a single administration or in plurality of administrations (e.g. 2, 3, 4, 5 or more). If plurality of administrations is employed, the agent may be administered over the course of one day, several days, several weeks, several months or several years. One of ordinary skill in the art is capable of determining the dosage amount and the course of treatment based on the subject being treated and the level of mobilization required.

According to one embodiment, the above-mentioned agents (i.e. capable of decreasing an activity or expression of CD74 and/or of MIF) can be administered in conjunction with a chemotherapeutic agent.

According to one embodiment, the chemotherapeutic agent is a myelotoxic agent.

Exemplary chemotherapeutic agents include, but are not limited to, abarelix, adrucil, aldesleukin, aldesleukin, alemtuzumab, alitretinoin, allopurinol, altretamine, amifostine, anastrozole, arsenic trioxide, asparaginase, azacitidine, bevacuzimab, bexarotene, bleomycin, bortezomib, busulfan, calusterone, capecitabine, carboplatin, carmustine, celecoxib, cetuximab, cisplatin, cladribine, clofarabine, cyclophosphamide, cytarabine, dacarbazine, dactinomycin, actinomycin D, Darbepoetin alfa, Darbepoetin alfa, daunorubicin liposomal, daunorubicin, decitabine, Denileukin diftitox, dexrazoxane, dexrazoxane, docetaxel, doxorubicin, dromostanolone propionate, Elliott's B Solution, epirubicin, Epoetin alfa, erlotinib, estramustine, etoposide, exemestane, Filgrastim, floxuridine, fludarabine, fluorouracil 5-FU, fulvestrant, gefitinib, gemcitabine, gemtuzumab ozogamicin, goserelin acetate, histrelin acetate, hydroxyurea, Ibritumomab Tiuxetan, idarubicin, ifosfamide, imatinib mesylate, interferon alfa 2a, Interferon alfa-2b, irinotecan, lenalidomide, letrozole, leucovorin, Leuprolide Acetate, levamisole, lomustine, CCNU, meclorethamine, nitrogen mustard, megestrol acetate, melphalan, L-PAM, mercaptopurine 6-MP, mesna, methotrexate, mitomycin C, mitotane, mitoxantrone, nandrolone phenpropionate, nelarabine, Nofetumomab, Oprelvekin, Oprelvekin, oxaliplatin, paclitaxel, palifermin, pamidronate, pegademase, pegaspargase, Pegfilgrastim, pemetrexed disodium, pentostatin, pipobroman, plicamycin mithramycin, porfimer sodium, procarbazine, quinacrine, Rasburicase, Rituximab, sargramostim, sorafenib, streptozocin, sunitinib maleate, tamoxifen, temozolomide, teniposide VM-26, testolactone, thioguanine 6-TG, thiotepa, thiotepa, topotecan, toremifene, Tositumomab, Trastuzumab, tretinoin ATRA, Uracil Mustard, valrubicin, vinblastine, vinorelbine, zoledronate and zoledronic acid.

According to a specific embodiment, the chemotherapeutic agent is 5-Fluorouracil (5-FU).

The above-mentioned agents (i.e. capable of decreasing an activity or expression of CD74 and/or of MIF) can be administered alone, or in conjunction with another compound such as that which mobilizes hematopoietic stem cells, e.g. a growth factor, a cytokine, a chemokine, a polysaccharide or a drug such as cyclophosphamide or 5-fluorouracil; and/or certain antibodies, such as anti-VLA4. Combinations of these other compounds can also be used. Such additional agents can be administered prior to, concomitantly with or following administration of the agent capable of decreasing an activity or expression of CD74 and/or of MIF (discussed in detail herein above).

Any of the above described agents (e.g. chemotherapeutic agent, growth factor, cytokine, chemokine, etc.) can be administered prior to (e.g. minutes, hours, days, or weeks), concomitantly with, or following (e.g. minutes, hours, days, or weeks) administration of the agent capable of decreasing an activity or expression of CD74 and/or of MIF.

Examples of mobilization factors which can be used in addition to the above described agents include, but are not limited to, Granulocyte-colony stimulating factor (G-CSF) e.g. Filgrastim; granulocyte-macrophage colony stimulating factor (GM-CSF) e.g. Sargramostim; Erythropoietin; Stem cell factor (SCF) e.g. Ancestim; or combinations thereof (e.g. SCF in combination with G-CSF). Other compounds, which can be used include e.g. polysaccharides (e.g., Zymosan), which mobilize HSPC within 1 hour after a single injection. Mobilization could also be induced by chemokines (e.g., IL-8, Gro-β), growth factors (e.g., vascular endothelial growth factor), and CXCR4 antagonists. Longer lasting variants of G-CSF (Pegfilgrastim, Amgen) and erythropoietin (Darbopoietin, Amgen) may also be used as mobilizing agents.

Examples of commercially available recombinant human G-CSF include filgrastim (Gran® and Neupogen®), lenograstim (Neutrogin® and Granocyte®) and nartograstim (Neu-up®). Examples of commercially available human GM-CSF include Sargramostim and Leucotropin. Examples of commercially available SCF include Ancestim (StemGen®).

Examples of commercially available CXCR4 antagonists which may be used in conjunction with the agents of the invention include e.g. Mozobil (plerixafor) (AnorMED Inc.), AMD-070 (AnorMED Inc.), BKT140 (Biokine Therapeutics Inc.), CXCR4 monoclonal antibody (Northwest Biotherapeutics Inc.), KRH-2731/CS-3955 (Daiichi Sankyo Company), AVR 118 (reticulose) (Advanced Viral Research Corp.), CXCR4 antagonist (TaiGen Biotechnology), CTCE-0214 (Chemokine Therapeutics Corp), and AMD3100 (AnorMed, Vancouver, Canada).

Any methods including quantitative and qualitative methods can be used to identify that the hematopoietic stem cells have been mobilized into the peripheral blood. The methods typically involve isolating a quantity of the patient's blood and analyzing the quantity of the cells within the blood. Any method can be used to analyze the number of cells, including but not limited to: ELISA to identify the specific cells, FACS analysis, coulter counters and other blood counting devices, morphological identification, and PCR. The cells can be identified by any method known to one of skill in the art, including but not limited to, the identification of one or more proteins which are specifically expressed by the precursor cells, by morphology, by mRNA expression, and by PCR. The identification of the cells can be done at any time after administration of the agent, included but not limited to: 5 minutes, 10 minutes, 20 minutes, 30 minutes, 45 minutes, 1 hour, 1.5 hours, 2 hours, 3 hours, 4 hours, 5 hours, 6 hours, 7 hours, 8 hours, 9 hours, 10 hours, 12 hours, 1 day, 2 days, 3 days, 4 days, 5 days, 6 days, 7 days, 2 weeks, 1 month, 2 months, 3 months, 4 months, 5 months, 6 months, 7 months, 8 months, 9 months, 10 months, 1 year, 2 years following administration of the agent. Further, the mobilization can be identified soon after treatment to identify whether the treatment is working.

The efficacy of the mobilization can be tested throughout treatment with the agents of the present invention, or alternatively, an initial test to determine efficacy can be performed. In one embodiment, a test is performed 1 day after treatment and again 1 week after treatment.

The method of mobilizing hematopoietic stem cells can be used for mobilization of stem cells in patients who will undergo cytoreductive therapy, such as chemotherapy or radiation therapy. In such cases, mobilization may be induced prior to, concomitantly with, or following the cytoreductive therapy.

In addition, the method of mobilizing hematopoietic stem cells can be used for patients who are "difficult to mobilize" because, for example, they are not sensitive to growth factors.

Following mobilization, the hematopoietic stem cells may be collected (e.g. harvested) from the peripheral blood.

Additionally or alternatively, hematopoietic stem cells may be obtained (i.e. collected) directly from the bone marrow.

According to one aspect of the invention, there is provided a method of obtaining hematopoietic stem cells for transplantation, the method comprising: (a) administering to a subject (e.g. donor subject) an effective amount of an agent capable of decreasing an activity or expression of CD74 and/or of MIF; and (b) collecting hematopoietic stem cells, thereby obtaining hematopoietic stem cells for transplantation.

According to a specific embodiment, the hematopoietic stem cells are not transduced with a lentivirus.

According to one embodiment, the method further comprises mobilizing the hematopoietic stem cells from the bone marrow to the peripheral blood prior to collecting (e.g. using any of the mobilizing agents discussed hereinabove).

Various methods of collecting hematopoietic stem cells are known in the art. For example, hematopoietic stem cells may be collected by a surgical procedure or by an apheresis procedure.

From the bone marrow, hematopoietic stem cells can be obtained using a surgical procedure such as bone marrow aspiration.

From the peripheral blood, the hematopoietic stem cells can be retrieved by apheresis (also referred to as leukapheresis). In order to obtain sufficient number of hematopoietic stem cells, the procedure may be repeated (e.g. over the course of several days or weeks).

Following collection, the harvested cells may be further separated for a specific cell phenotype (or lack thereof), e.g. CD133 expression (e.g. using an anti-CD133 antibody), CD34 expression (e.g. using an anti-CD34 antibody) or CD74 expression (e.g. using an anti-CD74 antibody) using, for example, Magnetic-activated cell sorting (MACS) or FACS.

According to one embodiment, the method further comprises isolating hematopoietic stem cells having CD74 levels below a predetermined threshold. According to one embodiment, CD74 levels are reduced by at least about 10%, 20%, 30%, 40%, 50%, 60%, 70%, 80%, 90% or 100% as compared to CD74 levels in hematopoietic stem cells not treated according to the methods of some embodiments of the invention. Cells can be isolated using any method known in the art, such as by MACS or FACS, selecting for cells not expressing or expression low levels of CD74.

According to one embodiment, after collection (and optionally separation), the hematopoietic stem cells may be stored (e.g. for later use), expanded in culture or administered to a subject in need thereof (as discussed in detail herein below). Accordingly, the method of mobilizing stem cells can be used for mobilization of precursor hematopoietic cells in individuals who will serve as allogenic or autologous donors of hematopoietic stem cells.

In order to obtain sufficient number of hematopoietic stem cells for transplantation, the collected hematopoietic stem cells may be further cultured in vivo in order to increase expansion (e.g. with an agent capable of decreasing an activity or expression of CD74 and/or MIF, as discussed in detail hereinabove).

During in vitro culturing, the hematopoietic stem cells may change their cell phenotype (e.g. the levels of CD74 expression may be altered). The presence or absence of an antigen on the surface of cells may be analyzed using specific antibodies (e.g. CD74 antibodies) by methods well known by the person skilled in the art, like, for example, ELISA of FACS. It may further be analyzed by other methods well known in the art, like RT-PCR or the like.

The hematopoietic stem cells can additionally be used for gene therapy. Because pluripotent hematopoietic stem cells are self-renewing, and give rise to blood cell progenitors as well as mature blood cells, the hematopoietic stem cells are an appropriate target for gene therapy. After collection (and optionally separation), the hematopoietic stem cells can be modified to deliver gene products upon reintroduction to the individual. After modification, the cells are reinfused into a subject in need of such treatment.

It will be appreciated that commercially available human hematopoietic stem cells can also be used according to some embodiments of the present invention. Human hematopoietic stem cells can be purchased from the NIH human embryonic stem cells registry (www(dot)escr(dot)nih(dot)gov>) or from ATCC®. Non-limiting examples of commercially available hematopoietic stem cells include: Primary Bone Marrow CD34$^+$ Cells (ATCC® Number: PCS-800-012™) and Primary Cord Blood CD34$^+$ Cells (ATCC® Number: PCS-800-014™).

According to another aspect of the invention, there is provided an isolated population of hematopoietic stem cells obtainable by the method of some embodiments of the invention.

According to another aspect of the invention, there is provided an isolated population of hematopoietic stem cells comprising an agent capable of decreasing an activity or expression of CD74.

The phrase "isolated population of cells" as used herein refers to cells which have been isolated from their natural environment (e.g., the human body).

According to one embodiment, the agent (e.g. polynucleotide agent) is an exogenous agent added to the cells to decrease an activity or expression of CD74.

According to one embodiment, the cells are cultured ex vivo or in vitro.

Each of the agents used for down-regulating an activity or expression of CD74 and/or of MIF, or the isolated population of cells, described hereinabove, can be administered to the subject per se or as part of a pharmaceutical composition which also includes a physiologically acceptable carrier. The purpose of a pharmaceutical composition is to facilitate administration of the active ingredient to an organism.

It will be appreciated that the pharmaceutical composition may further comprise other compounds such as described in detail hereinabove.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the agent which downregulates an activity or expression of CD74 and/or of MIF, or the isolated population of cells, accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, PA, latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

The term "tissue" refers to part of an organism consisting of an aggregate of cells having a similar structure and/or a common function. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients (agent which downregulates an activity or expression of CD74 and/or of MIF, or the isolated population of cells) effective to prevent, alleviate or ameliorate symptoms of a disorder (e.g., disease or condition requiring hematopoietic stem cells) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Animal models such as immunocompetent mice, immunodeficient mice (e.g. SCID mice) or animal models for hematopoietic cancer (e.g. a B-CLL animal model such as the NOD-SCID mouse chimera as described previously by Shimoni A et al. A model for human B-chronic lymphocytic leukemia in human/mouse radiation chimera: evidence for tumor-mediated suppression of antibody production in lowstage disease. Blood. 1997; 89:2210-2218) can be used to determine therapeutic efficacy of the agents of the present invention in vivo.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide adequate levels of the active ingredient as to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

According to one embodiment, agents will be given for a sufficient amount of time to enable survival, expansion and/or mobilization of hematopoietic stem cells. Thus, it is advisable to draw a base-line blood sample from each subject prior to administration of the agents of the present invention. Furthermore, once a subject received modulating factors, it is advisable that they return for follow-up evaluation, which include, for example, hematologic and chemical tests for safety.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

According to one embodiment, the composition may further comprise (e.g. in addition to the agent capable of decreasing an activity or expression of CD74 and/or of MIF) one or more other agents that induce or enhance mobilization, such as growth factors affecting hematopoietic stem cells, e.g. stem cell factor (SCF), or cytokine that stimulates mobilization of hematopoietic stem cells, such as a colony-stimulating factor, e.g. granulocyte-colony stimulating factor (G-CSF) or granulocyte-macrophages colony stimulating factor (GM-CSF). Other compounds, which can be included in the composition include polysaccharides (e.g., Zymosan), chemokines (e.g., IL-8, Gro-β), growth factors (e.g., vascular endothelial growth factor), and/or CXCR4 antagonists. Examples of commercially available G-CSF, GM-CSF, SCF and CXCR4 antagonists are discussed herein above.

According to one embodiment, the composition may further comprise (e.g. in addition to the agent capable of decreasing an activity or expression of CD74 and/or of MIF) one or more chemotherapeutic agents. Such agents are discussed in detail hereinabove.

According to one embodiment, in order to augment the therapeutic effect, the composition may further comprise other therapeutically or nutritionally useful agents. These include, but are not limited to, radiotherapy, biological therapy e.g., immunotherapy, antibiotics, vitamins, herbal extracts, anti-inflammatories, glucose, antipyretics, analgesics, interleukins (IL-1, IL-2, IL-3, IL4, IL-5, IL-6, IL-7, IL-8, IL-9, IL-10 IL-11, IL-12, IL-13, IL-14, or IL-15), TPO, or other growth factor such as CSF-1, SF, leukemia inhibitory factor (LIF), or fibroblast growth factor (FGF), as well as C-KIT ligand, M-CSF and TNF-α, PIXY-321 (GM-CSF/IL-3 fusion protein), macrophage inflammatory protein, thrombopoietin, and the like.

The agents of the present invention or isolated population of cells (described hereinabove) can be used for treatment.

Thus, according to one aspect of the invention, there is provided a method of treating a disease or condition in a subject in need of enhanced hematopoietic stem cell survival and/or expansion and/or mobilization, the method comprising administering to the subject a therapeutically effective amount of an agent capable of decreasing an activity or expression of CD74 and/or of macrophage migration inhibitory factor (MIF), thereby treating the disease or condition in the subject.

According to one aspect of the invention, there is provided a therapeutically effective amount of an agent capable of decreasing an activity or expression of CD74 and/or of MIF for use in treating a disease or condition in a subject in need of enhanced hematopoietic stem cell survival and/or expansion and/or mobilization.

According to a specific embodiment, when the agent used for treatment is an agent capable of decreasing an activity or expression of MIF, the disease or condition to be treated is not a cancer (e.g. solid tumor or hematopoietic malignancy), an autoimmune disease, an infection (e.g. caused by a flavivirus, such as West Nile, Dengue, Japanese encephalitis, St Louis encephalitis, or equine encephalitis viruses), an anemia of chronic disease, a malaria, an asthma, or an autism.

According to a specific embodiment, when the agent used for treatment is an agent capable of decreasing an activity or expression of CD74, the disease or condition to be treated is not a cancer (e.g. solid tumor or hematopoietic malignancy).

According to a specific embodiment, when the agent used for treatment is an agent capable of decreasing an activity or expression of MIF and/or of CD74, the disease or condition to be treated may be a non-malignant disease such as, but not limited to, an organ dysfunction or failure (e.g. renal disease or liver disease which are associated with cytopenia), a hematologic non-malignant disease (e.g. cytopenia, anemia, sickle cell disease, hemophilia), a graft related disease (e.g. graft rejection), an immune deficiency, an immune deficiency e.g. severe combined immunodeficiency syndromes (SCID), a genetic disease, a metabolic disorder, an inflammatory disease (e.g. systemic inflammatory disease), an allergic disease, a trauma and an injury.

According to one aspect of the invention, there is provided a method of treating a disease or condition requiring hematopoietic stem cell transplantation in a subject in need thereof, the method comprising administering to the subject a therapeutically effective amount of the isolated population of cells of some embodiments of the invention.

According to one aspect of the invention, there is provided a therapeutically effective amount of the isolated population of cells of some embodiments of the invention for use in treating a disease or condition requiring hematopoietic stem cell transplantation in a subject in need thereof.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

According to one embodiment, an individual is successfully "treated" if one or more symptoms associated with the disease or condition are mitigated or eliminated, including but not limited to, decreasing symptoms resulting from the disease, increasing the quality of life of those suffering from the disease, decreasing the dose of other medications required to treat the disease, delaying the progression of the disease, and/or prolonging survival of individuals.

Treatment can be evaluated using any method known in the art for evaluation of the specific disease or condition (e.g. utilizing blood tests, physical examination, ultrasound, CT scan, MRI, etc.) such a method can be determined by one of skill in the art.

Typical conditions that can be ameliorated or otherwise benefited by enhanced hematopoietic stem cell survival and/or expansion and/or mobilization and/or hematopoietic stem cell transplantation, include, but are not limited to, hematopoietic disorders and malignancies, such as aplastic anemia, lymphoma, leukemia, immune deficiency, severe combined immune deficiency (SCID), cytopenia (e.g. anemia, leukopenia, neutropenia, thrombocytopenia, granulocytopenia, pancytopenia), drug-induced cytopenia, toxin-induced cytopenia, radiation-induced cytopenia, cytopenia associated with conventional bone marrow transplantation, hematopoietic deficits associated with oncology treatment, with chemotherapy, or with radiation therapy, anemia or cytopenia of chronic disease (also referred to as anemia or cytopenia of chronic inflammation), osteopetrosis, Gaucher's disease, thalassemia and other congenital or genetically-determined hematopoietic abnormalities.

According to one embodiment, the methods of the invention are useful in enhancing the success of transplantation during and following immunosuppressive treatments as well as in effecting more efficient wound healing and treatment of bacterial inflammation.

According to one embodiment, the methods of the invention are useful for treating subjects who are immunocompromised or whose immune system is otherwise impaired. Typical conditions that are ameliorated or otherwise benefited by the method of the present invention include, but are not limited to, those subjects who are infected with a retrovirus and more specifically who are infected with human immunodeficiency virus (HIV).

Accordingly, the methods of the invention may be used for the treatment of a broad spectrum of conditions for which elevation of hematopoietic stem cell levels in a subject would be beneficial or, where harvesting of stem cell for subsequent stem cell transplantation would be beneficial. The compounds are also administered to regenerate myocardium by mobilizing bone marrow stem cells.

The methods described herein are also particularly suitable for those subjects in need of repeated or high doses of chemotherapy. For some cancer patients, hematopoietic toxicity frequently limits the opportunity for chemotherapy dose escalation or completion of prescribed chemotherapy. Repeated or high dose cycles of chemotherapy can be responsible for severe stem cell depletion leading to important long-term hematopoietic sequelea and marrow exhaustion. The methods of the present invention provide for improved cell survival, blood cell reconstitution and blood cell count when used in conjunction with chemotherapy.

In one embodiment, the disease or condition is a malignant disease.

As used herein, the term "malignant disease" or "cancer" refers to any cancerous disease. Cancer cells may be associated with phenotypes such uncontrolled proliferation, loss of specialized functions, immortality, significant metastatic potential, significant increase in anti-apoptotic activity, rapid growth and proliferation rate, and certain characteristic morphology and cellular markers.

In some circumstances, cancer cells will be in the form of a tumor, such cells may exist locally within an animal (e.g. solid tumor), alternatively, cancer cells may circulate in the blood stream as independent cells, for example, leukemic cells (non-solid tumor), or may be dispersed throughout the body (e.g. metastasis). It will be appreciated that the term "cancer" as used herein encompasses all types of cancers, at any stage and in any form.

Types of malignant diseases amenable to diagnosis or treatment by the methods of some embodiments of the invention include benign tumors, warts, polyps, pre-cancers, and malignant tumors/cancers.

Specific examples of cancerous diseases which can be treated using the methods of the present invention include, but are not limited to, carcinoma, lymphoma, blastoma, sarcoma, and leukemia. More particular examples of such cancers include squamous cell cancer, soft-tissue sarcoma, Kaposi's sarcoma, melanoma, lung cancer (including small-cell lung cancer, non-small-cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, rectal cancer, endometrial or uterine carcinoma, carcinoid carcinoma, salivary gland carcinoma, kidney or renal cancer, liver cancer, prostate cancer, vulval cancer, thyroid cancer, hepatic carcinoma, mesothelioma, multiple myeloma, post-transplant lymphoproliferative disorder (PTLD), and various types of head and neck cancer (e.g. brain tumor). The cancerous conditions amenable for treatment of the invention include metastatic cancers.

According to one embodiment, the malignant disease is a hematological malignancy. Exemplary hematological malignancies include, but are not limited to, leukemia [e.g., acute lymphatic, acute lymphoblastic, acute lymphoblastic pre-B cell, acute lymphoblastic T cell leukemia, acute—megakaryoblastic, monocytic, acute myelogenous, acute myeloid, acute myeloid with eosinophilia, B cell, basophilic, chronic myeloid, chronic, B cell, eosinophilic, Friend, granulocytic or myelocytic, hairy cell, lymphocytic, megakaryoblastic, monocytic, monocytic-macrophage, myeloblastic, myeloid, myelomonocytic, plasma cell, pre-B cell, promyelocytic, subacute, T cell, lymphoid neoplasm, predisposition to myeloid malignancy, acute nonlymphocytic leukemia, T-cell acute lymphocytic leukemia (T-ALL) and B-cell chronic lymphocytic leukemia (B-CLL)] and lymphoma [e.g., Hodgkin's disease, non-Hodgkin's lymphoma, Burkitt, cutaneous T cell, histiocytic, lymphoblastic, T cell, thymic, B cell, including low grade/follicular; small lymphocytic (SL) NHL; intermediate grade/follicular NHL; intermediate grade diffuse NHL; high grade immunoblastic NHL; high grade lymphoblastic NHL; high-grade small non-cleaved cell NHL; bulky disease NHL; mantle cell lymphoma; AIDS-related lymphoma; and Waldenstrom's Macroglobulinemia].

According to a specific embodiment, the malignant disease is a leukemia, a lymphoma, a myeloma, a melanoma, a sarcoma, a neuroblastoma, a colon cancer, a colorectal cancer, a breast cancer, an ovarian cancer, an esophageal cancer, a synovial cell cancer, a hepatic cancer and a pancreatic cancer.

According to one embodiment, the subject has a non-malignant disease.

According to one embodiment, the non-malignant disease is an organ dysfunction or failure (e.g. renal disease or liver disease which are associated with cytopenia), a hematologic non-malignant disease (e.g. cytopenia, anemia, sickle cell disease, hemophilia), a graft related disease (e.g. graft rejection), an immune deficiency, a severe combined immunodeficiency syndromes (SCID), a genetic disease, a metabolic disorder, an infectious disease, an inflammatory disease (e.g. systemic inflammatory disease such as that associated with cytopenia), an autoimmune disease, an allergic disease, a trauma and an injury.

Inflammatory Diseases—Include, but are not limited to, chronic inflammatory diseases and acute inflammatory diseases.

Inflammatory Diseases Associated with Hypersensitivity

Examples of hypersensitivity include, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH.

Type I or immediate hypersensitivity, such as asthma.

Type II hypersensitivity include, but are not limited to, rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1-2):49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl: S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8):1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998; 7 Suppl 2:S107-9), neurodegenerative diseases, neurological diseases, neurological autoimmune diseases, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83), motor neuropathies (Kornberg A J. J Clin Neurosci. 2000 May; 7 (3):191), Guillain-Barre syndrome, neuropathies and autoimmune neuropathies (Kusunoki S. Am J Med Sci. 2000 April; 319 (4):234), myasthenic diseases, Lambert-Eaton myasthenic syndrome (Takamori M. Am J Med Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydenham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann N Y Acad Sci. 1998 May 13; 841:482), cardiovascular diseases, cardiovascular autoimmune diseases, atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16):660); anti-factor VIII autoimmune disease (Lacroix-Desmazes S. et al., Semin Thromb Hemost. 2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Interne (Paris). 2000 May; 151 (3):178); antiphospholipid syndrome (Flamholz R. et al., J Clin Apheresis 1999; 14 (4): 171); heart failure, agonist-like β-adrenoceptor antibodies in heart failure (Wallukat G. et al., Am J Cardiol. 1999 Jun. 17; 83 (12A):75H), thrombocytopenic purpura (Moccia F. Ann Ital Med Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2): 122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000 August; 33 (2):326) and primary biliary cirrhosis (Strassburg C P. et al., Eur J Gastroenterol Hepatol. 1999 June; 11 (6):595).

Type IV or T cell mediated hypersensitivity, include, but are not limited to, rheumatoid diseases, rheumatoid arthritis (Tisch R, McDevitt H O. Proc Natl Acad Sci USA 1994 Jan. 18; 91 (2):437), systemic diseases, systemic autoimmune diseases, systemic lupus erythematosus (Datta S K., Lupus 1998; 7 (9):591), glandular diseases, glandular autoimmune diseases, pancreatic diseases, pancreatic autoimmune diseases, Type 1 diabetes (Castano L. and Eisenbarth G S. Ann. Rev. Immunol. 8:647); thyroid diseases, autoimmune thyroid diseases, Graves' disease (Sakata S. et al., Mol Cell Endocrinol 1993 March; 92 (1):77); ovarian diseases (Garza K M. et al., J Reprod Immunol 1998 February; 37 (2):87), prostatitis, autoimmune prostatitis (Alexander R B. et al., Urology 1997 December; 50 (6):893), polyglandular syndrome, autoimmune polyglandular syndrome, Type I autoimmune polyglandular syndrome (Hara T. et al., Blood. 1991 Mar. 1; 77 (5):1127), neurological diseases, autoimmune neurological diseases, multiple sclerosis, neuritis, optic neuritis (Soderstrom M. et al., J Neurol Neurosurg Psychiatry 1994 May; 57 (5):544), myasthenia gravis (Oshima M. et al., Eur J Immunol 1990 December; 20 (12):2563), stiff-man syndrome (Hiemstra H S. et al., Proc Natl Acad Sci USA 2001 Mar. 27; 98 (7):3988), cardiovascular diseases, cardiac autoimmunity in Chagas' disease (Cunha-Neto E. et al., J Clin Invest 1996 Oct. 15; 98

(8):1709), autoimmune thrombocytopenic purpura (Semple J W. et al., Blood 1996 May 15; 87 (10):4245), anti-helper T lymphocyte autoimmunity (Caporossi A P. et al., Viral Immunol 1998; 11 (1):9), hemolytic anemia (Sallah S. et al., Ann Hematol 1997 March; 74 (3):139), hepatic diseases, hepatic autoimmune diseases, hepatitis, chronic active hepatitis (Franco A. et al., Clin Immunol Immunopathol 1990 March; 54 (3):382), biliary cirrhosis, primary biliary cirrhosis (Jones D E. Clin Sci (Colch) 1996 November; 91 (5):551), nephric diseases, nephric autoimmune diseases, nephritis, interstitial nephritis (Kelly C J. J Am Soc Nephrol 1990 August; 1 (2):140), connective tissue diseases, ear diseases, autoimmune connective tissue diseases, autoimmune ear disease (Yoo T J. et al., Cell Immunol 1994 August; 157 (1):249), disease of the inner ear (Gloddek B. et al., Ann N Y Acad Sci 1997 Dec. 29; 830:266), skin diseases, cutaneous diseases, dermal diseases, bullous skin diseases, pemphigus vulgaris, bullous pemphigoid and pemphigus foliaceus.

Examples of delayed type hypersensitivity include, but are not limited to, contact dermatitis and drug eruption.

Examples of types of T lymphocyte mediating hypersensitivity include, but are not limited to, helper T lymphocytes and cytotoxic T lymphocytes.

Examples of helper T lymphocyte-mediated hypersensitivity include, but are not limited to, $T_h1$ lymphocyte mediated hypersensitivity and $T_h2$ lymphocyte mediated hypersensitivity.

Autoimmune Diseases

Include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost. 2000; 26 (2):157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151 (3):178), antiphospholipid syndrome (Flamholz R. et al., J Clin Apheresis 1999; 14 (4): 171), antibody-induced heart failure (Wallukat G. et al., Am J Cardiol. 1999 Jun. 17; 83 (12A):75H), thrombocytopenic purpura (Moccia F. Ann Ital Med Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. Diseases include, but are not limited to autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl: S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12): 7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1): 16), celiac disease (Landau Y E. and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med Sci. 2000 April; 319 (4):234), myasthenia, Lambert-Eaton myasthenic syndrome (Takamori M. Am J Med Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydenham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann N Y Acad Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2):140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

Infectious Diseases

Examples of infectious diseases include, but are not limited to, chronic infectious diseases, subacute infectious diseases, acute infectious diseases, viral diseases, bacterial diseases, protozoan diseases, parasitic diseases, fungal diseases, mycoplasma diseases and prion diseases.

Specific types of viral pathogens causing infectious diseases treatable according to the teachings of the present invention include, but are not limited to, retroviruses, circoviruses, parvoviruses, papovaviruses, adenoviruses, herpesviruses, iridoviruses, poxviruses, hepadnaviruses, picornaviruses, caliciviruses, togaviruses, flaviviruses, reoviruses, orthomyxoviruses, paramyxoviruses, rhabdoviruses, bunyaviruses, coronaviruses, arenaviruses, and filoviruses.

Specific examples of viral infections which may be treated according to the teachings of the present invention include, but are not limited to, those caused by human immunodeficiency virus (HIV)-induced acquired immunodeficiency syndrome (AIDS), influenza, rhinoviral infection, viral meningitis, Epstein-Barr virus (EBV) infection, hepatitis A, B or C virus infection, measles, papilloma virus infection/warts, cytomegalovirus (CMV) infection, Herpes simplex virus infection, yellow fever, Ebola virus infection, rabies, Adenovirus (Adv), cold viruses, flu viruses, Japanese encephalitis, polio, respiratory syncytial, rubella, smallpox, varicella zoster, rotavirus, West Nile virus and zika virus.

Specific examples of bacterial infections which may be treated according to the teachings of the present invention include, but are not limited to, those caused by anthrax; gram-negative bacilli, chlamydia, diptheria, haemophilus influenza, *Helicobacter pylori*, malaria, *Mycobacterium tuberculosis*, pertussis toxin, pneumococcus, rickettsiae, staphylococcus, streptococcus and tetanus.

Specific examples of superbug infections (e.g. multi-drug resistant bacteria) which may be treated according to the teachings of the present invention include, but are not limited to, those caused by *Enterococcus faecium, Clostridium difficile, Acinetobacter baumannii, Pseudomonas aeruginosa*, and Enterobacteriaceae (including *Escherichia coli, Klebsiella pneumoniae, Enterobacter* spp.).

Specific examples of fungal infections which may be treated according to the teachings of the present invention include, but are not limited to, those caused by candida, coccidiodes, cryptococcus, histoplasma, leishmania, plasmodium, protozoa, parasites, schistosoma, tinea, toxoplasma, and *Trypanosoma cruzi*.

Graft Rejection Diseases

According to other embodiment, the disease is associated with transplantation of a graft. Examples of diseases associated with transplantation of a graft include, but are not limited to, graft rejection, chronic graft rejection, subacute graft rejection, hyperacute graft rejection, acute graft rejection, allograft rejection, xenograft rejection and graft-versus-host disease (GVHD).

Allergic Diseases

Examples of allergic diseases include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

Non-Malignant Hematologic Disease

Examples of non-malignant hematologic diseases include, but are not limited to, cytopenia (e.g. anemia, leukopenia, neutropenia, thrombocytopenia, granulocytopenia, pancytopenia), drug-induced cytopenia, toxin-induced cytopenia, radiation-induced cytopenia or cytopenia associated with conventional bone marrow transplantation, bone marrow disorders, deep vein thrombosis/pulmonary embolism, diamond blackfan anemia, hemochromatosis, hemophilia, immune hematologic disorders, iron metabolism disorders, sickle cell disease, thalassemia, osteopetrosis, Von Willebrand disease, and Gaucher's disease.

In cases wherein treatment of a disease or condition requires hematopoietic stem cell transplantation, autologous (e.g. derived from the subject), allogeneic (e.g. derived from a donor who is of the same species as the subject, but which is substantially non-clonal with the subject) or xenogeneic (e.g. derived from a donor who is of a different species relative to the species of a substantial proportion of the lymphocytes of the subject) hematopoietic stem cells can be transplanted to a recipient suffering from a disease.

The hematopoietic stem cells of the present invention may be transplanted into a recipient using any method known in the art for cell transplantation, such as but not limited to, cell infusion (e.g. I.V.) or via an intraperitoneal route.

It will be appreciated that since the hematopoietic stem cells of the present invention comprise enhanced properties (e.g. enhanced survival and/or expansion), a lower dose of cells may be needed for transplantation as compared to hematopoietic stem cells not treated with an agent capable of decreasing an activity or expression of CD74 and/or of MIF. One of skill in the art will be able to make such as determination.

It is expected that during the life of a patent maturing from this application many relevant agents will be developed and the scope of the term agent is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Procedures

Mice

C57BL/6, CD74$^{-/-}$, MIF$^{-/-}$ and CD45.1 mice were used in this study.

N-acetyl-L-cystein (NAC) was administrated by intraperitoneal (i.p.) injection (50 mg/kg; Sigma) for six consecutive days before the start of the experiment. 5-fluoroouracil (5-FU) was administrated by i.p. injection (150 mg/kg; ABIC, Teva group) once a week. All of the animal experiments were approved by the Weizmann Institute Animal Care and Use Committee.

Flow Cytometry

For flow cytometry analyses, the following monoclonal antibodies were used:

Lin (Lineage) or Lin APC/Cy 7 (Gr-1, Ter119 CD3, CD11b, CD115), c-Kit (clone: 2B8), B220 (clone: RA3-6B2), B220 (clone: RA3-6B2), IgM (clone: RMM-1), IgD (clone: 11-26c). For myeloid lineage staining: CD115 (clone: AFS98), CD11b (clone: M1/70), Gr-1 (clone: RB6-8C5), Ter119 (clone: TER-119), CD3 (clone: 145-2C11).

For the chimeric mice staining: CD45.1 (clone: A20), CD45.2 (clone: 104), CD150, CD48. All purchased from Biolegend USA.

Sca-1 (clone: D7) and CD34 (clone: RAM34) were purchased from eBioscience, USA, and CD74 was purchased from R & D Systems, USA. CXCR4 (cat: TP-503) was purchased from Torrey Pines Biolabs.

All analyses were done using FACS Canto II flow cytometer (BD Bioscience, USA). Sorting of the LSK population and the CD34$^-$/LSK population was done using FACS Aria II system (BD Bioscience, USA). All flow cytometry data was analyzed using FlowJo software (FlowJo, LLC, USA).

Environment Experiments

Lethally irradiated (950 Rad) C57BL/6 (WT) recipient mice were reconstituted with 5×10$^6$ of either WT or CD74$^{-/-}$ total BM cells. Additionally, lethally irradiated (950 rad) CD74$^{-/-}$ on a C57BL/6 background recipient mice were reconstituted with 5×10$^6$ of either WT or CD74$^{-/-}$ total BM cells. Long-term reconstitution of the peripheral blood and bone marrow was evaluated at 16 weeks post-transplant. Analyses were done using FACS Canto II flow cytometer (BD Bioscience, USA). The data was analyzed using FlowJo software (FlowJo, LLC, USA).

Colony-Forming Assays (CFU-C)

BM mononuclear (BM-MNC) cells were isolated by Ficoll separation and were seeded (15×10$^3$ cells/ml) in CFU-C semisolid medium supplemented with EPO, IL-3, GM-CSF and SCF as previously described (Kollet O, Dar A, Shivtiel S, Kalinkovich A, Lapid K, Sztainberg Y et al. Osteoclasts degrade endosteal components and promote mobilization of hematopoietic progenitor cells. Nat Med 2006; 12: 657-664). CFU-C were scored 7 days after plating and presented as CFU-C per number of seeded cells.

Competitive Total Bone-Marrow Cells Transplantation

Lethally irradiated (950 Rad) WT CD45.1 on a C57BL/6 background recipient mice, were reconstituted with 2.5×10$^6$ WT CD45.1 total BM cells together with either 2.5×10$^6$ CD45.2 WT or 2.5×10$^6$ CD45.2 CD74$^{-/-}$ total BM cells (1:1 ratio) or 1.5×10$^6$ WT CD45.1 with 0.5×10$^6$ CD45.2 WT or 1.5×10$^6$ CD45.2 CD74$^{-/-}$ (3:1 ratio). Short- and long-term reconstitution of donor (CD45.1 and CD45.2) was monitored 6, 16 and 24 weeks post-transplantation. Analyses were done using FACS Canto II flow cytometer (BD Bioscience, USA). The data was analyzed using FlowJo software (FlowJo, LLC, USA).

Competitive LSK Cells Transplantation

Lethally irradiated (950 Rad) WT CD45.1 on a C57BL/6 background recipient mice were reconstituted with 75,000 WT CD45.1 sorted LSK (Lin$^-$/Sca-1$^+$/c-Kit$^+$) cells together with 75,000 CD45.2 CD74$^{-/-}$ sorted LSK (Lin$^-$/Sca-1$^+$/c-Kit$^+$) cells, in a 1:1 ratio. Sorting of the LSK CD45.1 WT and CD45.2 CD74$^{-/-}$ cells was done using FACS Aria II system (BD Bioscience, USA), following enrichment with CD117 (c-Kit) MicroBeads (cat: 130-091-224) using LS MACS Separation Columns (cat: 130-042-401), both obtained from Miltenyi Biotec, UK. Short and long-term reconstitution of donor bone marrow was evaluated at 6 and 18 weeks post-transplantation. Analyses were done using FACS Canto II flow cytometer (BD Bioscience, USA). The data was analyzed using FlowJo software (FlowJo, LLC, USA).

Serial Transplantation

For serial transplantation assay, BM cells (2×10$^6$) were obtained from six WT and six CD74$^{-/-}$ mice transplanted to lethally irradiated WT CD45.1. Each donor was transplanted to 4-5 recipient mice. 10-12 weeks after transplantation, one mouse from each donor served as a donor for the following transplant.

Cell-Cycle Analyses

To analyze quiescence cells, total bone-marrow cells were stained for the designated markers (lineage/Sca-1/c-Kit/CD34), fixed and permeabilized using BD Cytofix/Cytoperm Plus kit (BD Bioscience, USA) and stained with the Ki-67 antibody (cat: 556026; BD Pharmingen, USA). To determine proliferation, C57BL/6 and CD74$^{-/-}$ mice were fed with 0.8 mg/ml BrdU in the drinking water for 3 days. BrdU incorporation was followed in LSK cells from bone-marrow using the BrdU flow kit (BD Pharmingen)

Reactive Oxygen Species (ROS) Analyses

Cellular ROS levels was detected by incubating total bone marrow cells with 2 uM hydroethidine (Molecular Probes, USA) for 10 minutes at 37° C. Cells were then washed with PBS and stained for lineage/Sca-1/c-Kit/CD34 markers.

Apoptosis Analyses

To determine the apoptosis levels in lineage/Sca-1/c-Kit/CD34 cell populations, total bone marrow cells were stained with the appropriate antibodies, using the Annexin V binding buffer (1:10 in DDw; cat: 556454, BD Pharmingen, USA) and mixed with Annexin V (FITC Annexin V, cat: 556419; BD Pharmingen, USA). All samples were incubated for 15 minutes in room temperature. For measuring annexin level under hypoxia, BM cells were incubated in hypoxia chamber 1% $O_2$ for 24 hours before staining.

Chip Sequencing

Bone marrow cells from WT mice were enriched for Lin$^-$ cell by magnetic beads (Miltenyi Biotec, UK) as previously discussed in Gil-Yarom N., Proc Natl Acad Sci USA. (2017) 114(3):562-567.

RNA Sequencing

WT and CD74$^{-/-}$ total bone marrow cells were enriched for c-Kit (CD117) positive cells using CD117 MicroBeads (cat: 130-091-224) and LS MACS Separation Columns (cat: 130-042-401), both obtained from Miltenyi Biotec, UK. Sorting of the CD34$^-$/LSK cell populations from all the samples was done using FACS Aria II system (BD Bioscience, USA). The cells were sorted into lysis binding buffer (Dynabeads mRNA Direct Kit; Life Technologies AS, Norway). RNA was purified on Oligo-dT beads (Dynabeads mRNA Direct Kit; Life Technologies AS, Norway) and reverse transcribed into cDNA using Oligo-dT primers. The cDNA was turned into a double stranded DNA, and amplified by in vitro transcription. RNA was fragmented, reverse transcribed and illumina adaptors were added to complete the library for sequencing. The RNA sequencing was done at the Weizmann Institute of Science. The protocol that was used was as performed for single cell RNA sequencing, adjusted to low quantities of RNA (500 cells per sample).

Statistical Analysis

All statistical analyses were conducted using Prism 7 version. All data are expressed as mean±SEM, unpaired t-test two tailed *<0.05 <0.01*<0.001****<0.0001. Unless indicated otherwise in the figure legends. n values represent biological replicates.

Example 1

Figure 1B:
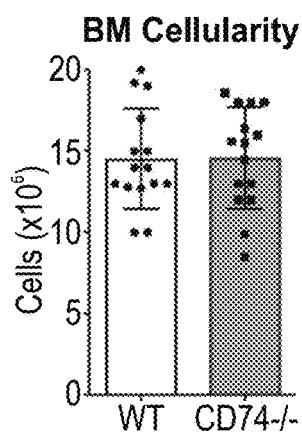
Figure 1C:
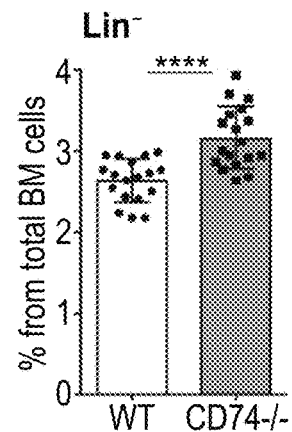
Figure 1D:
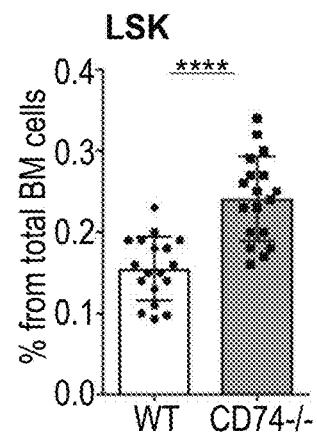
Figure 1E:
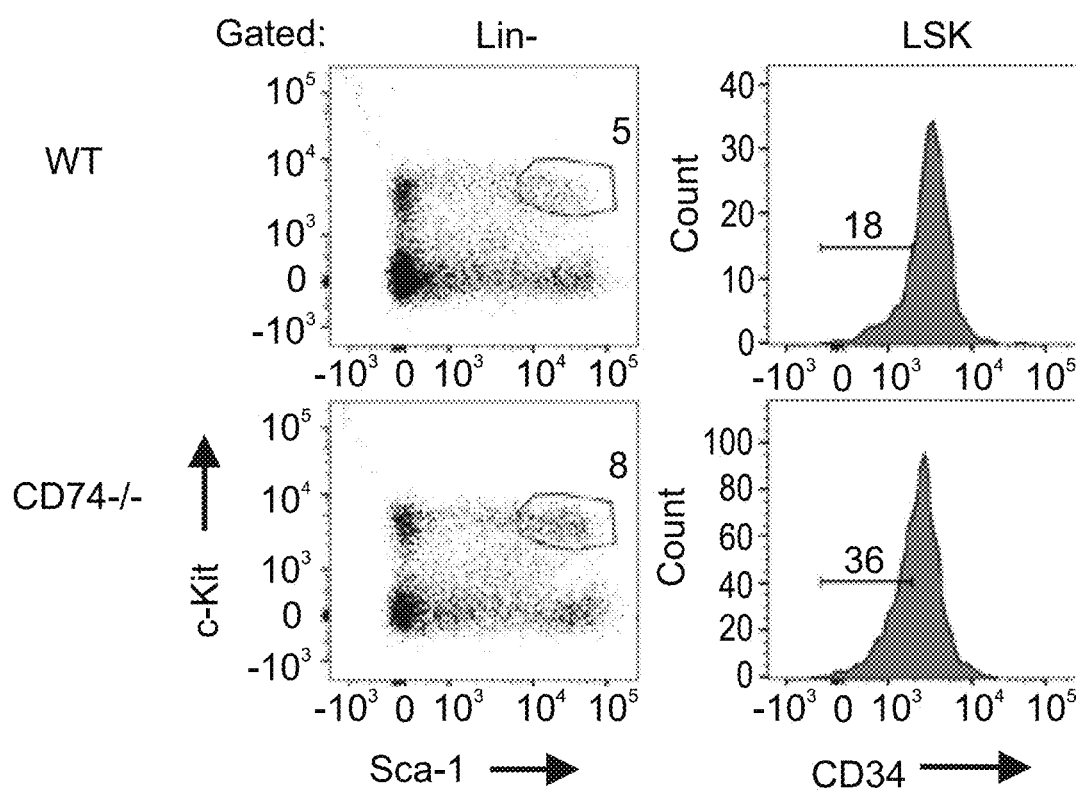
Figure 1F:
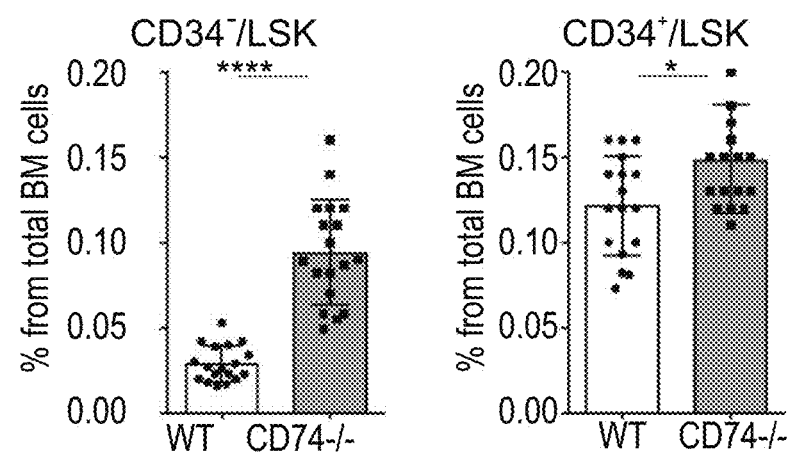
Figure 1G:
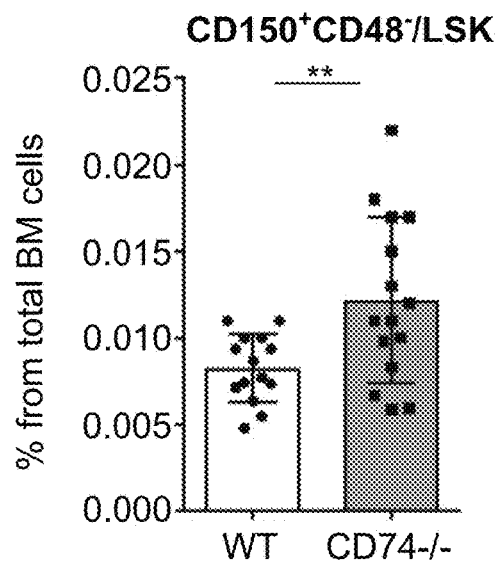
Figure 1H:
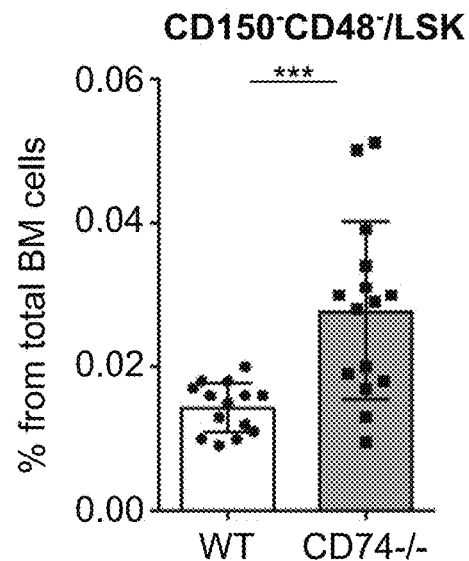
Figure 1I:
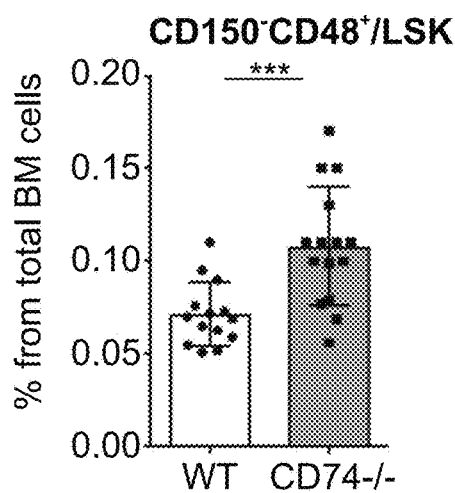

Expansion of Hematopoietic Stem and Progenitors Cell Populations in CD74$^{-/-}$ Mice CD74 mRNA is expressed in hematopoietic stem and progenitors cells (HSPCs). To determine whether CD74 protein is expressed on HSPCs (Lin$^-$Sca-1$^+$c-Kit$^+$; LSK), hematopoietic progenitors cells (HPCs; CD34$^+$Lin$^-$Sca-1$^+$ c-Kit$^+$) and hematopoietic stem cells (HSCs; CD34$^-$Lin$^-$Sca-1$^+$c-Kit$^+$) (gating is illustrated in FIGS. 2A-D), CD74 cell surface expression was analyzed by FACS. As shown in FIG. 1A, CD74 was expressed on the surface of these different populations. Next, to determine the function of CD74 in these cells, the number of the various stem and progenitors populations in WT and CD74$^{-/-}$ mice was compared. While similar numbers of BM cells were detected in WT and CD74$^{-/-}$ mice (FIG. 1B), a significant increase in Lineage marker-negative (CD11b$^-$, Gr-1$^-$, CD3$^-$, B220$^-$ and Ter117$^-$; FIG. 1C) and LSK (FIGS. 1D-E) populations was observed. LSK fraction is enriched for hematopoietic stem cells (HSCs). Therefore, for a more specific analysis, the expression of CD34 and the SLAM family members, CD150 and CD48, which characterize these populations, were followed. As shown in FIGS. 1E-F, a significant increase in the HPCs CD34$^+$LSK and HSCs CD34$^-$LSK population was detected in mice lacking CD74, with a more significant increase in the HSCs CD34$^-$ population. Similarly, an increase in the number of HSCs and progenitors characterized by the markers CD150, CD48, Lin, c-kit and Sca-1 (FIGS. 1G-I) was observed.

Since MIF is the natural ligand for CD74, the present inventors next analyzed the HSPCs populations in MIF$^{-/-}$ mice. Total BM cells were extracted from WT and MIF$^{-/-}$ mice and LSK and CD34$^-$LSK populations were analyzed. Higher numbers of Lin$^-$ and HSCs populations were observed in the MIF$^{-/-}$ mice compared to WT mice (FIGS. 2E-H), however the differences were not as significant as in the CD74 deficient mice. This could be explained by the existence of a MIF homologue, MIF2.

Figure 1J:
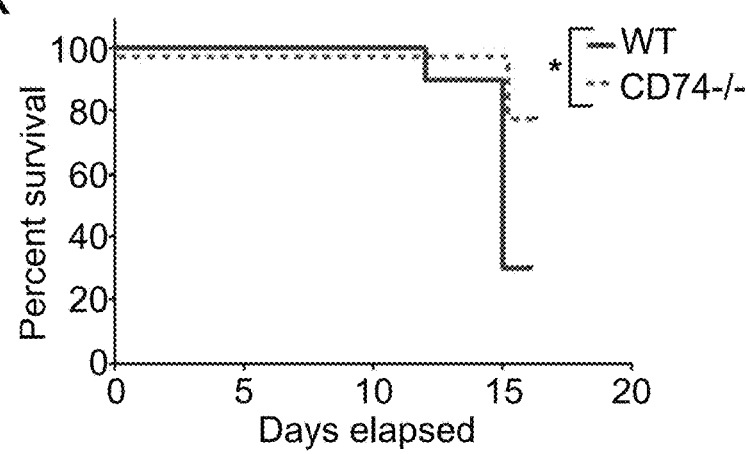

To substantiate further the accumulation of HSPCs in the absence of CD74 and to directly demonstrate the advantage of CD74 deficient cells in chemotherapy, WT and CD74$^{-/-}$ mice were injected weekly with the cell-cycle dependent myelotoxic agent 5-fluorouracil (5-FU), which kills proliferating cells and thereby stimulates HSCs to proliferate and replenish the hematopoietic system (Cheng et al., 2000). After the second injection of this drug, at day 14, only 30% of the WT mice were alive, in contrast to 80% of the CD74$^{-/-}$ mice (FIG. 1J). These results suggest that the quiescent stem cell population is upregulated in mice lacking CD74 (i.e. show an elevated survival), allowing a better replenishment of the immune system and survival of these mice under hemodepleting conditions.

Figure 3A:
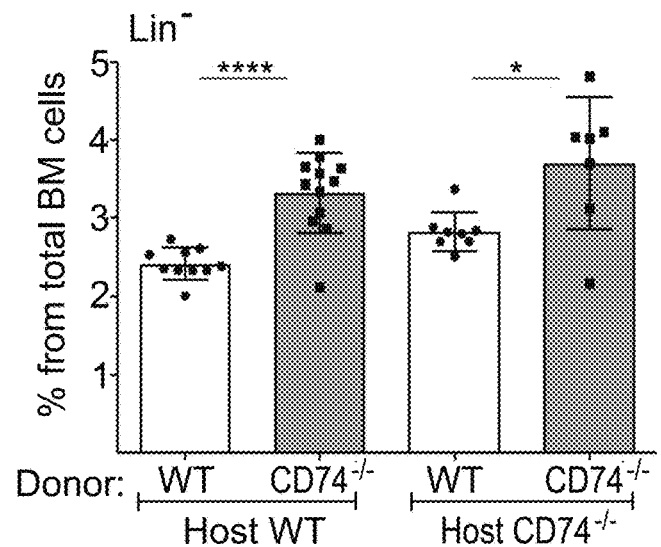
FIGS. 3A-C illustrate that $CD74^{-/-}$ HSPCs expansion is cell intrinsic. Lethally irradiated WT or $CD74^{-/-}$ mice were transplanted with either WT or $CD74^{-/-}$ total BM cells. Long-term reconstitution was evaluated 16 weeks post transplantation. Percentage from total BM cells was calculated for (FIG. 3A) $Lin^-$.
Figure 3B:
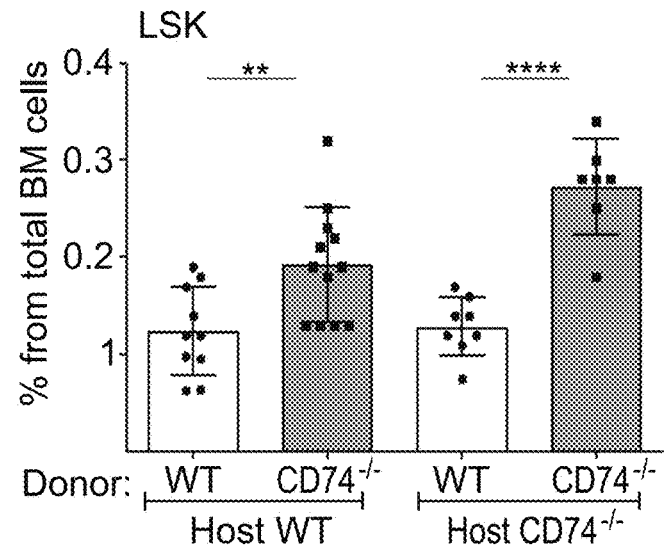
Figure 3C:
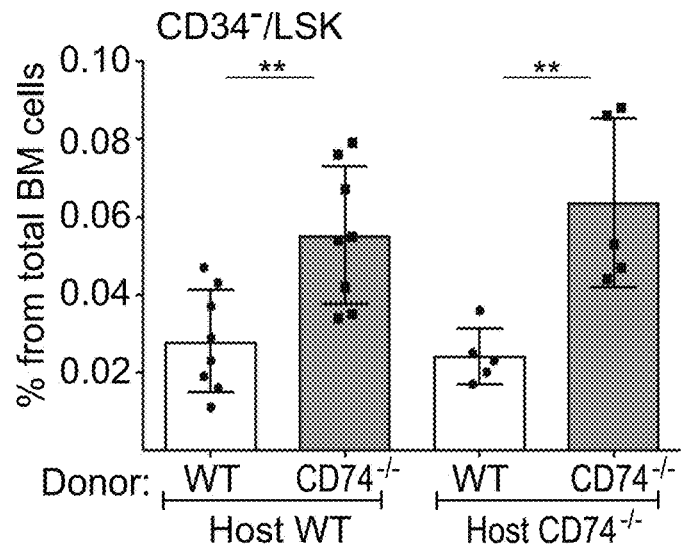

Next, to determine whether the expansion of HSPCs in CD74$^{-/-}$ results from an intrinsic effect, or whether the differences are due to the influence of the environment (extrinsic), chimeric mice were generated. Total BM cells from WT or CD74$^{-/-}$ mice were transplanted into lethal irradiated WT or CD74$^{-/-}$ recipients. The animals were sacrificed after 16 weeks and their HSPCs were analyzed. As seen in FIGS. 3A-C, an elevation in Lin$^-$, LSK and CD34$^-$LSK populations was detected in mice transplanted with the CD74$^{-/-}$ BM compared to WT donors. Thus, the lack of CD74 in the cells and not in their microenvironment contributed to HSPCs accumulation.

Taken together, these results indicate that the lack of MIF/CD74 signaling results in an intrinsic increase in the HSPCs population in the bone marrow.

Example 2

CD74$^{-/-}$ HSPCs Demonstrate Better Long-Term Self-Renewal Capacity

Figure 4A:
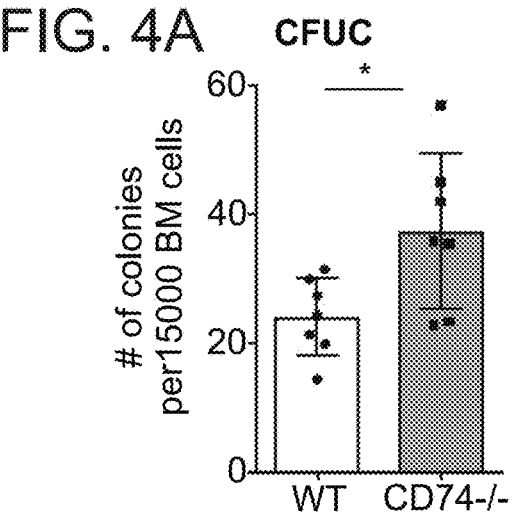

The present inventors next examined the in vitro and in vivo repopulation potential of CD74 deficient stem cells. The ability of the HSPCs to proliferate and differentiate into colonies in vitro was analyzed by a colony-forming unit cells assay (CFU-C assay). As seen in FIG. 4A, higher numbers of colonies were generated from CD74$^{-/-}$ BM when compared to WT.

Figure 4B:
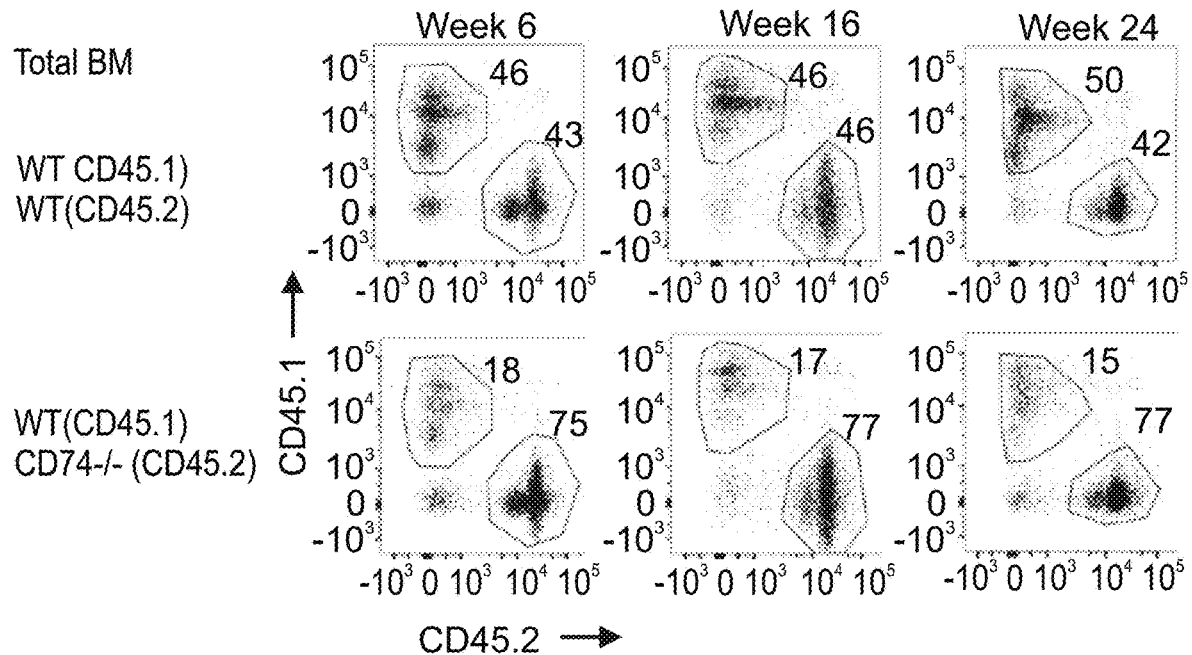
Figure 4C:
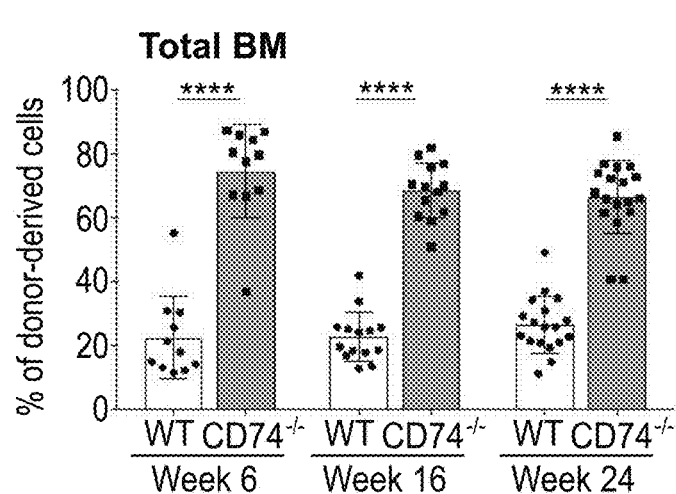
Figure 5A:
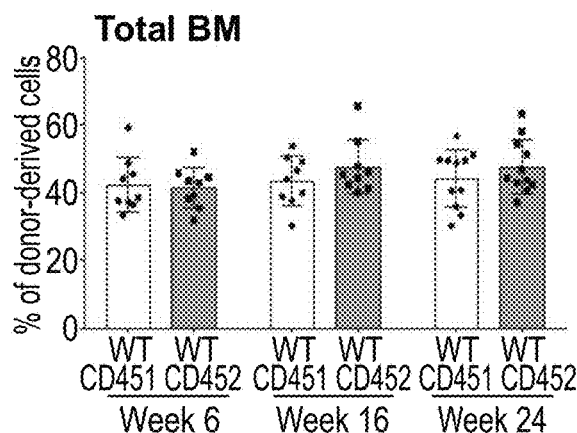
FIGS. 5A-E illustrate lethally irradiated WT (CD45.1) mice transplanted with WT (CD45.2) mice at a 1:1 ratio. Mice were analyzed 6, 16, and 24 weeks after transplantation.
Figure 5B:
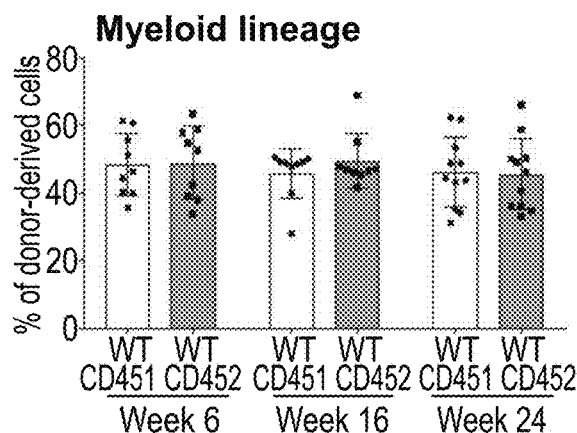
Figure 5C:
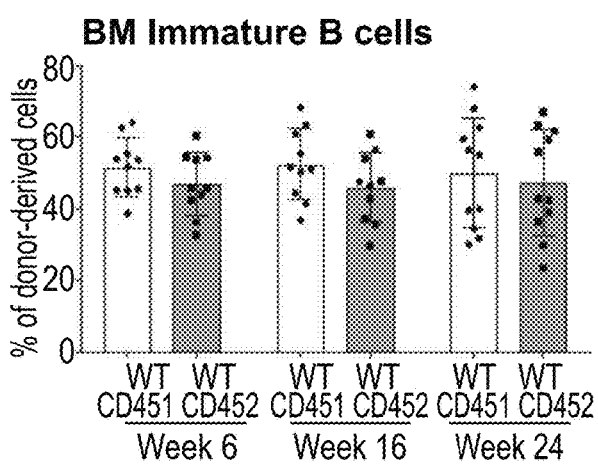
Figure 5D:
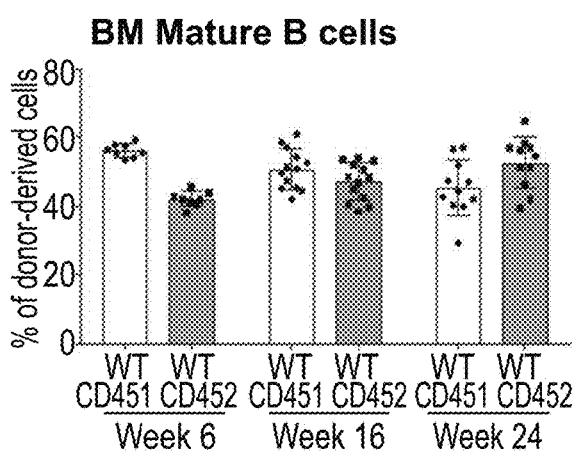
Figure 5E:
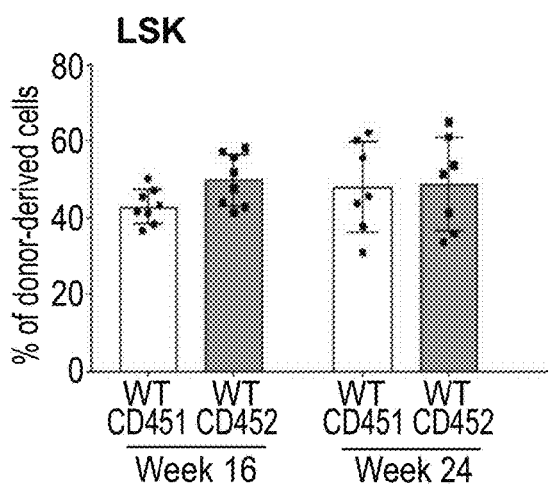

To follow the in vivo potential of HPSCs lacking CD74 to repopulate, WT (CD45.1) BM cells were transplanted in a 1:1 ratio with either WT (CD45.2) or CD74$^{-/-}$ (CD45.2) cells into lethally irradiated recipient mice (CD45.1). BM and peripheral blood (PB) populations of the mix chimeras were analyzed at 6, 16 and 24 weeks after transplantation. As shown in FIGS. 4B-I and FIGS. 5A-E, CD74$^{-/-}$ derived BM cells had an advantage over the WT populations. The dramatic takeover of CD74$^{-/-}$ cells was observed as soon as 6 weeks post-transplant and maintained throughout the experiment. A significant advantage of CD74$^{-/-}$ total BM cells (FIGS. 4B-C), myeloid (FIG. 4D), B cells (FIG. 4E) and HSCs populations (FIG. 4F-G) was observed in the different time points. In the B cell lineage, the advantage of CD74$^{-/-}$ population was detected from early stages of B cell differentiation through the formation of immature B cell stage in the BM (FIG. 4H). This advantage disappeared in the mature stage (FIG. 4I), probably due to the role of CD74 as a survival receptor on these cells. Furthermore, the advantage of CD74 deficient HSPCs was also obtained in a competitive chimera in a ratio of 3:1 (WT CD45.1 with CD74$^{-/-}$ CD45.2 or WT CD45.1) (FIGS. 9A-F). Next, to directly test the repopulation ability of CD74$^{-/-}$ HSPCs, sorted LSK population from WT and CD74$^{-/-}$ mice were transplanted in a 1:1 ratio to irradiated recipient mice (CD45.1) to generate competitive BM chimera. Bone marrow populations of the mix chimeras were analyzed 6 and 18 weeks following the transplantation. As shown in FIGS. 6A-E, a significant advantage of CD74$^{-/-}$ BM cells was observed 6 and 18 weeks post engraftment. These results indicated that CD74 deficient short- and long-term stem cells had an advantage in repopulating the host environment, as seen by the significantly higher levels of those cells when compared to the WT (CD45.1).

Figure 6A:
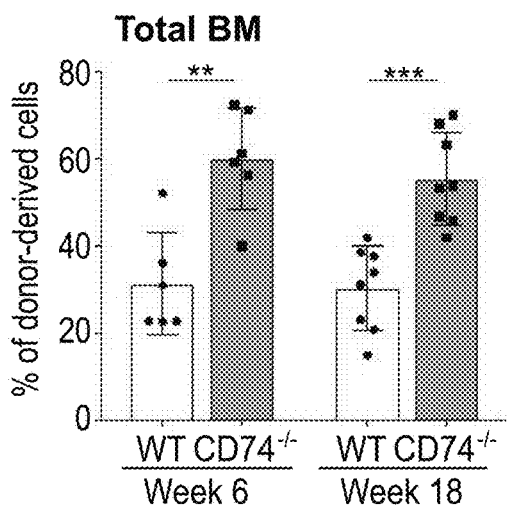
FIGS. 6A-I illustrate that $CD74^{-/-}$ HSPCs demonstrate better long-term self-renewal capacity. Lethally irradiated WT CD45.1 recipient mice were reconstituted with $7.5 \times 10^4$ sorted LSK cells from WT (CD45.1) and $CD74^{-/-}$ (CD45.2) in a 1:1 ratio. Percentage from donor-derived cells were analyzed in the BM after 6 and 18 weeks for (FIG. 6A) Total BM cells.
Figure 6B:
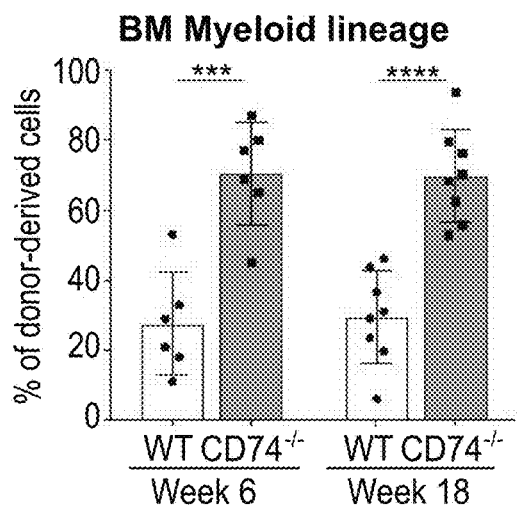
Figure 6C:
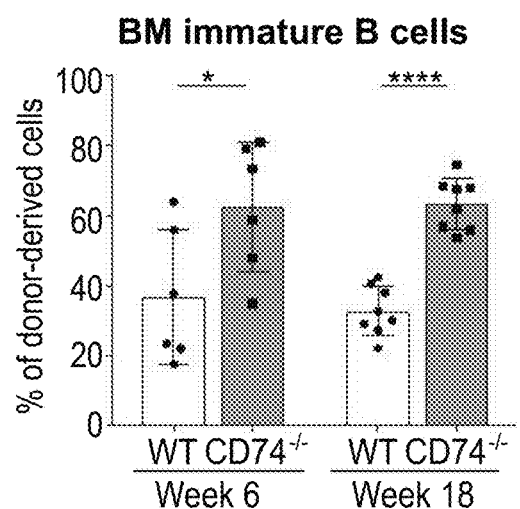
Figure 6D:
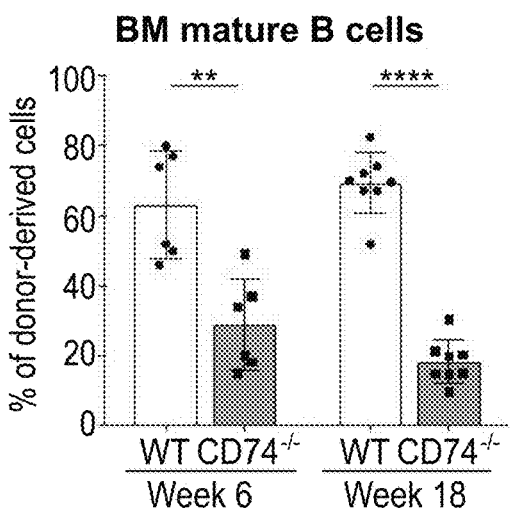
Figure 6E:
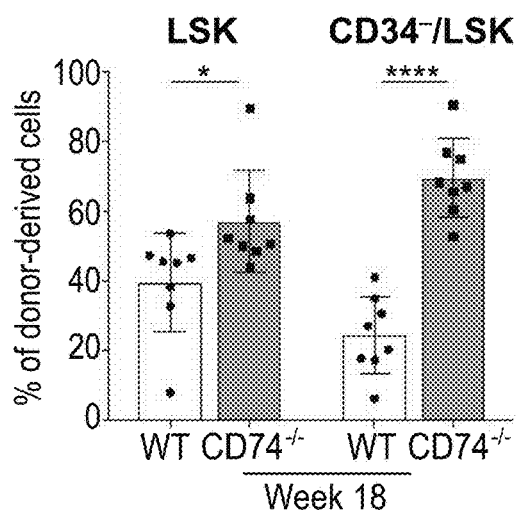
Figure 6F:
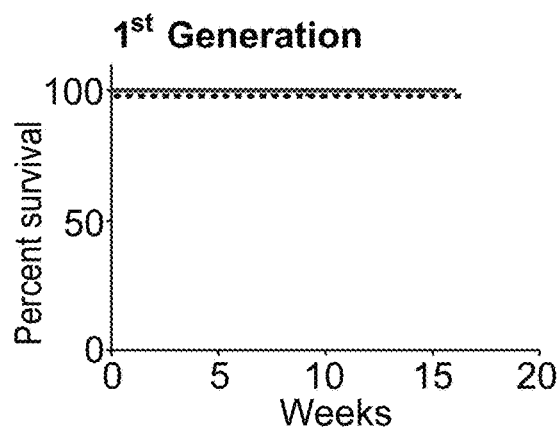
Figure 6G:
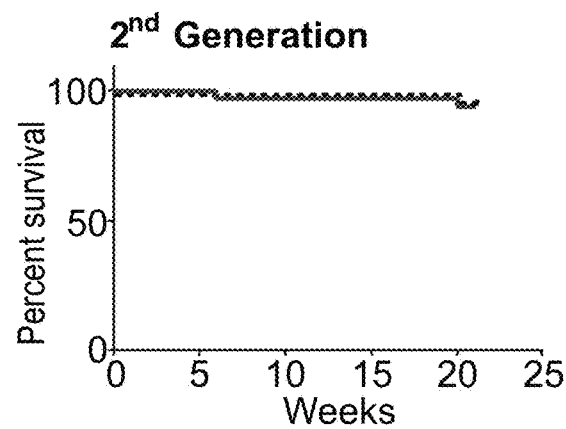
Figure 6H:
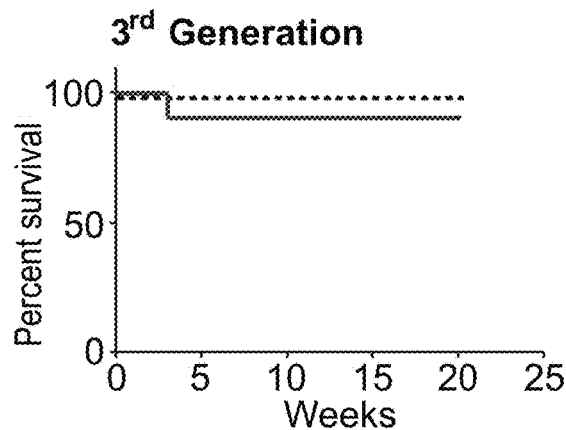
Figure 6I:
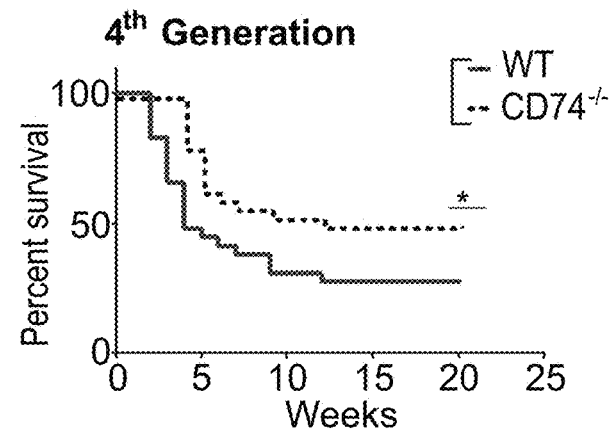

To directly evaluate the long-term self-renewal and functional properties of CD74$^{-/-}$ HSPCs, a serial BM transplantation assay was performed. BM cells from six WT and six CD74$^{-/-}$ mice were obtained and serially transplanted the cells into lethally irradiated WT mice. During the three first cycles no significant differences between WT and CD74$^{-/-}$ groups were observed (FIGS. 6F-H). However, in the fourth cycle of transplantation CD74$^{-/-}$ transplanted mice showed a better survival rate compared to the rate of WT mice (57% compare to 33%) (FIG. 6I). Thus, the absence of CD74 results in accumulation of HSPCs with a higher potential to repopulate.

Example 3

CD74 Regulates Stem Cell Retention, Maintenance and Survival

Figure 7F:
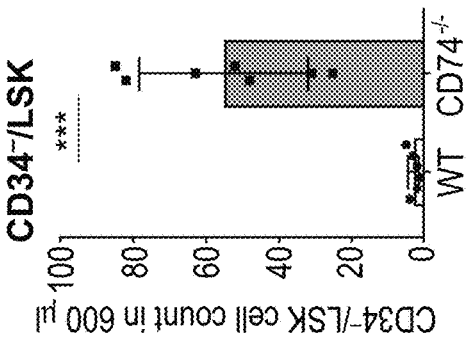
Figure 7E:
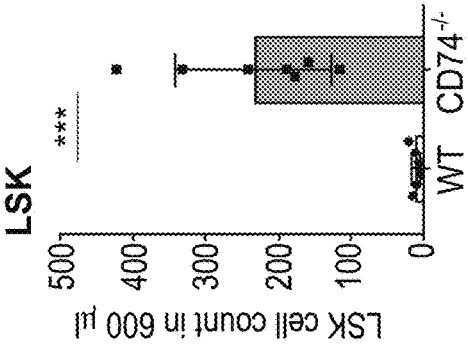
Figure 7C:
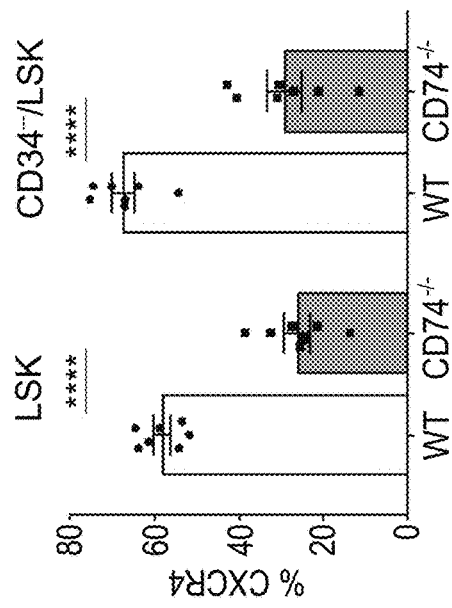
Figure 7B:
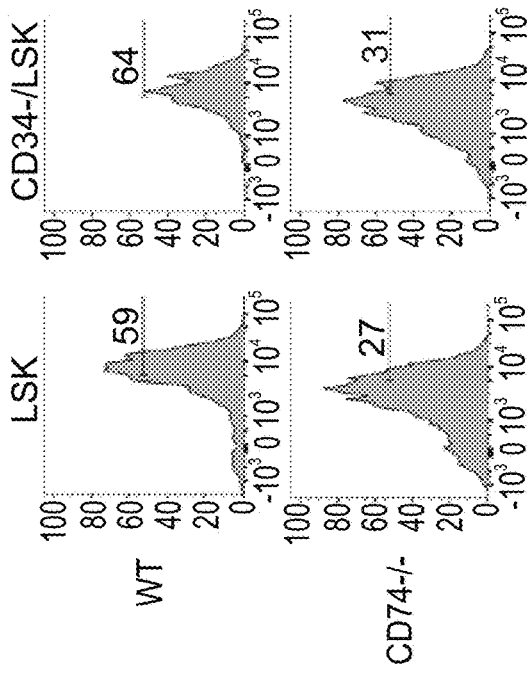

Next, the present inventors wished to follow the molecular mechanism regulating the HSPCs phenotype. Although, there is an accumulation of CD74$^{-/-}$ stem cells in the BM, no significant global accumulation of cells was detected in this compartment (FIG. 1B). This accumulation might result from their elevated retention in the BM niche or upregulation in their proliferation or survival. Since CXCR4 plays a major role in migration, retention, survival and proliferation of hematopoietic stem cells (HSCs) and hematopoietic stem and progenitors cells (HSPCs), the present inventors next wished to follow the role of CD74 in CXCR4 expression and function in HSPCs. It was previously shown that following activation of CD74 expressed on chronic lymphocytic leukemia (CLL) cells, CD74-ICD binds the chromatin of the CXCR4 promoter (Gil-Yarom et al., 2017). To further test the binding of CD74-ICD to the chromatin of CXCR4 in more relevant cells, Chip-sequencing was performed following activation of CD74 on lineage negative mouse bone-marrow cells. As shown in FIG. 7A, CD74-ICD binds to elements near CXCR4 genes. Next, expression of cell surface CXCR4 on HPSCs was analyzed on WT and CD74 deficient mice. As shown in FIGS. 7B-C, a reduction in the expression of CXCR4 on the cell surface was observed on CD74$^{-/-}$ cells. Together, these results show that CD74 regulates CXCR4 expression.

Figure 7D:
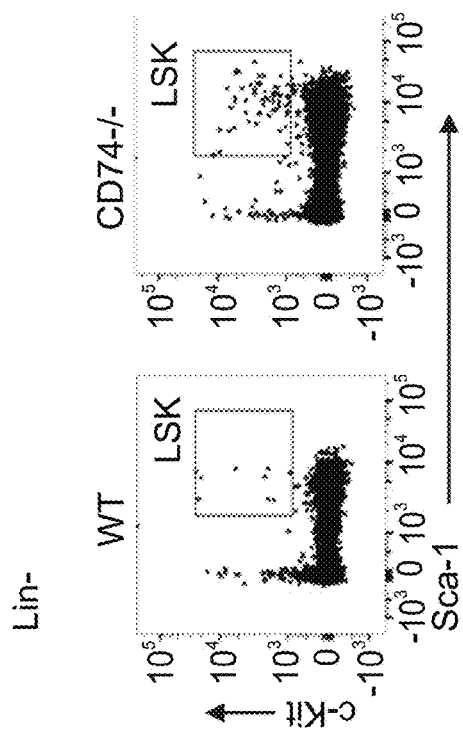
Figure 9A:
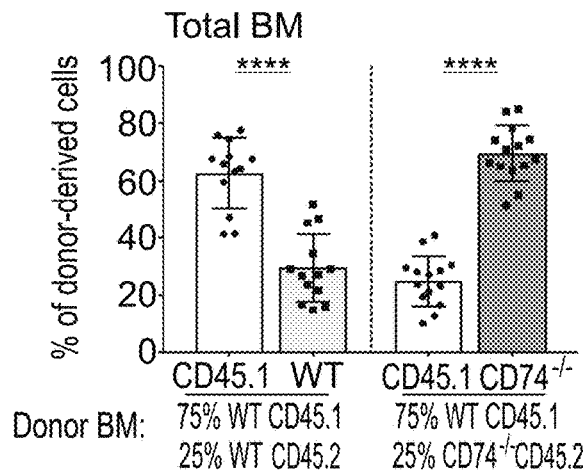
FIGS. 9A-F illustrate that CD74 deficient HSPCs show a quality advantage in cell repopulation. Lethally irradiated WT (CD45.1) mice were transplanted with WT (CD45.2) or CD74$^{-/-}$ (CD45.2) mice at a 3:1 ratio. Mice were analyzed 16 weeks after transplantation. Graphs show percent of donor derived (FIG. 9A) BM cells.
Figure 9B:
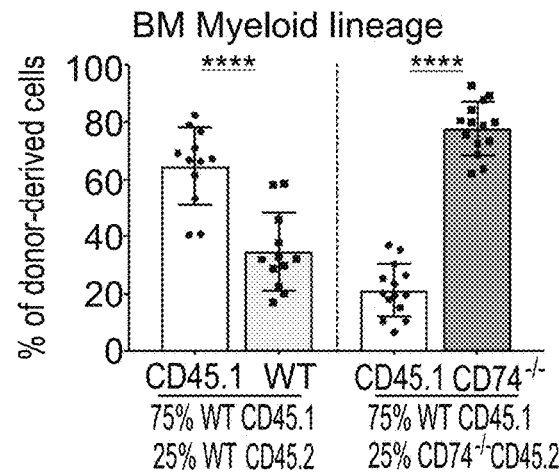
Figure 9C:
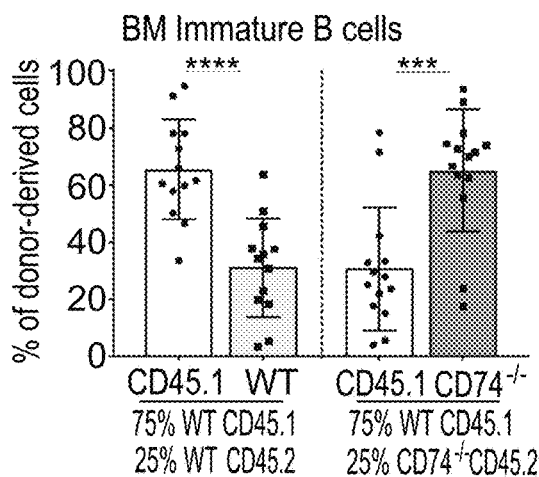
Figure 9D:
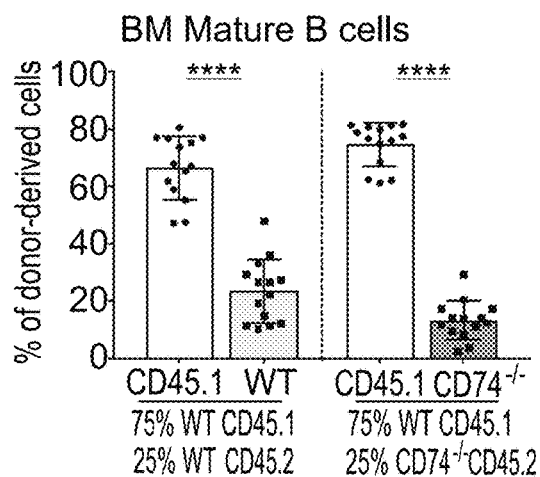
Figure 9E:
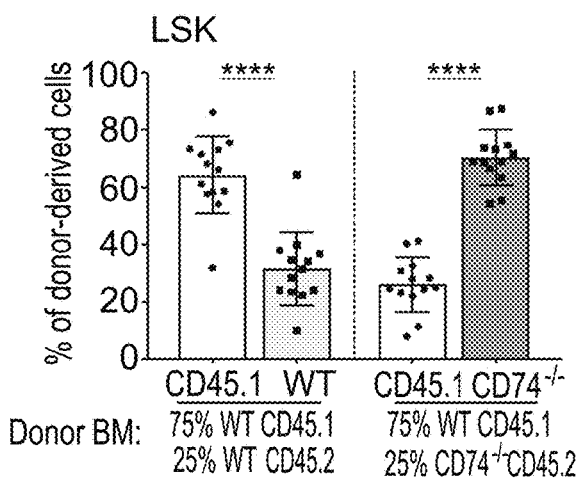
Figure 9F:
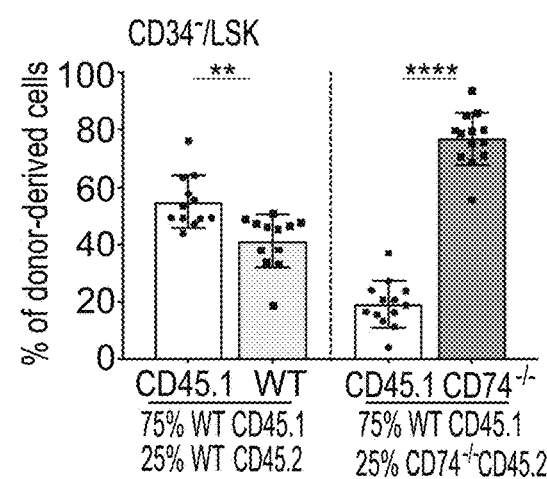

As was recently shown, CXCR4 reduced expression levels might result in amplified mobilization response and induced cell proliferation in the BM (Karpova et al., 2017). To determine whether the reduced levels of CD74 affect HSPCs retention, the total counts of HSPCs in WT and CD74$^{-/-}$ PB were compared. As shown in FIGS. 7D-F, a dramatic elevation in the number of HSPCs in the circulation of CD74 deficient mice was detected. Thus, in the absence of CD74, lower CXCR4 levels results in reduced retention of HSPCs in the BM. Next, the role of CD74 in the maintenance of CD74 deficient HSPCs was analyzed. To determine whether CD74 control cell proliferation and cycle, Ki67 levels were followed. No difference in the percent of cycling (Ki67 positive) cells from CD34$^-$ or CD34$^+$ populations was detected in the WT and CD74$^{-/-}$ mice (FIG. 8A). However, since higher numbers of LSK, CD34$^-$ and CD34$^+$ cells were detected in the CD74$^{-/-}$ mice, the number of both quiescent and cycling stem cells (CD34$^-$) and progenitors (CD34$^+$) were elevated in these mice (FIGS. 8B-C). To further follow cell proliferation in mice lacking CD74, 5-bromodeoxyuridine (BrdU) labeling experiment was performed. Mice were fed with 0.8 mg/ml BrdU in the drinking water for 3 days and BrdU incorporation was followed. As shown in FIGS. 8D-E, although higher numbers of both quiescent and cycling cells were detected CD74$^{-/-}$ mice, no significant change in the ratio of these populations was observed. These results imply that lower levels of CD74 and CXCR4 do not induce HSPCs proliferation.

Emerging evidence shows that oxidative stress, in particular reactive oxygen species (ROS) content, influences stem cell migration, development, and self-renewal as well as their cell cycle status (Ludin et al., 2014). Electron transfer along the mitochondrial respiration chain induces the formation of ROS (Kobayashi and Suda, 2012). To determine whether in the absence of CD74 in stem cells, the metabolism of glucose via oxidative phosphorylation is elevated, ROS levels were compared in HSPCs of CD74$^{-/-}$ and WT cells. As can be seen in FIGS. 8F-G, higher number of ROS$^{high}$ cells were detected in the CD74$^{-/-}$ HSCs compared to the WT. To determine whether excess of ROS contributes to the expansion of CD74$^{-/-}$ stem cells, ROS levels were reduced using the antioxidant N-acetyl-L-cystein (NAC). As shown in FIGS. 8H-I, treatment with NAC for 6 days partially reduced the levels of HSPCs in the CD74$^{-/-}$ mice to WT levels. This suggests that ROS levels results in HSPCs accumulation in mice lacking CD74.

To further determine the mechanism of action of CD74 in HSPCs, the present inventors next wished to determine whether the higher number of CD74$^{-/-}$ HSPCs results from an induced cell survival. Therefore, HSPCs cells were analyzed for cell survival using Annexin v staining assay. As shown in FIG. 8J, reduced apoptosis was observed in the CD74$^{-/-}$ CD34$^-$ cells compared to the WT population. Thus, the higher number of CD74$^{-/-}$ stem cells may result from an increase in their survival. Furthermore, since hypoxic condition exist in the BM and especially the perivascular niches where the non-dividing HSCs reside, WT and CD74$^{-/-}$ BM cells were incubated in hypoxia condition for 24 hours and cell survival was analyzed by annexin V staining. As can be seen in FIG. 8K CD74 deficient stem cells survived better in hypoxia conditions compared to WT stem cells. Transfer of the CD74$^{-/-}$ cells to normoxic conditions reduced the advantage of these cells compared to WT stem cells (FIG. 8L). These results support the suggestion that the BM hypoxic conditions play a role in the control of CD74 function. Further, to determine the global effect of CD74 in HSPCs, the function of CD74 as a transcription regulator in HSPCs was followed. The binding of CD74-ICD to the CXCR4 promoter in early progenitors was determined (FIG. 7A).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

LIST OF REFERENCES

Bucala, R., and Shachar, I. (2014). The integral role of CD74 in antigen presentation, MIF signal transduction, and B cell survival and homeostasis. Mini Rev Med Chem 14, 1132-1138.

Cheng, T., Rodrigues, N., Shen, H., Yang, Y., Dombkowski, D., Sykes, M., and Scadden, D. T. (2000). Hematopoietic stem cell quiescence maintained by p21cip1/waf1. Science 287, 1804-1808.

Cohen, S., and Shachar, I. (2012). Cytokines as regulators of proliferation and survival of healthy and malignant peripheral B cells. Cytokine 60, 13-22.

Gil-Yarom, N., Radomir, L., Sever, L., Kramer, M. P., Lewinsky, H., Bornstein, C., Blecher-Gonen, R., Barnett-Itzhaki, Z., Mirkin, V., Friedlander, G., et al. (2017). CD74 is a novel transcription regulator. Proc Natl Acad Sci USA 114, 562-567.

Gore, Y., Starlets, D., Maharshak, N., Becker-Herman, S., Kaneyuki, U., Leng, L., Bucala, R., and Shachar, I. (2008). Macrophage migration inhibitory factor (MIF) induces B cell survival by activation of a CD74/CD44 receptor complex. J Biol Chem 283, 2784-2792.

Karpova, D., Ritchey, J. K., Holt, M. S., Abou-Ezzi, G., Monlish, D., Batoon, L., Millard, S., Spohn, G., Wiercinska, E., Chendamarai, E., et al. (2017). Continuous blockade of CXCR4 results in dramatic mobilization and expansion of hematopoietic stem and progenitor cells. Blood 129, 2939-2949.

Klimmeck, D., Cabezas-Wallscheid, N., Reyes, A., von Paleske, L., Renders, S., Hansson, J., Krijgsveld, J., Huber, W., and Trumpp, A. (2014). Transcriptome-wide profiling and posttranscriptional analysis of hematopoietic stem/progenitor cell differentiation toward myeloid commitment. Stem Cell Reports 3, 858-875.

Kobayashi, C. I., and Suda, T. (2012). Regulation of reactive oxygen species in stem cells and cancer stem cells. J Cell Physiol 227, 421-430.

Kollet O, Dar A, Shivtiel S, Kalinkovich A, Lapid K, Sztainberg Y et al. (2006). Osteoclasts degrade endosteal components and promote mobilization of hematopoietic progenitor cells. Nat Med 12, 657-664.

Ludin, A., Gur-Cohen, S., Golan, K., Kaufmann, K. B., Itkin, T., Medaglia, C., Lu, X. J., Ledergor, G., Kollet, O., and Lapidot, T. (2014). Reactive oxygen species regulate hematopoietic stem cell self-renewal, migration and development, as well as their bone marrow microenvironment. Antioxid Redox Signal 21, 1605-1619.

Starlets, D., Gore, Y., Binsky, I., Haran, M., Harpaz, N., Shvidel, L., Becker-Herman, S., Berrebi, A., and Shachar, I. (2006). Cell Surface CD74 initiates a signaling cascade leading to cell proliferation and survival. Blood 107, 4807-4816.

Sugiyama, T., Kohara, H., Noda, M., and Nagasawa, T. (2006). Maintenance of the hematopoietic stem cell pool by CXCL12-CXCR4 chemokine signaling in bone marrow stromal cell niches. Immunity 25, 977-988.

What is claimed is:

1. A method of generating hematopoietic stem cells having an increased survival and expansion potential, the method comprising:
    (a) collecting a population of cells comprising hematopoietic stem cells;
    (b) isolating said hematopoietic stem cells by separating CD34+ cells from said population of cells using Magnetic-activated cell sorting (MACS) or fluorescence-activated cell sorting (FACS); and
    (c) contacting said population of cells following said (b) with an agent capable of decreasing an activity or expression of CD74 and/or of macrophage migration inhibitory factor (MIF),
    to thereby generate hematopoietic stem cells having an increased survival and/or increased expansion potential while maintaining their differentiation potential as compared to hematopoietic stem cells not contacted with said agent, and wherein said hematopoietic stem cells are not transduced with a lentivirus.

2. The method of claim 1, wherein said contacting is effected ex vivo or in vitro.

3. The method of claim 1, further comprising a step of mobilizing said hematopoietic stem cells from the bone marrow to the peripheral blood prior to collecting.

4. The method of claim 1, wherein said hematopoietic stem cells:
    are characterized by the phenotype $CD34^+$, $CD59^+$, $CD90/Thy1^+$, $CD38^{+/-}$, $c-Kit^{-/+}$, and $Lin^-$; or
    are characterized by the phenotype $CD34^+$, $CD59^+$, $CD90/Thy1^-$, $CD38^{+/-}$, $c-Kit^{-/+}$, and $Lin^-$; and/or
    are capable of differentiating into myeloid cells and/or lymphoid cells.

5. The method of claim 1, wherein said agent capable of decreasing an activity or expression of CD74 and/or of MIF is a polynucleotide agent, a small molecule or an antibody.

6. The method of claim 1, wherein:
    said agent capable of decreasing an activity or expression of CD74 and/or of MIF prevents the binding of said MIF to said CD74; and/or
    said agent capable of decreasing an activity or expression of CD74 and/or of MIF downregulates an activity or expression of CXCR4 in said hematopoietic stem cells; and/or
    said agent capable of decreasing an activity or expression of CD74 upregulates content of reactive oxygen species (ROS) in said hematopoietic stem cells.

7. The method of claim 1, wherein said agent capable of decreasing an activity or expression of CD74 is Milatuzumab and/or said agent capable of decreasing an activity or expression of MIF is Imalumab.

* * * * *